(12) United States Patent
Wu et al.

(10) Patent No.: US 10,421,763 B2
(45) Date of Patent: Sep. 24, 2019

(54) COMPOSITIONS OF PROTEIN RECEPTOR TYROSINE KINASE INHIBITORS

(71) Applicant: Purdue Pharma L.P., Stamford, CT (US)

(72) Inventors: Jay Jie-Qiang Wu, Fremont, CA (US); Ling Wang, Fremont, CA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 15/676,039

(22) Filed: Aug. 14, 2017

(65) Prior Publication Data

US 2018/0086777 A1  Mar. 29, 2018

Related U.S. Application Data

(63) Continuation of application No. 14/685,806, filed on Apr. 14, 2015, now Pat. No. 9,738,659, which is a continuation of application No. 13/133,565, filed as application No. PCT/US2009/067197 on Dec. 8, 2009, now Pat. No. 9,040,508.

(60) Provisional application No. 61/120,827, filed on Dec. 8, 2008.

(51) Int. Cl.

| | |
|---|---|
| *A61K 31/496* | (2006.01) |
| *A61K 31/497* | (2006.01) |
| *A61K 45/06* | (2006.01) |
| *C07D 403/14* | (2006.01) |
| *C07D 407/12* | (2006.01) |
| *C07D 413/10* | (2006.01) |
| *C07D 413/12* | (2006.01) |
| *C07D 417/12* | (2006.01) |
| *C07D 471/04* | (2006.01) |
| *C07D 487/04* | (2006.01) |
| *C07D 491/04* | (2006.01) |
| *C07D 215/20* | (2006.01) |
| *C07D 221/06* | (2006.01) |
| *C07D 223/32* | (2006.01) |
| *C07D 241/44* | (2006.01) |
| *C07D 261/20* | (2006.01) |
| *C07D 265/36* | (2006.01) |
| *C07D 279/16* | (2006.01) |
| *C07D 295/13* | (2006.01) |
| *C07D 307/77* | (2006.01) |
| *C07D 498/06* | (2006.01) |
| *C07D 493/06* | (2006.01) |
| *C07D 495/04* | (2006.01) |
| *C07D 498/04* | (2006.01) |
| *C07D 513/04* | (2006.01) |

(52) U.S. Cl.
CPC .......... *C07D 498/06* (2013.01); *A61K 31/496* (2013.01); *A61K 31/497* (2013.01); *A61K 45/06* (2013.01); *C07D 215/20* (2013.01); *C07D 221/06* (2013.01); *C07D 223/32* (2013.01); *C07D 241/44* (2013.01); *C07D 261/20* (2013.01); *C07D 265/36* (2013.01); *C07D 279/16* (2013.01); *C07D 295/13* (2013.01); *C07D 307/77* (2013.01); *C07D 403/14* (2013.01); *C07D 407/12* (2013.01); *C07D 413/10* (2013.01); *C07D 413/12* (2013.01); *C07D 417/12* (2013.01); *C07D 471/04* (2013.01); *C07D 487/04* (2013.01); *C07D 491/04* (2013.01); *C07D 493/06* (2013.01); *C07D 495/04* (2013.01); *C07D 498/04* (2013.01); *C07D 513/04* (2013.01)

(58) Field of Classification Search
CPC .. C07D 403/12; C07D 403/14; A61K 31/497; A61K 31/496
See application file for complete search history.

(56) References Cited

U.S. PATENT DOCUMENTS

| | | | |
|---|---|---|---|
| 3,609,152 | A | 9/1971 | Hess et al. |
| 4,337,341 | A | 6/1982 | Zimmerman |
| 5,112,598 | A | 5/1992 | Biesalski |
| 5,556,611 | A | 9/1996 | Biesalski |
| 5,698,155 | A | 12/1997 | Grosswald et al. |
| 7,252,822 | B2 | 8/2007 | Shelton et al. |

(Continued)

FOREIGN PATENT DOCUMENTS

| | | |
|---|---|---|
| CN | 101223175 A | 7/2008 |
| RU | 2065438 C1 | 8/1996 |

(Continued)

OTHER PUBLICATIONS

International Search Report and Written Opinion of the International Searching Authority for International Application No. PCT/US2014/027591, dated Aug. 29, 2014, 12 pages.

(Continued)

*Primary Examiner* — Amanda L Aguirre
(74) *Attorney, Agent, or Firm* — Sterne, Kessler, Goldstein & Fox P.L.L.C.

(57) ABSTRACT

The present invention relates to novel synthetic substituted heterocyclic compounds and pharmaceutical compositions containing the same that are capable of inhibiting or antagonizing a family of receptor tyrosine kinases, Tropomysosin Related Kinases (Trk), in particular the nerve growth factor (NGF) receptor, TrkA. The invention further concerns the use of such compounds in the treatment and/or prevention of pain, cancer, restenosis, atherosclerosis, psoriasis, thrombosis, or a disease, disorder or injury relating to dysmyelination or demyelination or the disease or disorder associated with abnormal activities of NGF receptor TrkA.

15 Claims, No Drawings

(56) References Cited

U.S. PATENT DOCUMENTS

| | | | |
|---|---|---|---|
| 7,425,329 | B2 | 9/2008 | Shelton et al. |
| 7,671,077 | B2 | 3/2010 | Lin |
| 7,718,674 | B2 | 5/2010 | Aberg |
| 8,669,265 | B2 | 3/2014 | Reddy et al. |
| 8,999,992 | B2 | 4/2015 | Wu et al. |
| 9,388,146 | B2 | 7/2016 | Wu et al. |
| 9,718,794 | B2 | 8/2017 | Wu et al. |
| 9,738,659 | B2 | 8/2017 | Wu et al. |
| 9,993,473 | B2 | 6/2018 | Wu et al. |
| 10,124,002 | B2 | 11/2018 | Wu et al. |
| 2004/0071701 | A1 | 4/2004 | Delafoy et al. |
| 2004/0131615 | A1 | 7/2004 | Shelton et al. |
| 2008/0113974 | A1 | 5/2008 | Hurtevent et al. |
| 2008/0161292 | A1* | 7/2008 | Giranda ............... C07D 241/08 514/220 |
| 2011/0160240 | A1 | 6/2011 | Ryckman et al. |
| 2012/0003184 | A1 | 1/2012 | Garcia Gonzalez et al. |
| 2013/0158264 | A1 | 6/2013 | Castelhano et al. |
| 2015/0174124 | A1 | 6/2015 | Wu et al. |
| 2016/0002182 | A1 | 1/2016 | Wu et al. |
| 2017/0313666 | A1 | 11/2017 | Wu et al. |
| 2018/0057469 | A1 | 6/2018 | Wu et al. |

FOREIGN PATENT DOCUMENTS

| | | |
|---|---|---|
| WO | WO 2004/071486 | 8/2004 |
| WO | WO 2006/007864 A1 | 1/2006 |
| WO | WO 2006/078711 A2 | 7/2006 |
| WO | WO 2010/077680 A2 | 7/2010 |
| WO | WO 2012/097000 A1 | 7/2012 |
| WO | WO 2012/119079 A1 | 9/2012 |

OTHER PUBLICATIONS

Wang, F., et al., "Design, synthesis, biochemical studies, cellular characterization, and structure-based computational studies of small molecules targeting the urokinase receptor," *Bioorganic & Medicinal Chemistry* 20:4760-4773, Elsevier Ltd., United States (Jun. 2012).

McCarthy, C. and Walker, E., "Tropomyosin receptor kinase inhibitors: a patent update 2009-2013," *Expert Opin. Ther. Patents* 24(7):731-744, Informa UK, Ltd., England (Jul. 2014).

Zhang, J., et al., "Targeting cancer with small molecule kinase inhibitors," *Nature Reviews* 9:28-39, Macmillan Publishers Limited, England (Jan. 2009).

Stachel, S.J., et al., "Maximizing Diversity from a Kinase Screen: Identification of Novel and Selective pan-Trk Inhibitors for Chronic Pain," *Journal of Medicinal Chemistry* 57:5800-5816, American Chemical Society, United States (Jul. 2014).

Berge, S.M., et al., "Pharmaceutical Salts," *Journal of Pharmaceutical Sciences* 66(1):1-19, Wiley-Liss, Inc., United States (Jan. 1977).

Hancock, B.C. and Parks, M., "What is the True Solubility Advantage for Amorphous Pharmaceuticals?" *Pharmaceutical Research* 17(4):397-404, Plenum Publishing Corporation, United States (Apr. 2000).

Bennett, G.J. and Xie, Y.K., "A peripheral mononeuropathy in rat that produces disorders of pain sensation like those seen in man," *Pain* 33(1):87-107, Elsevier Science Publishers B.V., Netherlands (1988).

Calcutt, N.A., "Experimental models of painful diabetic neuropathy," *J. Neurol. Sci.* 220(1-2):137-139, Elsevier B.V., Netherlands (2004).

Kim, S.H. and Chung, J.M., "An experimental model for peripheral neuropathy produced by segmental spinal nerve ligation in the rat," *Pain* 50(3):355-363, Elsevier Science Publishers B.V., Netherlands (1992).

Lynch, J.J., III et al, "An adenosine kinase inhibitor attenuates tactile allodynia in a rat model of diabetic neuropathic pain," *Eur. J. Pharmacol.* 364(2-3):141-146, Elsevier Science, Netherlands (1999).

Office Action dated Jul. 16, 2014 in U.S. Appl. No. 14/208,244, Wu, et al., filed Mar. 13, 2014.

Office Action dated Sep. 8, 2014 in U.S. Appl. No. 14/208,244, Wu, et al., filed Mar. 13, 2014.

Notice of Allowance dated Dec. 3, 2014 in U.S. Appl. No. 14/208,244, Wu, et al., filed Mar. 13, 2014.

Office Action dated Nov. 2, 2016 in U.S. Appl. No. 14/772,264, Wu et al., § 371(c) date Dec. 28, 2015.

Notice of Allowance dated Mar. 22, 2017 in U.S. Appl. No. 14/772,264, Wu et al., § 371(c) date Dec. 28, 2015.

Office Action dated Mar. 8, 2017 in U.S. Appl. No. 15/185,754, Wu et al., filed Jun. 17, 2016.

Notice of Allowance dated Dec. 28, 2017, 2017 in U.S. Appl. No. 15/185,754, Wu et al., filed Jun. 17, 2016.

Office Action dated Feb. 21, 2018 in U.S. Appl. No. 15/511,946, Wu et al., 371(c) date Mar. 16, 2017.

Office Action dated Aug. 16, 2018 in U.S. Appl. No. 15/511,946, Wu et al., 371(c) date Mar. 16, 2017.

Akers, M. J., "Parenteral Preparations," in *Remington, The Science and Practice of Pharmacy*, Chapter 41, pp. 802-836, 21st Edition, Ed. Troy, D. B., Lippincott Williams & Wilkins, United States (2005).

Office Action dated Feb. 8, 2018 in U.S. Appl. No. 15/648,527, Wu et al., filed Jul. 13, 2017.

Notice of Allowance dated Jul. 12, 2018 in U.S. Appl. No. 15/648,527, Wu et al., filed Jul. 13, 2017.

Office Action dated Aug. 10, 2016 in U.S. Appl. No. 14/685,806, Wu et al., filed Apr. 14, 2015.

Notice of Allowance dated Apr. 19, 2017 in U.S. Appl. No. 14/685,806, Wu et al., filed Apr. 14, 2015.

Grodowska, K. and Parczewski, A., "Organic solvents in the pharmaceutical industry," *Acta poloniae pharmaceutica* 67(1):3-12, Polish Pharmaceutical Society, Poland (2010).

Partial Translation (pp. 124-126) of Yunosova, O.N., et al., "Selective alkylamination of 3,5-dihalo-6H-anthra[1 ,9-c,d]isoxazol-6-ones," *Izvest. Vys. Uceb. Zaved. Himia I Himi. Technol.* 47(8):124-127, Wiley-VCH Verlag GmbH & Co. KGaA, Weinheim, Germany (2004), Irina Knizhnik, USPTO, Alexandria, VA (Aug. 4, 2016).

U.S. Food and Drug Administration, "Dosage Form," CDER Data Element No. C-DRG-00201, CDER Approved Date Apr. 14, 1992, last updated Jan. 30, 2009, accessed at http://www.fda.gov/Drugs/DevelopmentApprovalProcess/FormsSubmissionRequirements/ElectronicSubmissions/DataStandardsManualmonographs/ucm071666.htm, accessed on Aug. 8, 2016, 21 pages.

International Search Report in International Application No. PCT/US2015/048123, ISA/US, Commissioner for Patents, Alexandria, Virginia, dated Dec. 4, 2015, 3 pages.

Written Opinion of the International Searching Authority in International Application No. PCT/US2015/048123, ISA/US, Commissioner for Patents, Alexandria, Virginia, dated Dec. 4, 2015, 8 pages.

Office Action dated Apr. 24, 2015 in U.S. Appl. No. 14/635,635, Wu et al., filed Mar. 2, 2015.

Office Action dated Nov. 13, 2015 in U.S. Appl. No. 14/635,635, Wu et al., filed Mar. 2, 2015.

Notice of Allowance dated Mar. 4, 2016 in U.S. Appl. No. 14/635,635, Wu et al., filed Mar. 2, 2015.

Office Action dated Apr. 18, 2013 in U.S. Appl. No. 13/133,565, Wu et al., § 371(c) date Aug. 29, 2011.

Office Action dated Oct. 18, 2013 in U.S. Appl. No. 13/133,565, Wu et al., § 371(c) date Aug. 29, 2011.

Office Action dated Feb. 7, 2014 in U.S. Appl. No. 13/133,565, Wu et al., § 371(c) date Aug. 29, 2011.

Notice of Allowance dated Feb. 12, 2015 in U.S. Appl. No. 13/133,565, Wu et al., § 371(c) date Aug. 29, 2011.

Notice of Allowance dated Jan. 9, 2019 in U.S. Appl. No. 15/511,946, Wu et al., 371(c) date Mar. 16, 2017.

* cited by examiner

COMPOSITIONS OF PROTEIN RECEPTOR TYROSINE KINASE INHIBITORS

CROSS-REFERENCE TO RELATED APPLICATION

This Application is a Continuation Application of U.S. patent application Ser. No. 13/133,565, which is a National Stage Application of International Application No. PCT/US2009/067197, filed on Dec. 8, 2009, which claims the benefit of priority to U.S. Provisional Patent Application No. 61/120,827, filed on Dec. 8, 2008, the entire contents of each of which are herein incorporated by reference in their entirety for all purposes.

Related U.S. patent application Ser. No. 14/256,094, filed on Apr. 18, 2014, which issued as U.S. Pat. No. 8,809,530, on Aug. 19, 2014, is a Divisional Application of U.S. patent application Ser. No. 13/133,565.

1. FIELD OF THE INVENTION

The present invention relates to synthetic substituted heterocyclic compounds and pharmaceutical compositions containing the same that are capable of inhibiting or antagonizing a family of receptor tyrosine kinases, Tropomyosin Related Kinases (Trk), in particular the nerve growth factor (NGF) receptor, TrkA. The invention further concerns the use of such compounds in the treatment and/or prevention of pain, cancer, restenosis, atherosclerosis, psoriasis, thrombosis, or a disease, disorder or injury relating to dysmyelination or demyelination or the disease or disorder associated with abnormal activities of NGF recptor TrkA.

2. BACKGROUND OF THE INVENTION

Trk family proteins are receptor tyrosine kinases composed of three family members, TrkA, TrkB and TrkC. They bind with high affinity to, and mediate the signal transduction induced by the Neurotrophin family of ligands whose prototype members are Nerve Growth Factor (NGF), Brain-Derived Neurotrophic Factor (BDNF) and Neurotrophin 3-5 (NT 3-5). In addition, a co-receptor lacking enzymatic activity, p75, has been identified which binds all neurotrophines (NTs) with low affinity and regulates neurotrophin signaling. A critical role of the Trks and their ligands during the development of the central and peripheral nervous systems have been established through gene disruption studies in mice. In particular, TrkA-NGF interaction was shown as a requirement for the survival of certain peripheral neuron populations involved in mediating pain signaling. It has been shown that increased expression of TrkA also correlates with an increased level of pain in the case of pancreatic cancer (Zhu, et al, Journal of clinical oncology, 17:2419-2428 (1999)). Increased expression of NGF and TrkA was also observed in human osteoarthritis chondrocytes (Iannone et al, Rheumatology 41:1413-1418 (2002)).

TrkA (Troponyosin-receptor kinase A) is a cell surface receptor kinase containing an extracellular, a transmembrane, and a cytoplasmic kinase domain. The binding of a neurotrophin triggers oligomerization of the receptors, phosphorylation of tyrosine residues in the kinase domain, and activation of intercellular signaling pathways, including Ras/MAPK cascade, PI3K/AKT, and IP3-dependent Ca2+ release. Tyrosine kinase activity is an absolute requirement for signal transduction through this class of receptor. NGF receptors have been also found on a variety of cell types outside of the nervous system. For example, TrkA has been also found on human monocytes, T- and B-lymphocytes and mast cells.

There are several examples of either ant-TrkA antibodies or anti-NGF antibodies known in the art. For example, PCT Publication Nos. WO 2006/131952, WO 2005/061540 and EP 1181318 disclose use of anti-TrkA antibodies as effective analgesics in in-vivo animal models of inflammatory and neuropathic pain. PCT Application Nos. WO 01/78698, WO 2004/058184 and WO 2005/019266 disclose the use of an NGF antagonist for preventing or treating pain. PCT Application WO 2004/096122 describes a method for the treatment or the prevention of pain with co-administration of an anti-NGF antibody and an opioid analgesic. PCT Application WO 2006/137106 discloses a method for the treatment or the prevention of pain with co-administration of an anti-TrkA antibody and an opioid analgesic. In addition, profound or significantly attenuated reduction of bone pain caused by prostate cancer metastasis has been achieved by utilization of an anti-NGF antibody (Sevik, M A, et al, Pain 115:128-141 (2005)).

Besides antibodies, however, few TrkA inhibitors are known and very few (if any) show high TrkA kinase selectivity (including staurosporine derived TrkA inhibitors, CEP-751 and CEP-701). It has been rarely (if any) known in the art that a synthetic organic molecule or compound had been used as either direct TrkA or NGF inhibitor or antagonist for treatment or prevention of pain in particular. It may due mainly to the facts of difficulty in identifying potent and particularly selective anti-TrkA or anti-NGF small organic compounds, though the crystal structure of NGF in complex with the TrkA receptor has been determined (Nature 401: 184-188 (1996) & 254:411(1991)).

The therapeutic implications of an effective Trk inhibitor may well go beyond pain therapy. The subversion of this receptor and its signaling pathway in certain malignancies has also been documented. The tyrosine kinase activity of Trk is believed to promote the unregulated activation of cell proliferation machinery. It is believed that inhibitors of TrkA, TrkB, or TrkC kinases, individually or in combination, have utility against some of the most common cancers such as brain, melanoma, multiple myeloma, squamous cell, bladder, gastric, pancreatic, breast, head, neck, esophageal, prostate, colorectal, lung, renal, ovarian, gynecological, thyroid cancer, and certain type of hematological malignancies. Lestaurtinib (CEP-701, Cephalon), an indolocarbazole inhibitor of several tyrosine kinases, including Flt-3 and TrkA, and CEP-751, a pan Trk inhibitor have been entered Phase II clinical trails for the treatment of acute myelogenous leukaemia (AML), pancreatic cancer and multiple myeloma (MM) and/or prostate cancer.

Of particular note are reports of aberrant expression of NGF and TrkA receptor kinase are implicated in the development and progression of human prostatic carcinoma and pancreatic ductal adrenocarcinoma and activating chromosomal rearrangements of Trks in acute myelogenous leukemia (AML), thyroid and breast cancers and receptor point mutations predicted to be constitutively activating in colon tumors. In addition to these activation mechanisms, elevated Trk receptor and ligand have also been reported in a variety of tumor types including multiple myeloma, melanoma, neuroblastoma, ovarian and pancreatic carcinoma. The neurotrophins and their corresponding Trk receptor subtypes have been shown to exert a variety of pleiotropic responses on malignant cells, including enhanced tumor invasiveness and chemotaxis, activation of apoptosis, stimulation of clonal growth, and altered cell morphology. These effects have been observed in carcinomas of the prostate, breast, thyroid, colon, malignant melanomas, lung carcinomas, glioblastomas, pancreatic carcinoids and a wide variety of pediatric and neuroectodermal-derived tumors including Wilm's tumor, neuroblastomas and medulloblastomas. Neurotrophins and their receptor subtypes have been implicated in these cancers either through autocrine or paracrine mechanisms involving carcinoma cells and the surrounding parenchymal and stromal tissues. Overall, the oncogenic properties of Trk signaling in multiple tumor types makes the modulation of the Trk receptor signaling a potentially attractive therapeutic intervention point in different malignancies.

Due to the therapeutic promise associated with inhibiting TrkA, and the relative lack of potent and selective inhibitors, it is great need to discover the potent and particular isoform selective TrkA inhibitors, especially of orally active small synthetic molecules for possible treatment or prevention of the disease or disorders associated with TrkA activity.

3. SUMMARY OF THE INVENTION

The object of the present invention is the use of a small synthetic molecule as NGF receptor TrkA inhibitor and/or antagonist for the preparation of a medicament for the treatment and/or prevention of diseases associated with inhibiting TrkA, which including pain, cancer, restenosis, atherosclerosis, psoriasis, thrombosis, or a disease, disorder or injury relating to dysmyelination or demyelination.

In one aspect, the present invention provides compounds having structural Formula (I):

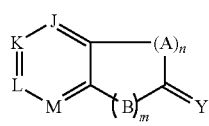

(I)

or a salt, solvate, or physiologically functional derivative thereof;
wherein:
n is 1, 2, or 3;
m is 0, 1, or 2;
A is C, N, O, S, NR$^1$, C=CR$^1$ (E and Z isomers), C=NR$^1$ (E and Z isomers), C(R$^1$R$^2$), CR$^1$=CR$^2$—CR$^{1\prime}$R$^{2\prime}$ (E and Z isomers), or CR$^1$=CR$^2$—NR$^{1\prime}$ (E and Z isomers);
when n is 2 or 3, any of two adjacent A, together with other atoms, form one or two rings where each of the rings is optionally substituted;
B is C, N, O, S, NR$^3$, or C(R$^3$R$^4$);
J, K, L, and M are independently N or CR$^5$;
Y is O, S, NR$^6$, or C(R$^6$R$^7$);
R$^1$, R$^2$, R$^3$, R$^4$, R$^5$, R$^6$, and R$^7$ are independently hydrogen, halogen, acyl, substituted acyl, alkoxycarbonyl, substituted alkoxycarbonyl, aryloxycarbonyl, substituted aryloxycarbonyl, —CONR$^8$R$^9$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl;
R$^8$ and R$^9$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^8$ and R$^9$, taken together with the nitrogen atom to which they are attached, form a 4-, 5-, 6-, or 7-membered cycloheteroalkyl ring, provided that both R$^8$ and R$^9$ are not hydrogen.

In another aspect, the present invention provides pharmaceutical compositions comprising one or more compounds as described above or a salt, solvate, or physiologically functional derivative thereof, and a pharmaceutically acceptable vehicle.

In still another aspect, the present invention provides methods for selectively inhibiting or antagonizing NGF receptor TrkA for treatment and/or prevention of pain, cancer, restenosis, atherosclerosis, psoriasis, thrombosis, or a disease, disorder or injury relating to dysmyelination or demyelination, with therapeutic effective amount of the compound as described above, or a salt, solvate, or physiologically functional derivative thereof.

In still another aspect, the present invention provides methods for treatment and/or prevention of pain, cancer, restenosis, atherosclerosis, psoriasis, thrombosis, or a disease, disorder or injury relating to dysmyelination or demyelination, with combination of (a) therapeutic effective amount of the compound as described above, or a salt, solvate, or physiologically functional derivative thereof, and (b) an opioid analgesic or at least one analgesic agent that acts by a mechanism different from a TrkA antagonist.

5. DETAILED DESCRIPTION OF THE INVENTION

The present invention relates to novel synthetic small molecules that act as inhibitors and/or antagonists of the members of Trk family protein kinases, in particularly the NGF receptor, TrkA.

5.1 Definitions

Terms used in the claims and specification are defined as set forth below unless otherwise specified.

The term "a compound of the present invention", "the compound of the present invention", "compounds of the present invention", or "the present compounds" refers to one or more compounds encompassed by the structural formulae and/or any subgeneric formulae disclosed herein and includes any specific compounds within these generic formula whose structure is disclosed herein. Compounds of the invention may contain one or more chiral centers and/or double bonds and therefore, may exist as stereoisomers, such as double-bond isomers (i.e., geometric isomers), the racemic mixtures, enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. The compounds of the invention may also exist in several tautomeric forms. Accordingly, the chemical structures depicted herein encompass all possible tautomeric forms of the illustrated compounds. Compounds also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{17}$O, $^{18}$O, etc. Compounds may exist in unsolvated forms as well as solvated forms, including hydrated forms and as N-oxides. In general, the salt, hydrated, solvated, and N-oxide forms are within the scope of the present invention. Certain compounds of the present invention may exist in multiple crystalline forms or an amorphous form. In general, all physical forms are equivalent for the uses contemplated by the present invention and are intended to be within the scope of the present invention.

The term "physiologically functional derivative(s)" used herein refers to any physiologically tolerated derivative of a compound of the present invention, for example, an ester or prodrug, which, upon administration to a mammal, e.g., a human, are transformed directly or indirectly to a compound of formula (Ia), (Ic), (Ii), (II), or an active metabolite thereof. Physiologically functional derivatives include prodrugs of the compounds of the present invention. Examples of prodrug are described in H. Okada et al., *Chem. Pharm. Bull.* 1994, 42, 57-61. Such prodrugs can be metabolized in vivo to a compound of the invention. These prodrugs may themselves be active or not.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is ($C_1$-$C_{20}$) alkyldiyl, more preferably, ($C_1$-$C_{10}$) alkyldiyl, most preferably, ($C_1$-$C_6$) alkyldiyl.

"Alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used.

"Acyl" by itself or as part of another substituent refers to a radical —C(O)$R^{200}$, where $R^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Amino" by itself or as part of another substituent refers to a radical —N$R^aR^b$, where $R^a$ and $R^b$ are independently hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein, or alternatively $R^a$ and $R^b$, taken together with the atoms to which they are bonded, form a cycloheteroalkyl ring. Representative examples include, but are not limited to —$NH_2$, —$NHCH_3$, —$N(CH_3)_2$, —NH-phenyl, —NH—$CH_2$-phenyl, pyrrolidine, and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_8$) alkyl and the aryl moiety is ($C_6$-$C_{10}$) aryl.

"Aryloxy," by itself or as part of another substituent, refers to a radical of the formula —O—$R^{201}$, where $R^{201}$ is aryl, substituted aryl, arylalkyl, or substituted arylalkyl.

"Aryloxycarbonyl," by itself or as part of another substituent, refers to a radical of the formula —C(O)—O—$R^{201}$, where $R^{201}$ is aryl, substituted aryl, arylalkyl, or substituted arylalkyl.

"Cycloalkyl" or "carbocyclyl" by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, a cycloalkyl group comprises from 3 to 10 ring atoms ($C_3$-$C_{10}$ cycloalkyl). In other embodiments, a cycloalkyl group comprises from 3 to 7 ring atoms ($C_3$-$C_7$ cycloalkyl).

"Cycloheteroalkyl" or "heterocyclyl" by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, B, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, borolane, dioxaborolane, and the like. In some embodiments, the cycloheteroalkyl group comprises from 3 to 10 ring atoms (3-10 membered cycloheteroalkyl). In other embodiments, the cycloalkyl group comprise from 5 to 7 ring atoms (5-7 membered cycloheteroalkyl).

A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Heteroalkyl, Heteroalkanyl, Heteroalkenyl, Heteroalkanyl, Heteroalkyldiyl and Heteroalkyleno" by themselves or as part of another substituent, refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —$NR^{203}R^{204}$—, =N—N=, —N=N—, —N=N—$NR^{205}R^{206}$, —$PR^{207}$—, —$P(O)_2$—, —$POR^{208}$—, —O—$P(O)_2$—, —SO—, —$SO_2$—, —$SnR^{209}R^{210}$—, $BR^{211}R^{212}$, $BOR^{213}OR^{214}$ and the like, where $R^{203}$, $R^{204}$, $R^{205}$, $R^{206}$, $R^{207}$, $R^{208}$, $R^{209}$, $R^{210}$, $R^{211}$, $R^{212}$, $R^{213}$ and $R^{214}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, -carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, furopyridine, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Heteroaryloxy," by itself or as part of another substituent, refers to a radical of the formula —O—$R^{201}$, where $R^{201}$ is heteroaryl, substituted heteroaryl, heteroarylalkyl, or substituted heteroarylalkyl.

"Heteroaryloxycarbonyl," by itself or as part of another substituent, refers to a radical of the formula —C(O)—O—$R^{201}$, where $R^{201}$ is heteroaryl, substituted heteroaryl, heteroarylalkyl, or substituted heteroarylalkyl.

"Modulating" refers to adjusting, varying, or changing. As used herein, modulation of calcium ion channel includes antagonizing, agonizing, or partially antagonizing. That is, the compounds of the present invention may act as antagonists, agonists, or partial antagonists of the calcium ion channel activity.

"Parent Aromatic Ring System" refers to an unsaturated cyclic or polycyclic ring system having a conjugated it electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, B, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Patient" or "subject" includes, but is not limited to animals such as, for example, mammals. Preferably, the patient is a human.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute, i.e., a compound of the present invention), or an aggregate that consists of a solute ion or molecule (the compound of the present invention) with one or more solvent molecules.

"Pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Prodrug or softdrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug or softdrug is an ester or an ether form of a pharmaceutically active compound. Several prodrugs have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these precursors, prodrugs or softdrugs with commonly employed techniques of organic synthesis.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =$O$, —$OR^b$, —$SR^b$, —$S^-$, =$S$, —$NR^cR^c$, =$NR^b$, =$N$—$OR^b$, trihalomethyl, —$CF_3$, —$CN$, —$OCN$, —$SCN$, —$NO$, —$NO_2$, =$N_2$, —$N_3$, —$S(O)_2R^b$, —$S(O)_2NR^b$, —$S(O)_2O$—, —$S(O)_2OR^b$, —$OS(O)_2R^b$, —$OS(O)_2O$—, —$OS(O)_2OR^b$, —$P(O)(O^-)_2$, —$P(O)(OR^b)$ ($O^-$), —$P(O)(OR^b)(OR^b)$, —$C(O)R^b$, —$C(S)R^b$, —$C(NR^b)$ $R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)$ $R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)$ $NR^cR^c$, where $R^a$ is selected from the group consisting of alkyl, substituted alkyl, arylalkyl, alkyldiyl, substituted alkyldiyl, aryl, substituted aryl, arylalkyl, substituted arylalkyl, heteroalkyl, substituted heteroalkyl, heteroalkyldiyl, substituted heteroalkyldiyl, heteroaryl, substituted heteroaryl, heteroarylalkyl substituted heteroarylalkyl; each $R^b$ is independently hydrogen or $R^a$; and each $R^c$ is independently $R^b$ or alternatively, the two $R^c$s are taken together with the nitrogen atom to which they are bonded form a cycloheteroalkyl ring which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —$CN$, —$OCN$, —$SCN$, —$NO$, —$NO_2$, —$N_3$, —$S(O)_2R^b$, —$S(O)_2O$—, —$S(O)_2OR^b$, —$OS(O)_2R^b$, —$OS(O)_2O$—, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)$ $O^-$, —$C(O)OR^b$, —$C(S)OR^b$, —$C(O)NR^cR^c$, —$C(NR^b)$ $NR^cR^c$, —$OC(O)R^b$, —$OC(S)R^b$, —$OC(O)O^-$, —$OC(O)$ $OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and Re are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —$CN$, —$NO$, —$NO_2$, —$S(O)_2R^b$, —$S(O)_2O$—, —$S(O)_2OR^b$, —$OS(O)_2R^b$, —$OS(O)_2O$—, —$OS(O)_2OR^b$, —$P(O)(O^-)_2$, —$P(O)(OR^b)(O^-)$, —$P(O)$ $(OR^b)(OR^b)$, —$C(O)R^b$, —$C(S)R^b$, —$C(NR^b)R^b$, —$C(O)$ $OR^b$, —$C(S)OR^b$, —$C(O)NR^cR^c$, —$C(NR^b)NR^cR^c$, —$OC$ $(O)R^b$, —$OC(S)R^b$, —$OC(O)OR^b$, —$OC(S)OR^b$, —$NR^bC$ $(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)$ $NR^cR^c$, where $R^a$, $R^b$ and Re are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Treating", "treat" or "treatment" of any disease or disorder refers, in some embodiments, to ameliorating or preventing the disease or disorder (i.e., arresting, preventing, holding or reducing the development of the disease or at least one of the clinical symptoms thereof). In other embodiments "treating", "treat" or "treatment" refers to ameliorating at least one physical parameter, which may not be discernible by the patient. In yet other embodiments, "treating", "treat" or "treatment" refers to inhibiting, or holding or preventing the progress of, the disease or disorder, either physically, (e.g., stabilization of a discernible symptom), physiologically, (e.g., stabilization of a physical parameter) or both. In yet other embodiments, "treating", "treat" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

The term "receptor" refers to a molecule or complex of molecules, typically (although not necessarily) a protein(s), that is specifically bound by one or more particular ligands. The receptor is said to be a receptor for such ligand(s). Ligand-receptor binding, in many instances, induces one or more biological responses. A "modulator" of a polypeptide is either an inhibitor or an enhancer of an action or function of the polypeptide. Similarly, a "modulator" of a signaling pathway is an inhibitor or enhancer of at least one function mediated by the signaling pathway. Aspects of modulators are defined below with respect to polypeptides; however, those of skill in the art readily appreciate that these definitions also apply to signaling pathways.

A "non-selective" modulator of a polypeptide is an agent that modulates other members of the same family of polypeptides at the concentrations typically employed for modulation of the particular polypeptide.

A "selective" modulator of a polypeptide significantly modulates the particular polypeptide at a concentration at which other members of the same family of polypeptides are not significantly modulated.

A modulator "acts directly on" a polypeptide when the modulator exerts its action by interacting directly with the polypeptide.

A modulator "acts indirectly on" a polypeptide when the modulator exerts its action by interacting with a molecule other than the polypeptide, which interaction results in modulation of an action or function of the polypeptide.

An "inhibitor" or "antagonist" of a polypeptide is an agent that reduces, by any mechanism, any action or function of the polypeptide, as compared to that observed in the absence (or presence of a smaller amount) of the agent. An inhibitor of a polypeptide can affect: (1) the expression, mRNA stability, protein trafficking, modification (e.g., phosphorylation), or degradation of a polypeptide, or (2) one or more of the normal action or functions of the polypeptide. An inhibitor of a polypeptide can be non-selective or selective. Preferred inhibitors (antagonists) are generally small molecules that act directly on, and are selective for, the target polypeptide.

A "reversible" inhibitor is one whose effects can be reversed (i.e., one that does not irreversibly inactivate the target polypeptide).

A "competitive" inhibitor of a polypeptide is one that competes for binding to the polypeptide with another component required for polypeptide function. For example, TrkA function requires the binding of ATP and substrate. Accordingly, a competitive inhibitor of TrkA can act, for example, by binding at the ATP or substrate binding sites. This inhibition is generally reversible by increasing the concentration of ATP or substrate to the reaction mixture. Such an inhibitor is said to inhibit TrkA competitively with respect to ATP or substrate, respectively.

A "non-competitive" inhibitor of a polypeptide generally binds the polypeptide at a site other than the binding site of another component required for polypeptide function. This inhibition cannot be reversed by increasing the concentration of component(s) required for polypeptide function.

As used herein, an "allosteric modulator" of an polypeptide, typically an enzyme or receptor, is a modulator that binds at a location other than the active site of the target polypeptide, altering activity by inducing an allosteric change in the shape of the target polypeptide.

The terms "polypeptide" and "protein" are used interchangeably herein to refer a polymer of amino acids, and unless otherwise limited, include atypical amino acids that can function in a similar manner to naturally occurring amino acids.

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

The phrases "an effective amount" and "an amount sufficient to" refer to amounts of a biologically active agent that produce an intended biological activity.

The term "co-administer" or "co-administering" when used in reference to the administration of Trk (i.e., TrkA) antagonists and other agents indicates that the antagonist and other agent(s) are administered in a coordinated fashion so that there is at least some chronological overlap in their physiological activity on the subject. Thus, a TrkA antagonist can be administered simultaneously and/or sequentially with another agent. In sequential administration, there may even be some substantial delay (e.g., minutes or even hours or days) before administration of the second agent as long as the first administered agent is exerting some physiological effect on the organism when the second administered agent is administered or becomes active in the subject.

The term "reducing pain," as used herein, refers to decreasing the level of pain a subject perceives relative to the level of pain the subject would have perceived were it not for the intervention. Where the subject is a person, the level of pain the person perceives can be assessed by asking him or her to describe the pain or compare it to other painful experiences. Alternatively, pain levels can be determined by measuring the subject's physical responses to the pain, such as the release of stress-related factors or the activity of pain-transducing nerves in the peripheral nervous system or the CNS. One can also determine pain levels by measuring the amount of a well-characterized analgesic required for a person to report that no pain is present or for a subject to stop exhibiting symptoms of pain. A reduction in pain can also be measured as an increase in the threshold at which a subject experiences a given stimulus as painful. In certain embodiments, a reduction in pain is achieved by decreasing "hyperalgesia," the heightened sensitivity to a noxious stimulus, and such inhibition can occur without impairing "nociception," the subject's normal sensitivity to a "noxious" stimulus.

As used with reference to pain reduction, "a subject in need thereof" refers to an animal or person, preferably a person, expected to experience pain in the near future. Such animal or person may have an ongoing condition that is causing pain currently and is likely to continue to cause pain. Alternatively, the animal or person has been, is, or will be enduring a procedure or event that usually has painful consequences. Chronic painful conditions such as diabetic neuropathic hyperalgesia and collagen vascular diseases are examples of the first type; dental work, particularly that accompanied by inflammation or nerve damage, and toxin exposure (including exposure to chemotherapeutic agents) are examples of the latter type.

"Inflammatory pain" refers to pain arising from inflammation. Inflammatory pain often manifests as increased sensitivity to mechanical stimuli (mechanical hyperalgesia or tenderness). For examples, inflammatory pain is due to a condition selected from the group consisting of: burn, sunburn, arthritis, colitis, carditis, dermatitis, myositis, neuritis, mucositis, urethritis, cystitis, gastritis, pneumonitis, and collagen vascular disease.

"Neuropathic pain" refers to pain arising from conditions or events that result in nerve damage. "Neuropathy" refers to a disease process resulting in damage to nerves. "Causalgia" denotes a state of chronic pain following nerve injury. "Allodynia" refers to a condition in which a person experiences pain in response to a normally nonpainful stimulus, such as a gentle touch. For examples, neuropathic pain is due to a condition selected from the group consisting of: causalgia, diabetes, collagen vascular disease, trigeminal neuralgia, spinal cord injury, brain stem injury, thalamic pain syndrome, complex regional pain syndrome type I/reflex sympathetic dystrophy, Fabry's syndrome, small fiber neuropathy, cancer, cancer chemotherapy, chronic alcoholism, stroke, abscess, demyelinating disease, viral infection, antiviral therapy, AIDS, and AIDS therapy. Neuropathic pain is due to an agent selected from the group consisting of: trauma, surgery, amputation, toxin, and chemotherapy.

As used herein, the term "generalized pain disorder" refers to a group of idiopathic pain syndromes (e.g., fibromyalgia, irritable bowel syndrome, and temporomandibular disorders), for which the pathogenic mechanism is currently unknown, characterized by diffuse or generalized pain, and for which a diagnosis of inflammation or neuropathy as the direct cause of pain is excluded.

An "analgesic agent" refers to a molecule or combination of molecules that causes a reduction in pain.

The difference between "acute" and "chronic" pain is one of timing: acute pain is experienced soon (e.g., generally within about 48 hours, more typically within about 24 hours, and most typically within about 12 hours) after the occurrence of the event (such as inflammation or nerve injury) that led to such pain. By contrast, there is a significant time lag between the experience of chronic pain and the occurrence of the event that led to such pain. Such time lag is generally at least about 48 hours after such event, more typically at least about 96 hours after such event, and most typically at least about one week after such event.

The phrase "a drug-related effect" refers to an in vivo effect that occurs in response to a drug. Exemplary effects include stimulant, sedative, hypnotic, and ataxic effects.

A "sedative effect" refers to a decrease in activity and/or excitement in a subject. A "hypnotic effect" includes an increase in drowsiness and/or a facilitation of the onset and/or maintenance of sleep.

An "ataxic effect" refers to a decrease in motor coordination.

The term "maladaptive substance use" refers to the use of any substance that results in adverse consequences for the user that outweigh any benefits derived from the substance. Substances that are used in a maladaptive manner are generally consumed or administered (usually self-administered) to the body, by any route of administration, to produce an effect on the body that the user generally experiences as pleasurable. The substance can be a single substance (cocaine, for example) or a type of substance (e.g., food, in general). The adverse consequences can include, for example, adverse effects on health, the ability to care for oneself, the ability to form and maintain human relationships, and/or the ability to work. The adverse consequences are generally significant enough that the user would like to control, reduce, or end substance use or, alternatively, the user's family members and/or friends would like to see the user control, reduce, or end substance use. Maladaptive substance use can include uncontrollable craving for the substance; substance dependence, including psychological and/or physical dependence; and maladaptive substance use; as well as any of the individual symptoms of substance dependence and/or abuse listed below.

"Substance abuse" includes a maladaptive pattern of substance use leading to clinically significant impairment or distress, as manifested by one (or more) of the following, occurring within a 12-month period: (1) recurrent substance use resulting in a failure to fulfill major role obligations at work, school, or home (e.g., repeated absences or poor work performance related to substance use; substance-related absences, suspensions, or expulsions from school; neglect of children or household); (2) recurrent substance use in situations in which it is physically hazardous (e.g., driving an automobile or operating a machine when impaired by substance use); (3) recurrent substance-related legal problems (e.g., arrests for substance-related disorderly conduct); and (4) continued substance use despite having persistent or recurrent social or interpersonal problems caused or exacerbated by the effects of the substance (e.g., arguments with spouse about consequences of intoxication, physical fights). (See *American Psychiatric Association, Diagnostic Criteria for DSM-IV*, Washington D.C., APA, 1994.)

A "drug of abuse" includes any substance, the excessive consumption or administration of which can result in a diagnosis of substance dependence or abuse as defined herein or as defined by the current DSM Criteria promulgated by the American Psychiatric Association or equivalent criteria. Drugs of abuse include, without limitation, an opioid, a psychostimulant, a cannabinoid, an empathogen, a dissociative drug, and ethanol. Thus, for example, heroin, cocaine, methamphetamines, cannabis, 3-4 methylenedioxy-methamphetamine (MDMA), barbiturates, phencyclidine (PCP), ketamine, and ethanol are all drugs of abuse, as defined herein.

A "neuroleptic" refers to a class of tranquilizing drugs, used to treat psychotic conditions, that modulate neurotransmitter activity in the central nervous system and can act by modulating acetylcholine, dopamine, norepinephrine, serotonin, or γ-aminobutyric acid (GABA) transmission.

The term "neurosteroid" refers to a class of steroids, the natural forms of which are produced by cells of the central or peripheral nervous systems, independently of the steroidogenic activity of the endocrine glands. Neurosteroids are derived from cholesterol, and examples of neurosteroids include 3α,5α-tetrahydroprogesterone, 3α,5β-tetrahydroprogesterone, and 3α,5α-tetrahydrodeoxycorticosterone. For examples, ganaxalone and alphaxalone.

A "benzodiazepine" is referred to a agent selected from the group consisting of: alprazolam, chlordiazepoxide, chlordiazepoxide hydrochloride, chlormezanone, clobazam, clonazepam, clorazepate dipotassium, diazepam, droperidol, estazolam, fentanyl citrate, flurazepam hydrochloride, halazepam, lorazepam, midazolam hydrochloride, oxazepam, prazepam, quazepam, temazepam, and triazolam.

A "barbiturate" referred to a agent selected from the group consisting of: amobarbital, amobarbital sodium, aprobarbital, butabarbital sodium, hexobarbital sodium, mephobarbital, metharbital, methohexital sodium, pentobarbital, pentobarbital sodium, phenobarbital, phenobarbital sodium, secobarbital, secobarbital sodium, talbutal, thiamylal sodium, and thiopental sodium.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The term "cancer" refers to or describes the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

It is to be understood that this invention is not limited to particular methods, reagents, compounds, compositions, or biological systems, which can, of course, vary. It is also to be understood that the terminology used herein is for the purpose of describing particular aspects only, and is not intended to be limiting. As used in this specification and the appended claims, the singular forms "a", "an", and "the" include plural referents unless the content clearly dictates otherwise. Thus, for example, reference to "a compound" includes a combination of two or more compounds or molecules, and the like.

5.2 Compounds

In one aspect, the present invention provides a compound having a structural formula (I):

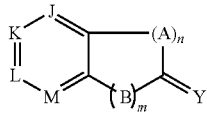
(I)

or a salt, solvate, or physiologically functional derivative thereof;
wherein:
n is 1, 2, or 3;
m is 0, 1, or 2;
A is C, N, O, S, NR$^1$, C=CR$^1$ (E and Z isomers), C=NR$^1$ (E and Z isomers), C(R$^1$R$^2$),
CR$^1$=CR$^2$—CR$^1$R$^{2'}$ (E and Z isomers), or CR$^1$=CR$^2$—NR$^{1'}$ (E and Z isomers);
when n is 2 or 3, any of two adjacent A, together with other atoms, form one or two rings
where each of the rings is optionally substituted;
B is C, N, O, S, NR$^3$, or C(R$^3$R$^4$);
J, K, L, and M are independently N or CR$^5$;
Y is O, S, NR$^6$, or C(R$^6$R$^7$);
R$^1$, R$^2$, R$^3$, R$^4$, R$^5$, R$^6$, and R$^7$ are each independently hydrogen, halogen, acyl, substituted acyl, alkoxycarbonyl, substituted alkoxycarbonyl, aryloxycarbonyl, substituted aryloxycarbonyl, —CONR$^8$R$^9$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
R$^8$ and R$^9$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^8$ and R$^9$, taken together with the nitrogen atom to which they are attached, form a 4-, 5-, 6-, or 7-membered cycloheteroalkyl ring, provided that both R$^8$ and R$^9$ are not hydrogen.

In one embodiment of formula (I), wherein m=0, n=1, and A=A$_1$-X$_1$.

In one embodiment of formula (I), the compound having structural formula (II):

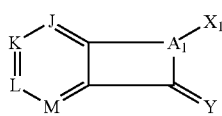
(II)

or a salt, solvate, or physiologically functional derivative thereof;
wherein:
A$_1$-X$_1$ is NR$^1$, C=CR$^1$ (E and Z isomers), C=NR$^1$ (E and Z isomers), or C(R$^1$R$^2$).

In one embodiment of formula (II), the compound having a structure selected from the group consisting of:

TABLE 1.1

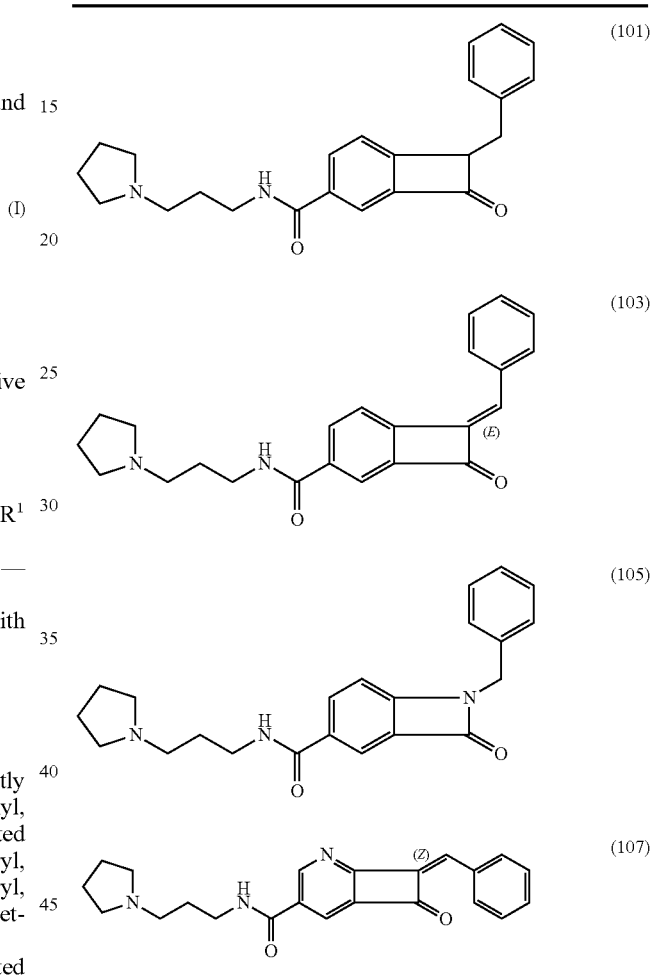

Compounds listed in Table 1.1 may also be represented by their chemical names as follows:

| ID | IUPAC Name |
|---|---|
| 101 | 7-benzyl-8-oxo-N-[3-(pyrrolidin-1-yl)propyl]bicyclo[4.2.0]octa-1,3,5-triene-3-carboxamide |
| 103 | (7E)-7-benzylidene-8-oxo-N-[3-(pyrrolidin-l-yl)propyl]bicyclo[4.2.0]octa-1,3,5-triene-3-carboxamide |
| 105 | 7-benzyl-8-oxo-N-[3-(pyrrolidin-1-yl)propyl]-7-azabicyclo[4.2.0]octa-1,3,5-triene-3-carboxamide |
| 107 | (8Z)-8-benzylidene-7-oxo-N-[3-(pyrrolidin-l-yl)propyl]-2-azabicyclo[4.2.0]octa-1,3,5-triene-4-carboxamide |

In one embodiment of formula (I), wherein m=1, n=1, and A=A$_2$-X$_2$.

In one embodiment of formula (I), the compound having a structural formula (III):

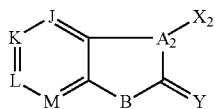
(III)

or a salt, solvate, or physiologically functional derivative thereof;

wherein:

$A_2$-$X_2$ is $NR^1$, $C=CR^1$ (E and Z isomers), $C=NR^1$ (E and Z isomers), or $C(R^1R^2)$.

In one embodiment of formula (III), the compound having a structure selected from the group consisting of:

TABLE 1.2

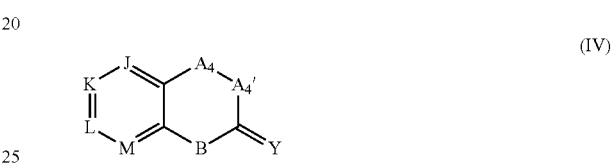

Compounds listed in Table 1.2 may also be represented by their chemical names as follows:

| ID | IUPAC Name |
|---|---|
| 109 | 4-{[1-(2-fluorobenzyl)-2-oxo-2,3-dihydro-1H-indol-3-yl]methyl}-N-[3-(pyrrolidin-1-yl)propyl]benzamide |
| 111 | 4-{(E)-[5-(2-fluorobenzyl)-6-oxo-5,6-dihydro-7H-pyrrolo[3,2-d]pyrimidin-7-ylidene]methyl}-N-[3-(pyrrolidin-1-yl)propyl]benzamide |
| 113 | 4-{(Z)-[1-(2-fluorobenzyl)-2-oxo-1,2-dihydro-3H-indol-3-ylidene]methyl}-N-[3-(pyrrolidin-1-yl)propyl]benzamide |
| 115 | 4-{[(3E)-1-(2-fluorobenzyl)-2-oxo-1,2-dihydro-3H-indol-3-ylidene]amino}-N-[3-(pyrrolidin-1-yl)propyl]benzamide |
| 117 | 4-{[(3Z)-1-(2-fluorobenzyl)-2-oxo-1,2-dihydro-3H-indol-3-ylidene]amino}-N-[3-(pyrrolidin-1-yl)propyl]benzamide |

In one embodiment of formula (I), wherein m=1, n=2, $A=Z_1$ and A is represent by $A_4$-$A_4'$.

In one embodiment of formula (I), the compound having a structural formula (IV):

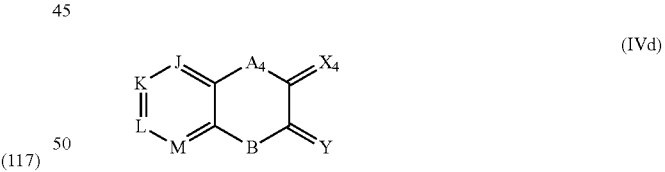
(IV)

or a salt, solvate, or physiologically functional derivative thereof;

wherein:

$A_4$ and $A_4'$ are independently selected from $NR^1$, $C=CR^1$ (E and Z isomers), $C=NR^1$ (E and Z isomers), or $C(R^1R^2)$; or alternatively, $A_4$ and $A_4'$, together with other atoms, form a ring which is optionally substituted; and the link between $A_4$ and $A_4'$ can be either single or double bond. The ring formed by $A_4$ and $A_4'$ with other atoms may be four-, five-, six-, seven-, or eight-membered carbocyclic or heterocyclic ring.

In one embodiment of formula (IV), wherein $A_4'$ is $C=X_4$ and the link between $A_4$ and $A_4'$ is a single bond.

In one embodiment of formula (IV), the compound having a structural formula (IVd):

(IVd)

or salt, solvate, or physiologically functional derivative thereof, wherein:

$A_4$ and $X_4$ are independently $CR^{11}R^{12}$ or $NR^{11}$;

$C=X_4$ can be either E and Z isomers;

$R^{11}$ and $R^{12}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl.

In one embodiment, wherein the compound having a structural formula (IVd) is selected from the group consisting of:

TABLE 1.3
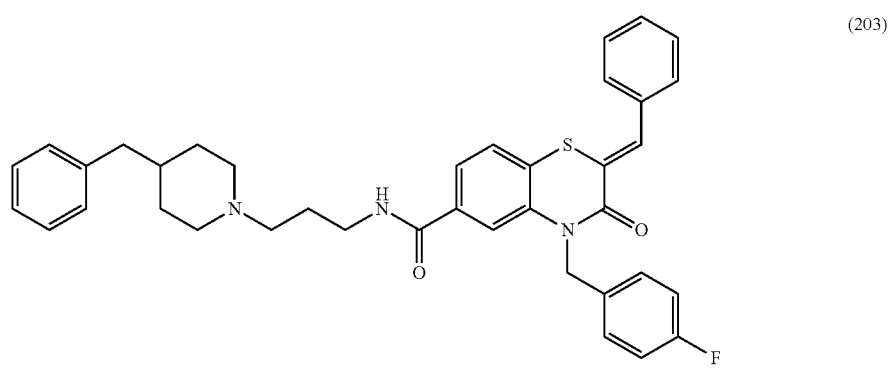
(203)
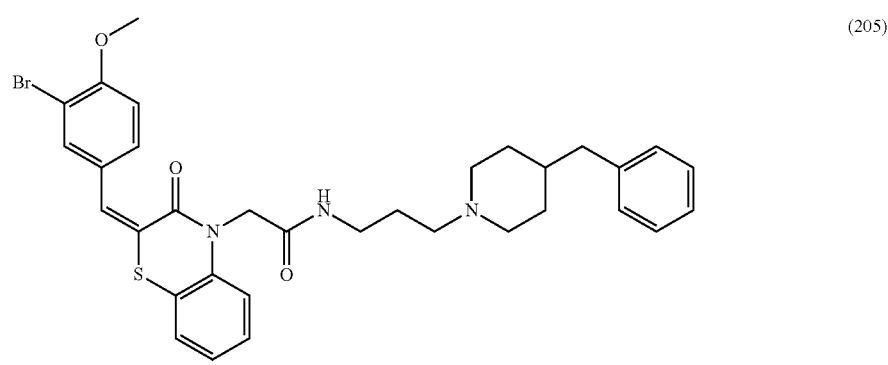
(205)
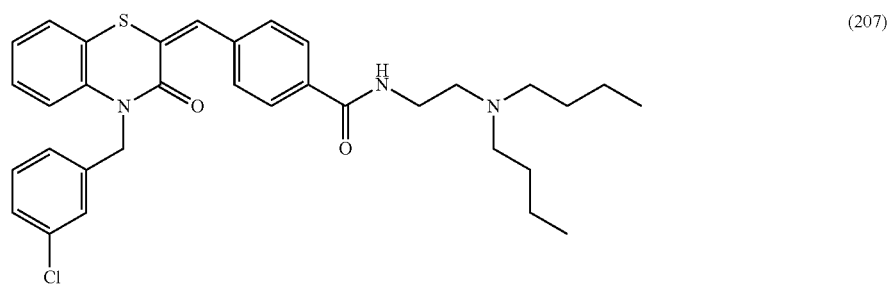
(207)
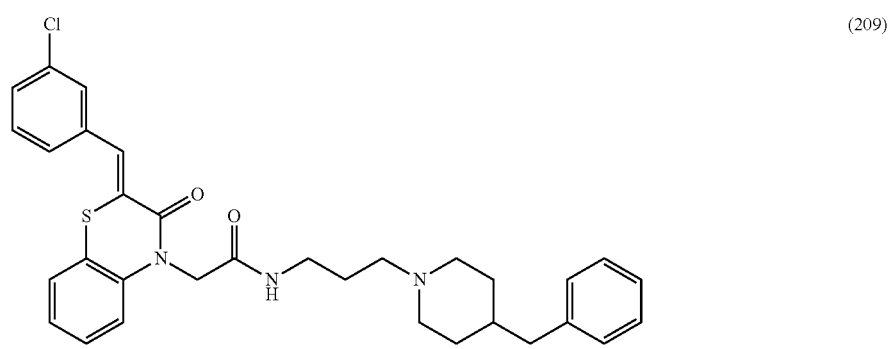
(209)

TABLE 1.3-continued
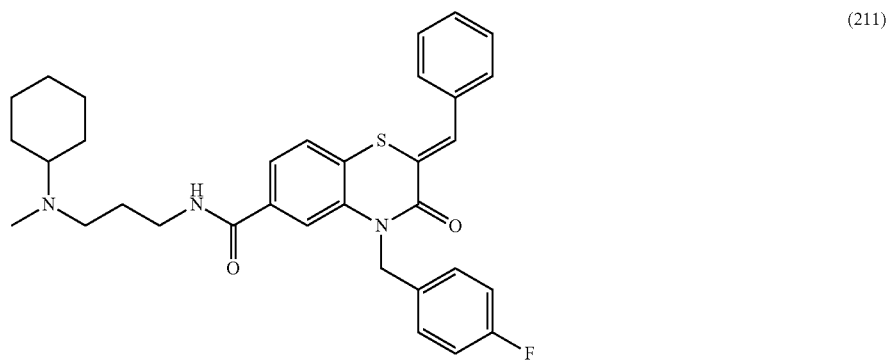
(211)
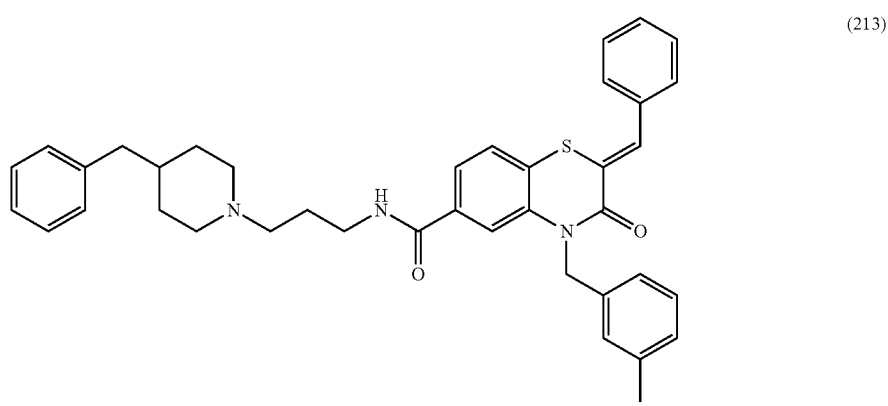
(213)
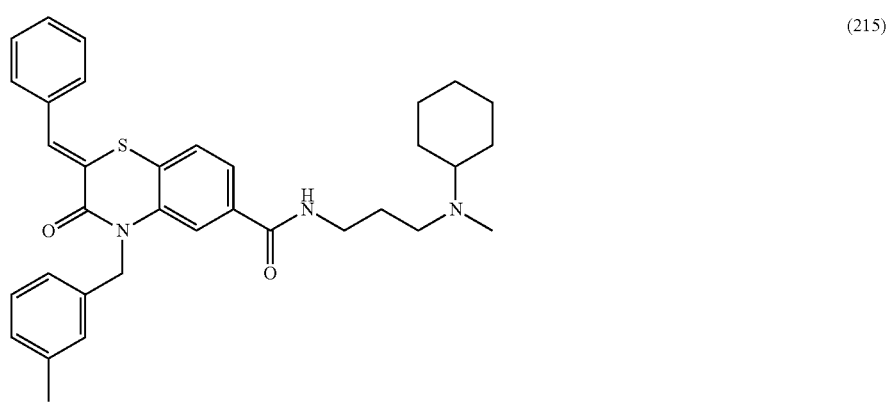
(215)
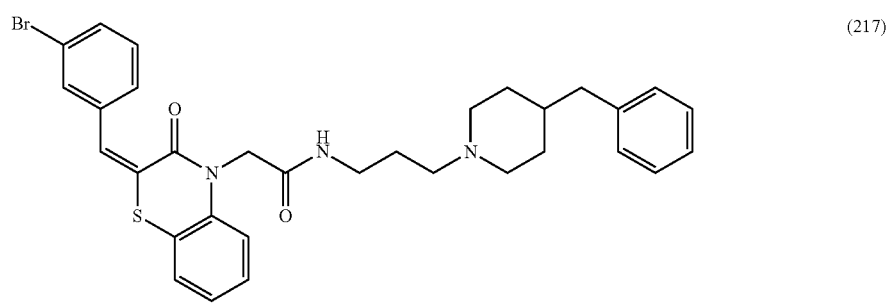
(217)

TABLE 1.3-continued
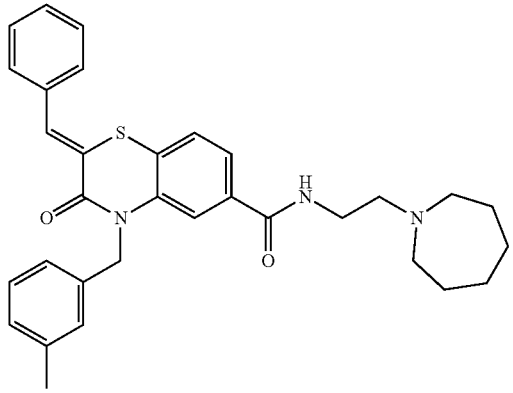 [SMILES: Cc1cccc(CN2C(=O)/C(=C/c3ccccc3)Sc3ccc(C(=O)NCCN4CCCCCC4)cc32)c1]
(219)
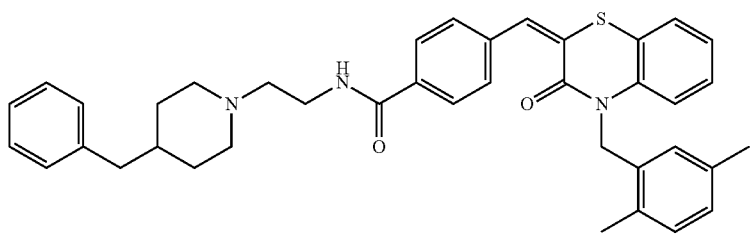 [SMILES: Cc1ccc(C)c(CN2C(=O)/C(=C\c3ccc(C(=O)NCCN4CCC(Cc5ccccc5)CC4)cc3)Sc3ccccc32)c1]
(221)
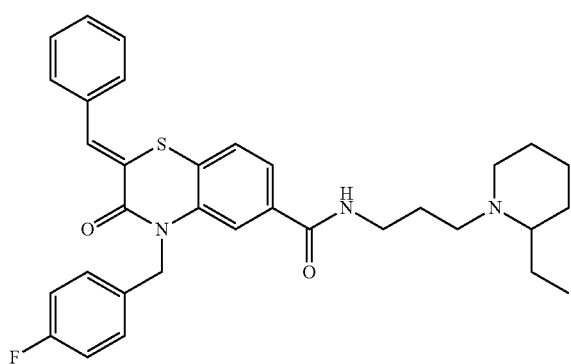 [SMILES: CCC1CCCCN1CCCNC(=O)c1ccc2c(c1)N(Cc1ccc(F)cc1)C(=O)/C(=C/c1ccccc1)S2]
(223)
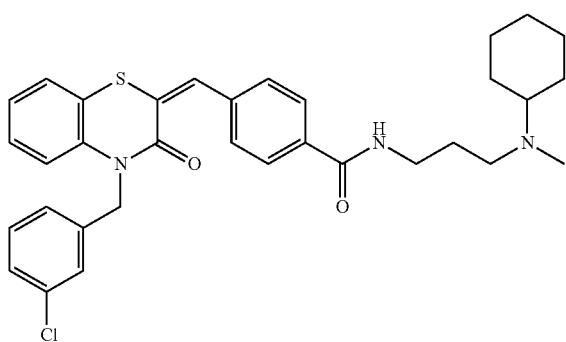 [SMILES: CN(CCCNC(=O)c1ccc(/C=C2/Sc3ccccc3N(Cc3cccc(Cl)c3)C2=O)cc1)C1CCCCC1]
(225)

TABLE 1.3-continued
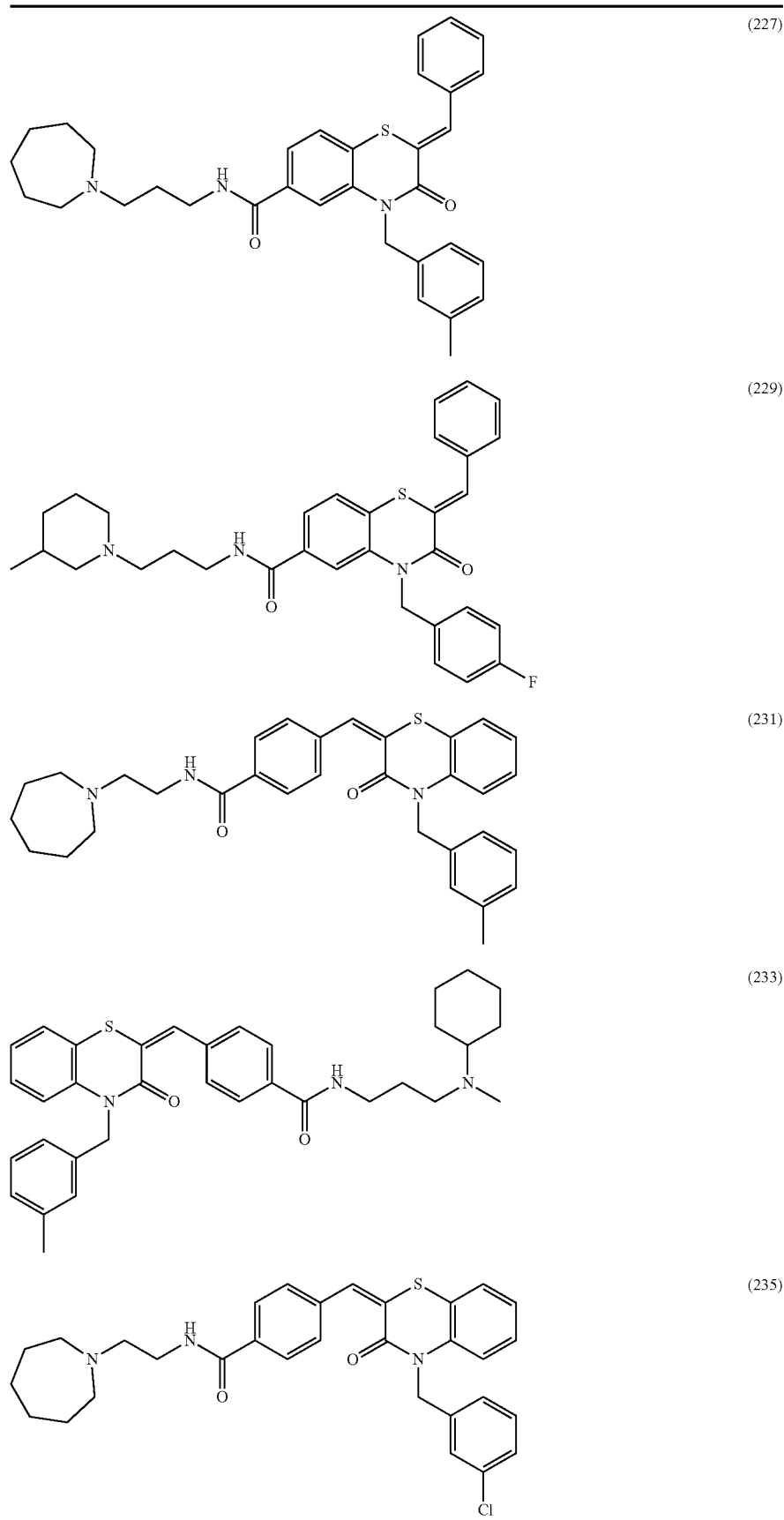

TABLE 1.3-continued
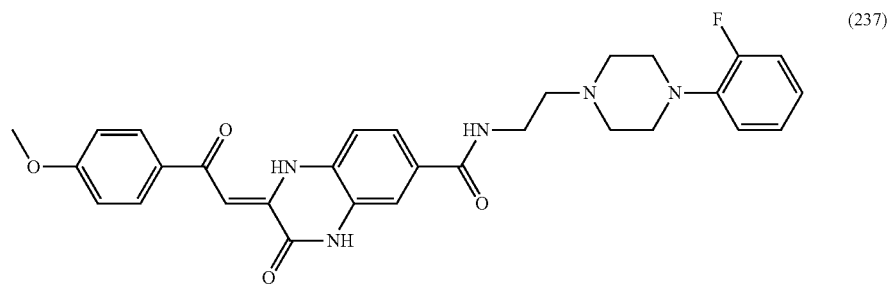
(237)
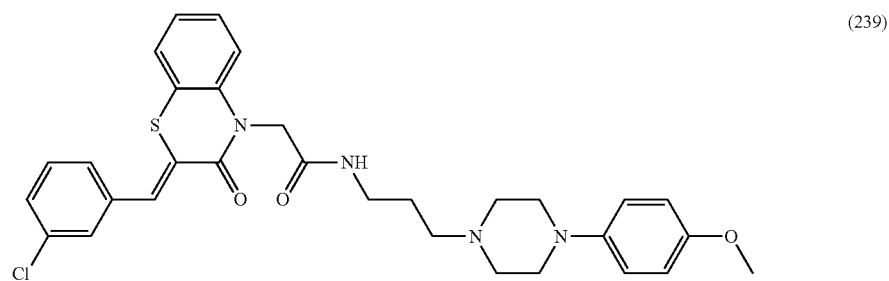
(239)
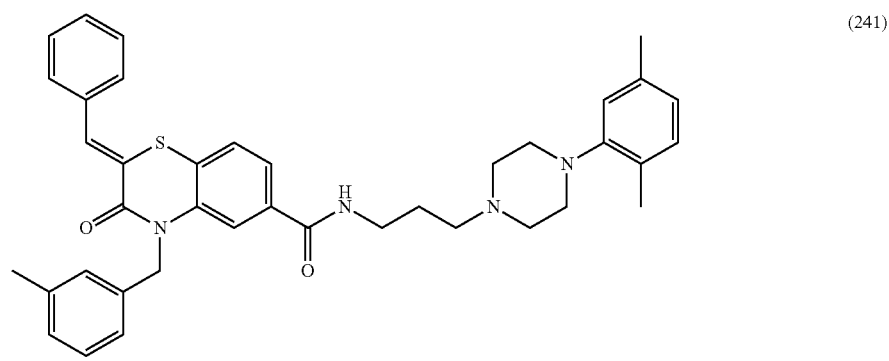
(241)
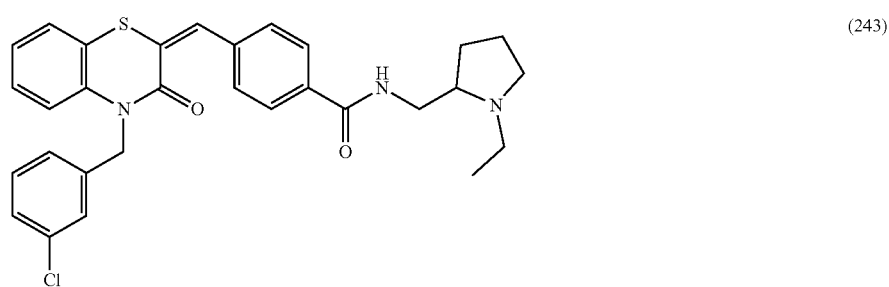
(243)
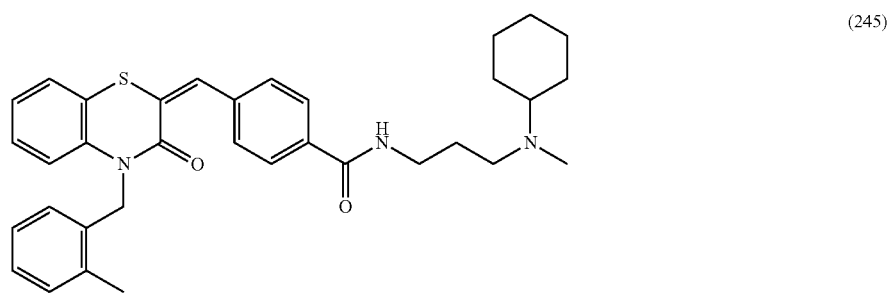
(245)

TABLE 1.3-continued
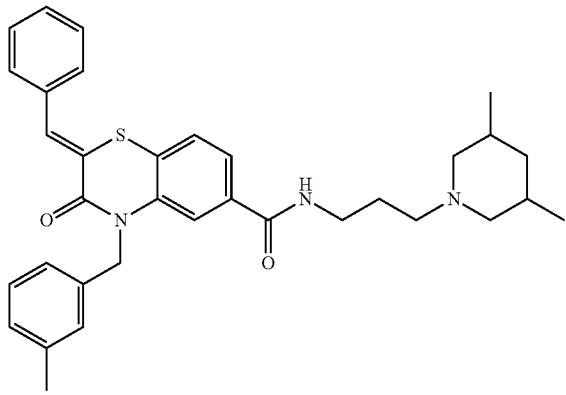 [SMILES: Cc1cccc(CN2C(=O)/C(=C/c3ccccc3)Sc3ccc(C(=O)NCCCN4CC(C)CC(C)C4)cc32)c1]
(247)
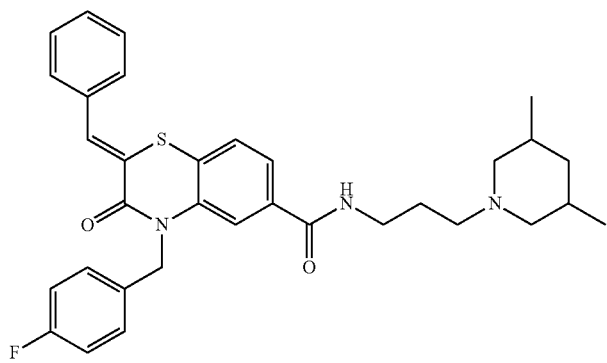 [SMILES: CC1CC(C)CN(CCCNC(=O)c2ccc3c(c2)N(Cc2ccc(F)cc2)C(=O)/C(=C/c2ccccc2)S3)C1]
(249)
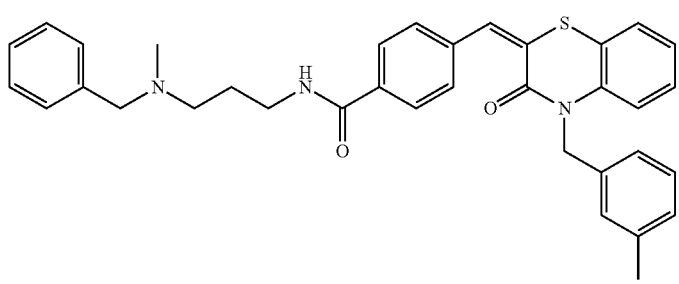 [SMILES: Cc1cccc(CN2C(=O)/C(=C\c3ccc(C(=O)NCCCN(C)Cc4ccccc4)cc3)Sc3ccccc32)c1]
(251)
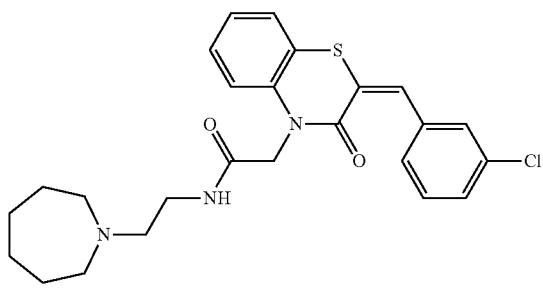 [SMILES: O=C(CN1C(=O)/C(=C\c2cccc(Cl)c2)Sc2ccccc21)NCCN1CCCCCC1]
(253)

TABLE 1.3-continued
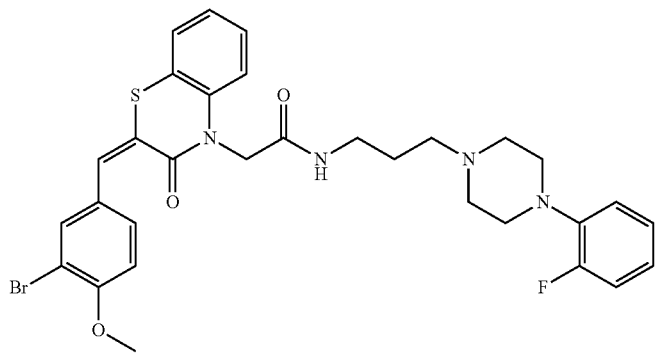 [SMILES: COc1ccc(/C=C2/Sc3ccccc3N(CC(=O)NCCCN3CCN(c4ccccc4F)CC3)C2=O)cc1Br]
(255)
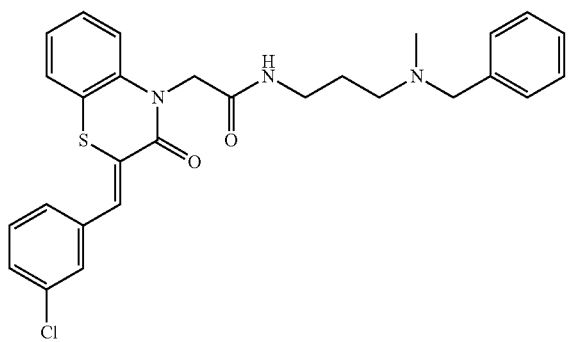 [SMILES: CN(CCCNC(=O)CN1C(=O)/C(=C/c2cccc(Cl)c2)Sc2ccccc21)Cc1ccccc1]
(257)
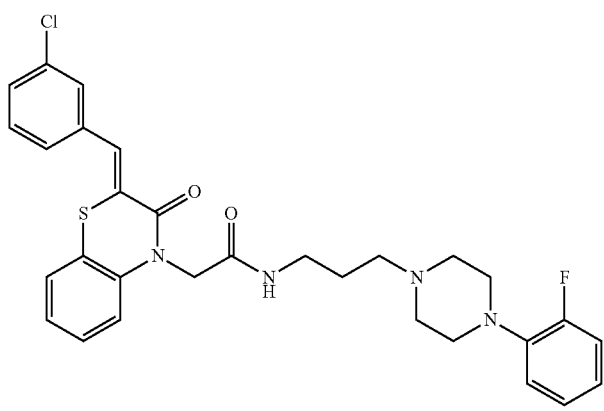 [SMILES: O=C(CN1C(=O)/C(=C/c2cccc(Cl)c2)Sc2ccccc21)NCCCN1CCN(c2ccccc2F)CC1]
(259)
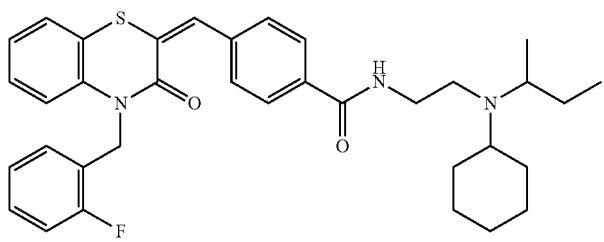 [SMILES: CCC(C)N(CCNC(=O)c1ccc(/C=C2/Sc3ccccc3N(Cc3ccccc3F)C2=O)cc1)C1CCCCC1]
(261)
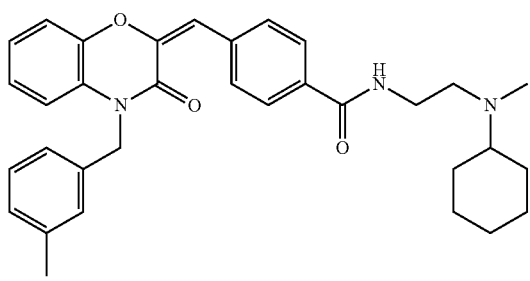 [SMILES: Cc1cccc(CN2C(=O)/C(=C\c3ccc(C(=O)NCCN(C)C4CCCCC4)cc3)Oc3ccccc32)c1]
(263)

TABLE 1.3-continued
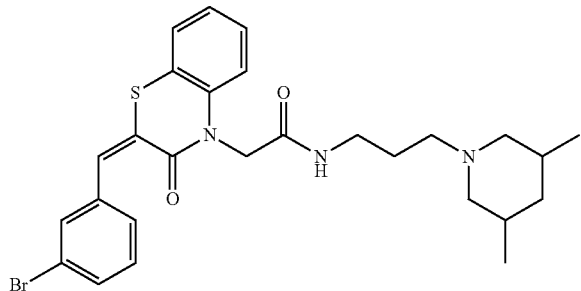
(265)
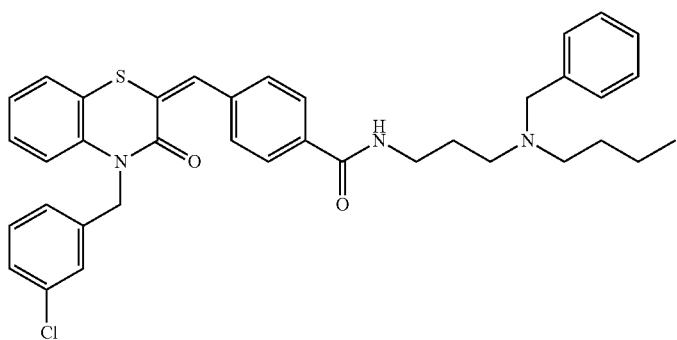 [SMILES: CCCCN(CCCNC(=O)c1ccc(/C=C2/Sc3ccccc3N(Cc3cccc(Cl)c3)C2=O)cc1)Cc1ccccc1]
(267)
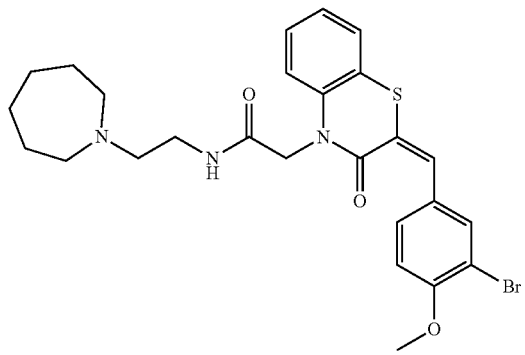 [SMILES: COc1ccc(/C=C2/Sc3ccccc3N(CC(=O)NCCN3CCCCCC3)C2=O)cc1Br]
(269)
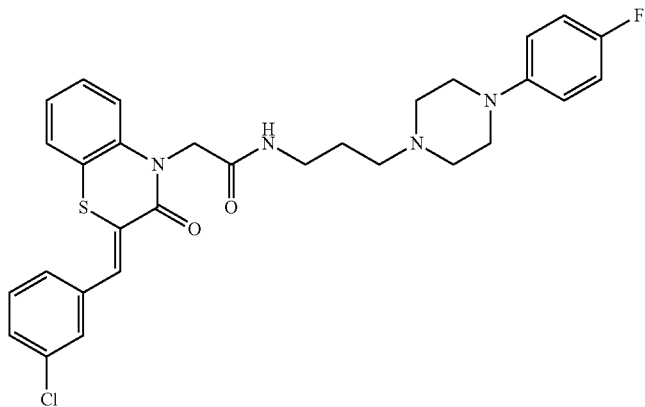 [SMILES: O=C(CN1C(=O)/C(=C/c2cccc(Cl)c2)Sc2ccccc21)NCCCN1CCN(c2ccc(F)cc2)CC1]
(271)

TABLE 1.3-continued
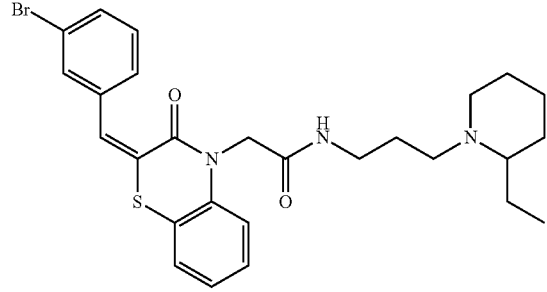
(273)
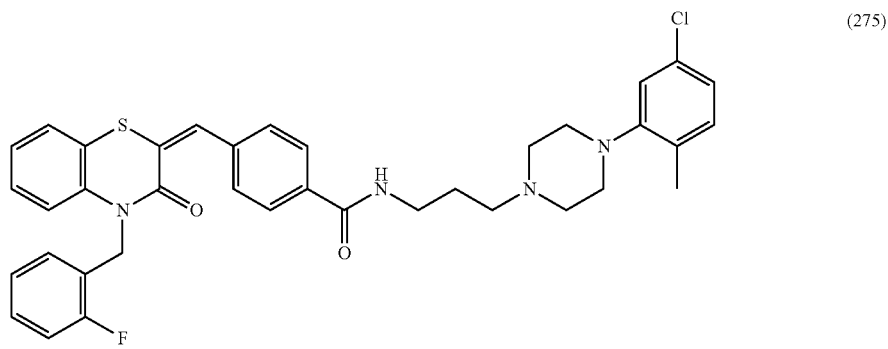
(275)
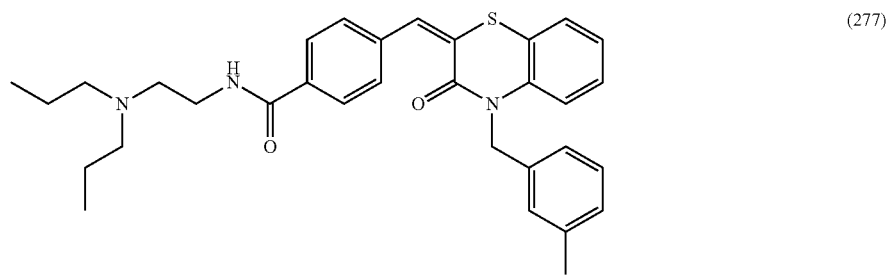
(277)
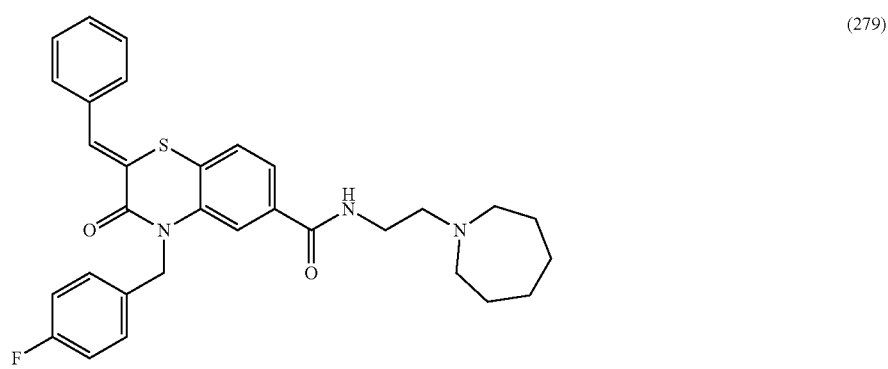
(279)
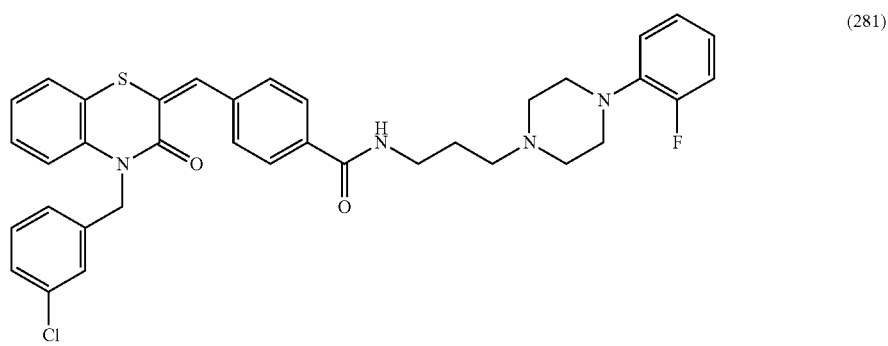
(281)

TABLE 1.3-continued
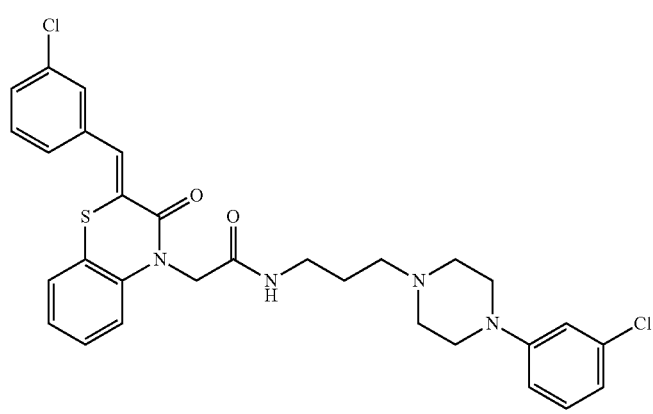 [SMILES: O=C(CN1C(=O)/C(=C/c2cccc(Cl)c2)Sc2ccccc21)NCCCN1CCN(c2cccc(Cl)c2)CC1]
(283)
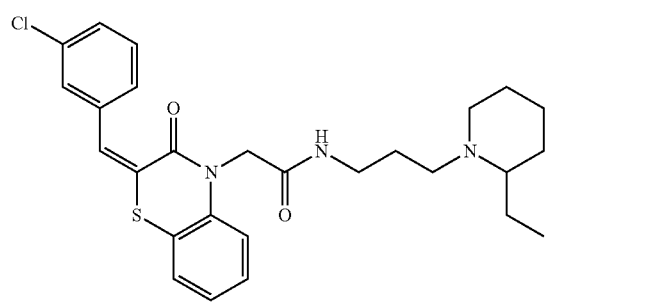 [SMILES: CCC1CCCCN1CCCNC(=O)CN1C(=O)/C(=C\c2cccc(Cl)c2)Sc2ccccc21]
(285)
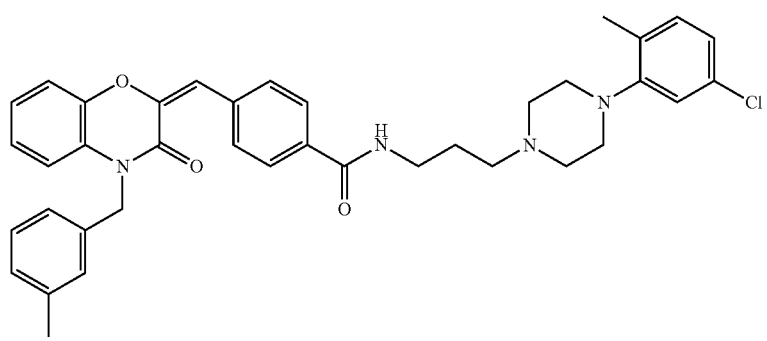 [SMILES: Cc1cccc(CN2C(=O)/C(=C\c3ccc(C(=O)NCCCN4CCN(c5cc(Cl)ccc5C)CC4)cc3)Oc3ccccc32)c1]
(287)
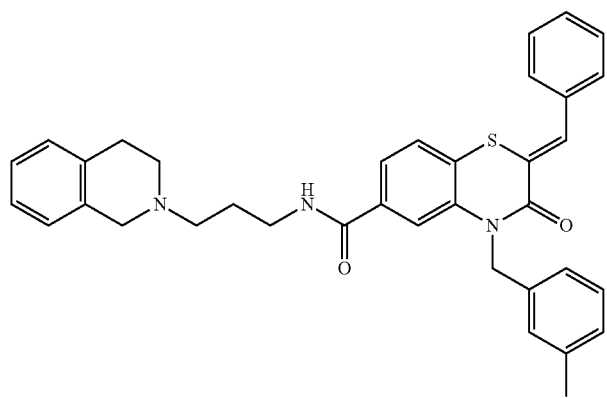 [SMILES: Cc1cccc(CN2C(=O)/C(=C/c3ccccc3)Sc3ccc(C(=O)NCCCN4CCc5ccccc5C4)cc32)c1]
(291)

TABLE 1.3-continued
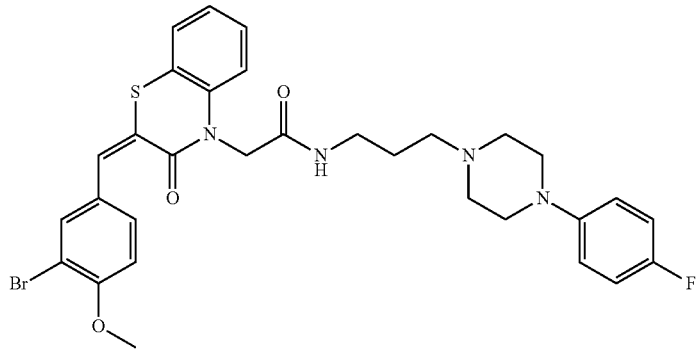 [SMILES: COc1ccc(/C=C2/Sc3ccccc3N(CC(=O)NCCCN3CCN(c4ccc(F)cc4)CC3)C2=O)cc1Br]
(293)
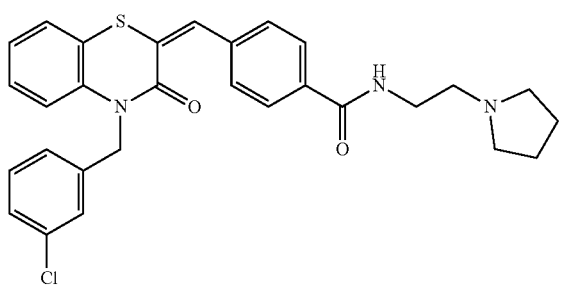 [SMILES: O=C(NCCN1CCCC1)c1ccc(/C=C2/Sc3ccccc3N(Cc3cccc(Cl)c3)C2=O)cc1]
(295)
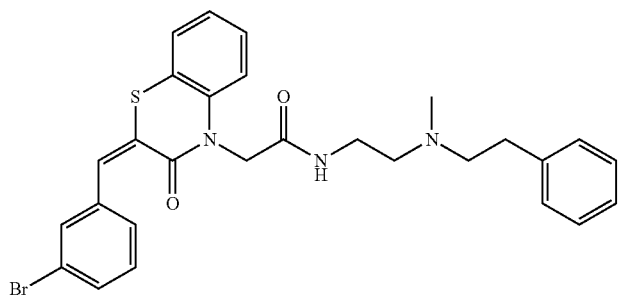 [SMILES: CN(CCNC(=O)CN1C(=O)/C(=C\c2cccc(Br)c2)Sc2ccccc21)CCc1ccccc1]
(297)
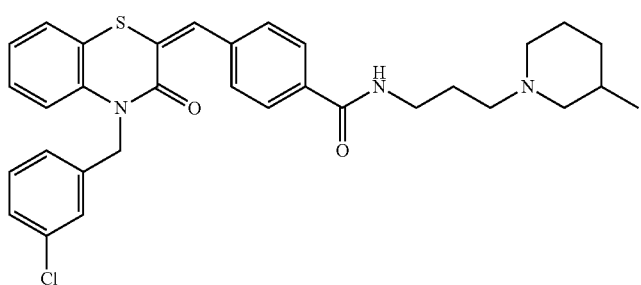 [SMILES: CC1CCCN(CCCNC(=O)c2ccc(/C=C3/Sc4ccccc4N(Cc4cccc(Cl)c4)C3=O)cc2)C1]
(299)
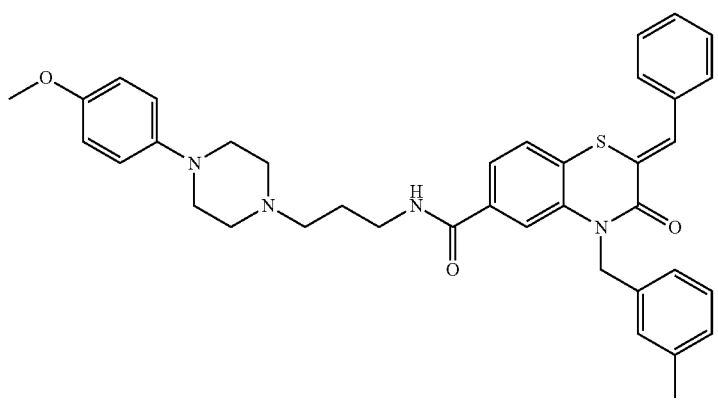 [SMILES: COc1ccc(N2CCN(CCCNC(=O)c3ccc4c(c3)N(Cc3cccc(C)c3)C(=O)/C(=C/c3ccccc3)S4)CC2)cc1]
(301)

TABLE 1.3-continued
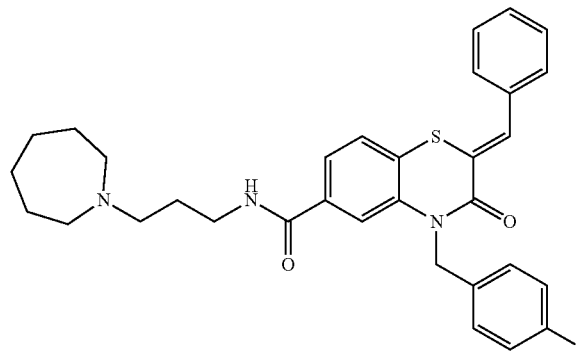
(303)
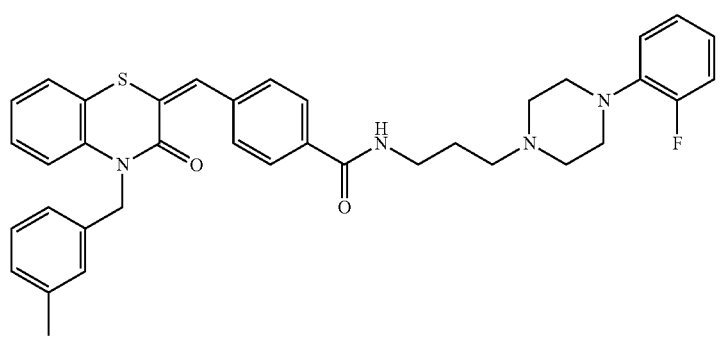 [SMILES: Cc1cccc(CN2C(=O)/C(=C\c3ccc(C(=O)NCCCN4CCN(c5ccccc5F)CC4)cc3)Sc3ccccc32)c1]
(305)
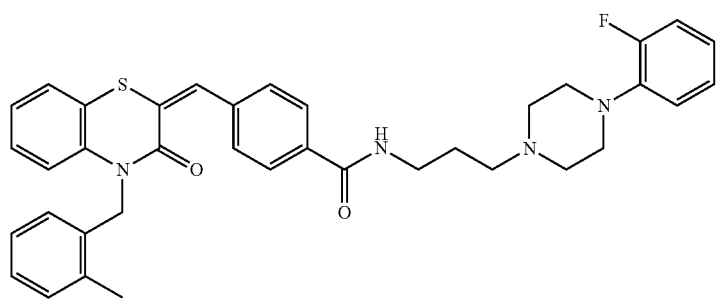 [SMILES: Cc1ccccc1CN1C(=O)/C(=C\c2ccc(C(=O)NCCCN3CCN(c4ccccc4F)CC3)cc2)Sc2ccccc21]
(307)
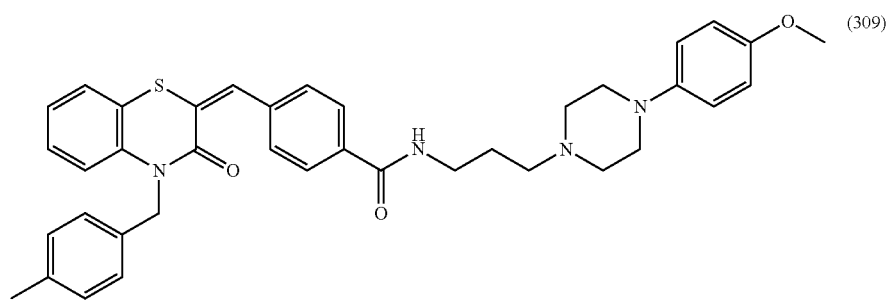
(309)
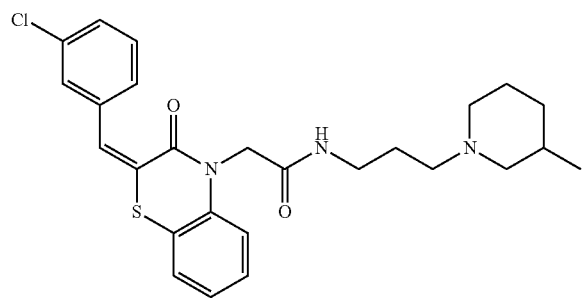 [SMILES: CC1CCCN(CCCNC(=O)CN2C(=O)/C(=C\c3cccc(Cl)c3)Sc3ccccc32)C1]
(311)

TABLE 1.3-continued
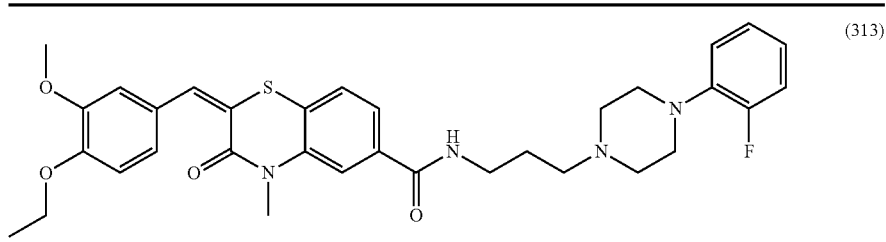
(313)
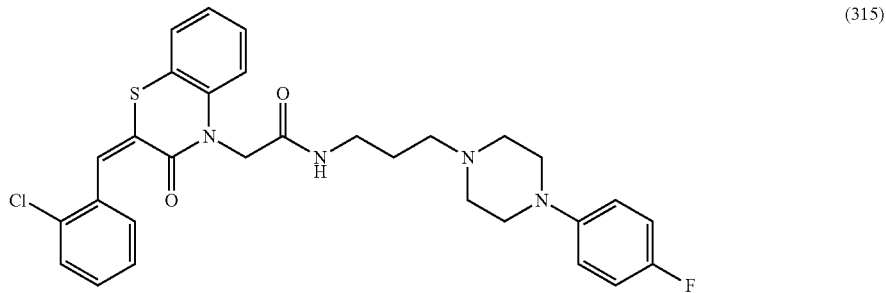
(315)
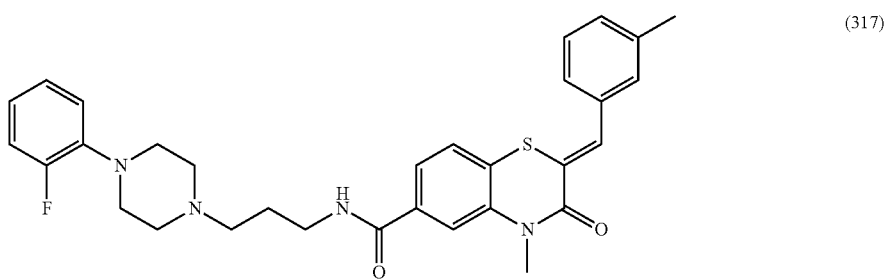
(317)
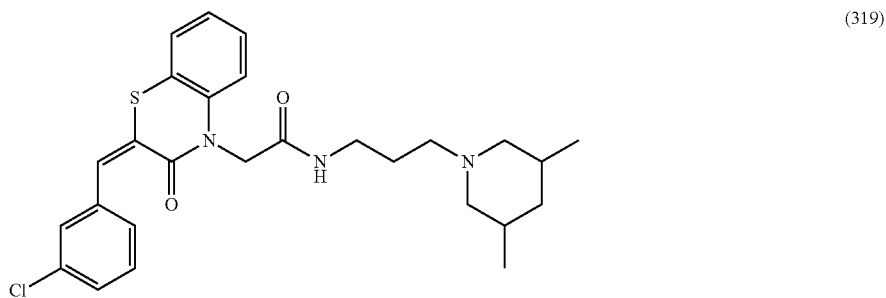
(319)
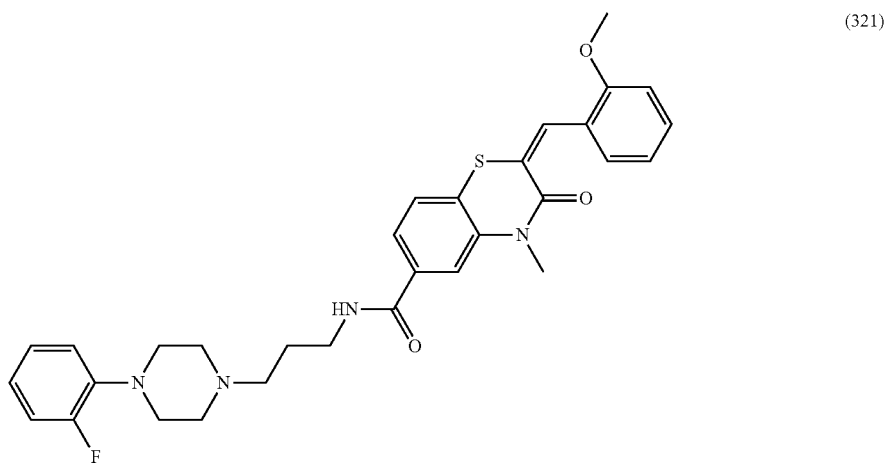
(321)

TABLE 1.3-continued
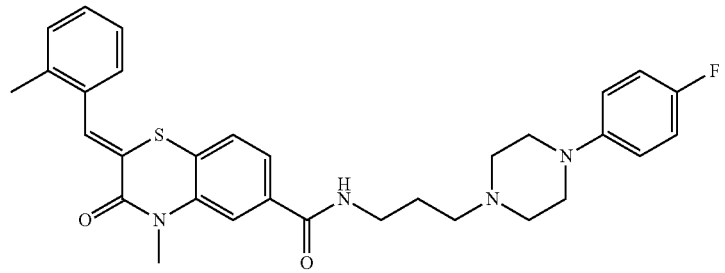 [SMILES: Cc1ccccc1/C=C1\Sc2ccc(C(=O)NCCCN3CCN(c4ccc(F)cc4)CC3)cc2N(C)C1=O]
(323)
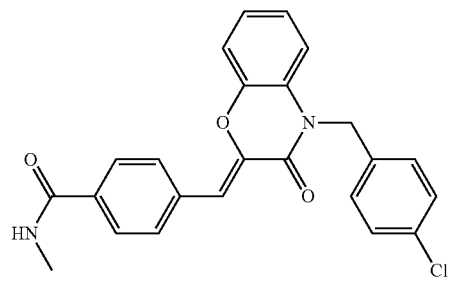 [SMILES: CNC(=O)c1ccc(/C=C2\Oc3ccccc3N(Cc3ccc(Cl)cc3)C2=O)cc1]
(421)
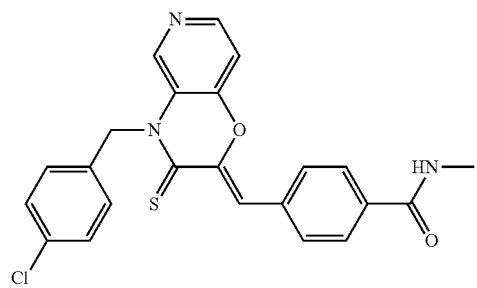 [SMILES: CNC(=O)c1ccc(/C=C2\Oc3ccncc3N(Cc3ccc(Cl)cc3)C2=S)cc1]
(423)
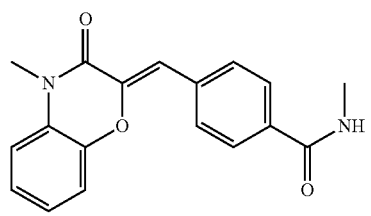 [SMILES: CNC(=O)c1ccc(/C=C2\Oc3ccccc3N(C)C2=O)cc1]
(425)
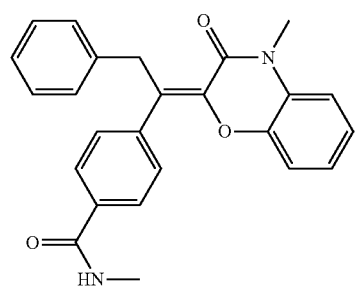 [SMILES: CNC(=O)c1ccc(/C(Cc2ccccc2)=C2\Oc3ccccc3N(C)C2=O)cc1]
(427)

TABLE 1.3-continued
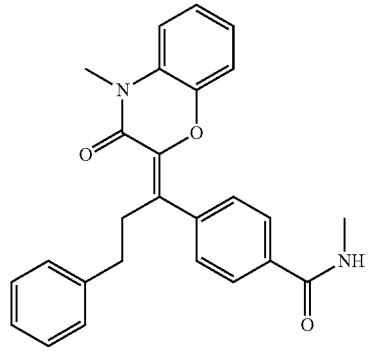 [SMILES: CNC(=O)c1ccc(/C(CCc2ccccc2)=C2\Oc3ccccc3N(C)C2=O)cc1]
(429)
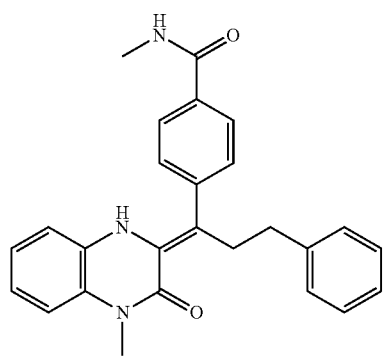 [SMILES: CNC(=O)c1ccc(/C(CCc2ccccc2)=C2\Nc3ccccc3N(C)C2=O)cc1]
(431)
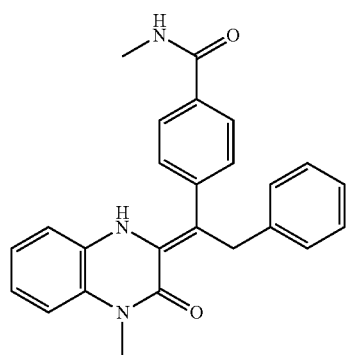 [SMILES: CNC(=O)c1ccc(/C(Cc2ccccc2)=C2\Nc3ccccc3N(C)C2=O)cc1]
(433)
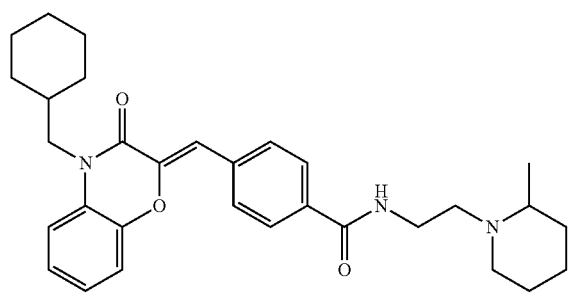 [SMILES: CC1CCCCN1CCNC(=O)c1ccc(/C=C2\Oc3ccccc3N(CC3CCCCC3)C2=O)cc1]
(435)

TABLE 1.3-continued
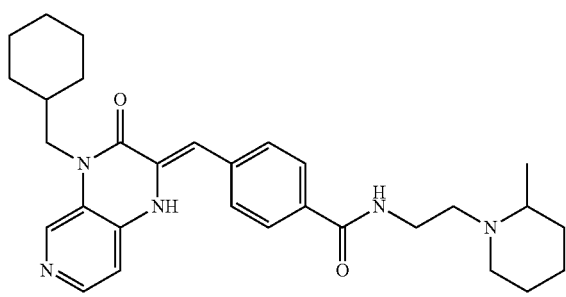 [SMILES: CC1CCCCN1CCNC(=O)c1ccc(/C=C2\Nc3ccncc3N(CC3CCCCC3)C2=O)cc1]
(437)
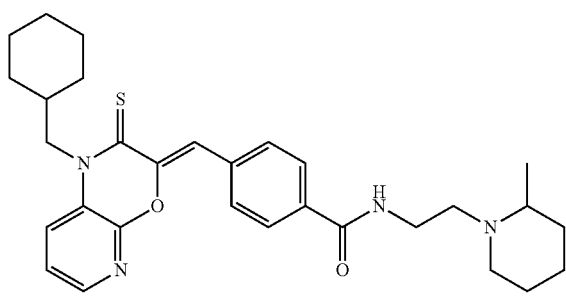 [SMILES: CC1CCCCN1CCNC(=O)c1ccc(/C=C2\Oc3ncccc3N(CC3CCCCC3)C2=S)cc1]
(439)
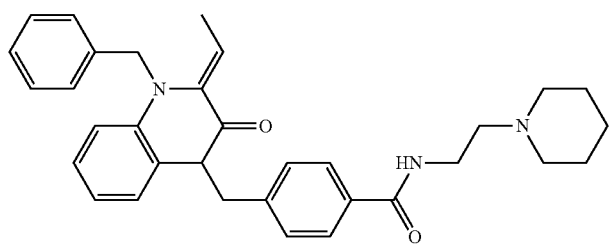 [SMILES: C/C=C1/C(=O)C(Cc2ccc(C(=O)NCCN3CCCCC3)cc2)c2ccccc2N1Cc1ccccc1]
(441)
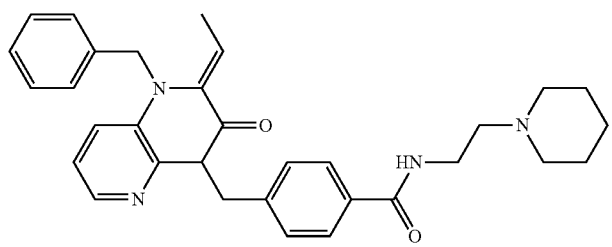 [SMILES: C/C=C1/C(=O)C(Cc2ccc(C(=O)NCCN3CCCCC3)cc2)c2ncccc2N1Cc1ccccc1]
(443)
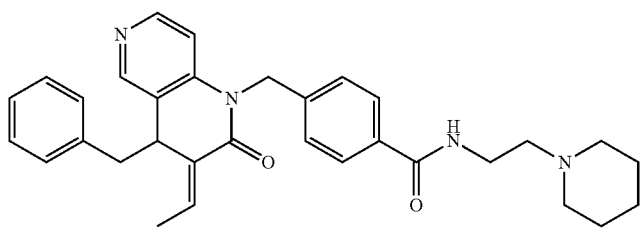 [SMILES: C/C=C1/C(=O)N(Cc2ccc(C(=O)NCCN3CCCCC3)cc2)c2ccncc2C1Cc1ccccc1]
(445)
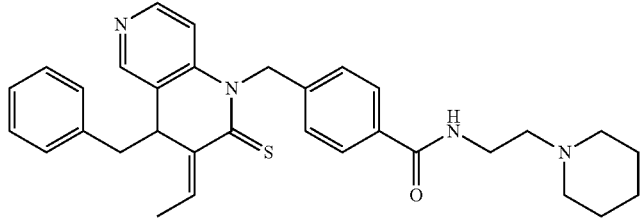 [SMILES: C/C=C1/C(=S)N(Cc2ccc(C(=O)NCCN3CCCCC3)cc2)c2ccncc2C1Cc1ccccc1]
(447)

TABLE 1.3-continued
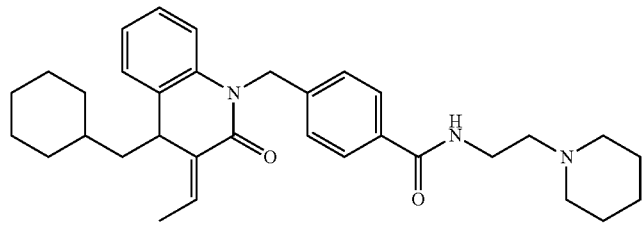 [SMILES: C/C=C1/C(=O)N(Cc2ccc(C(=O)NCCN3CCCCC3)cc2)c2ccccc2C1CC1CCCCC1]
(449)
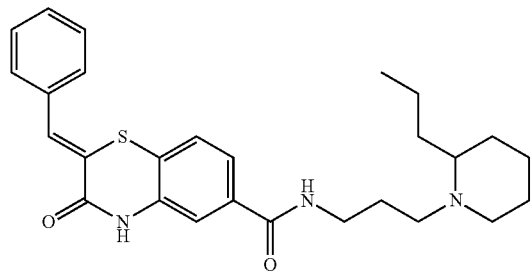 [SMILES: CCCC1CCCCN1CCCNC(=O)c1ccc2c(c1)NC(=O)/C(=C/c1ccccc1)S2]
(451)
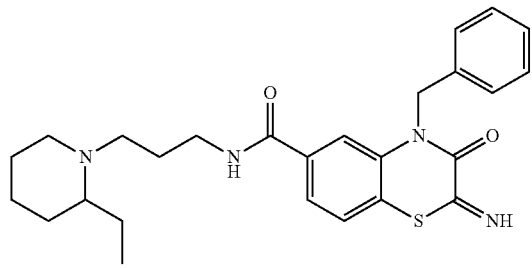 [SMILES: CCC1CCCCN1CCCNC(=O)c1ccc2sc(=N)c(=O)n(Cc3ccccc3)c2c1]
(453)
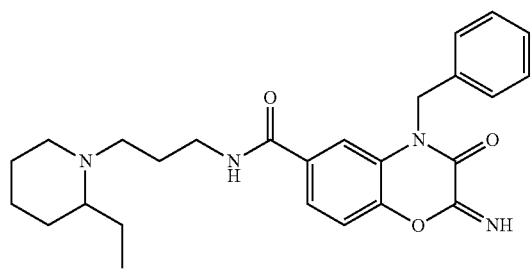 [SMILES: CCC1CCCCN1CCCNC(=O)c1ccc2oc(=N)c(=O)n(Cc3ccccc3)c2c1]
(455)
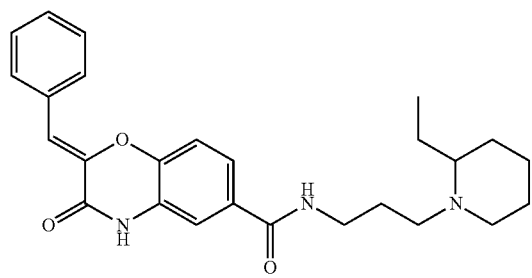 [SMILES: CCC1CCCCN1CCCNC(=O)c1ccc2c(c1)NC(=O)/C(=C/c1ccccc1)O2]
(457)
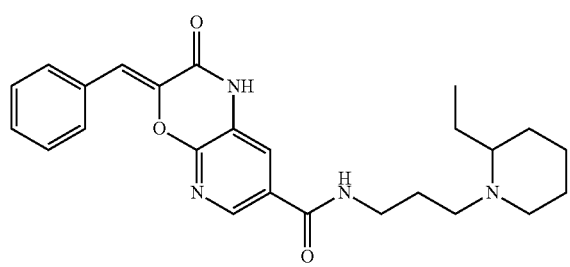 [SMILES: CCC1CCCCN1CCCNC(=O)c1cnc2c(c1)NC(=O)/C(=C/c1ccccc1)O2]
(459)

TABLE 1.3-continued
| | |
|---|---|
| 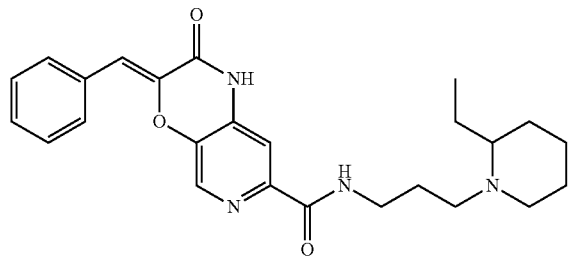 | (461) |
| 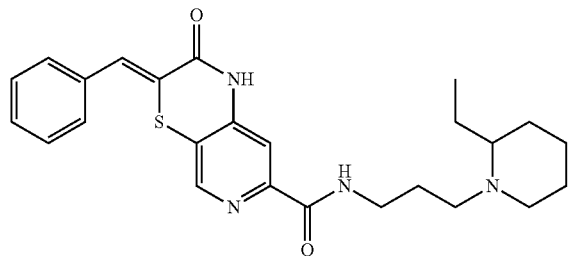 | (463) |
| 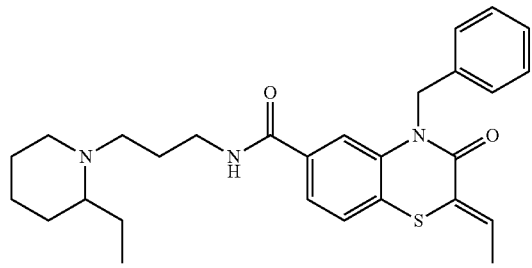 | (465) |
| 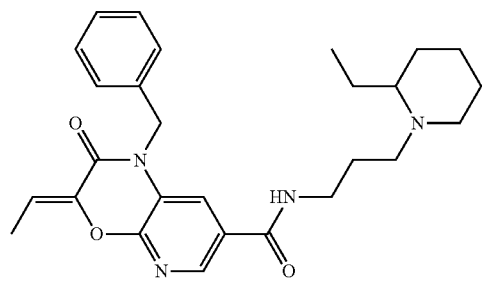 | (467) |
| 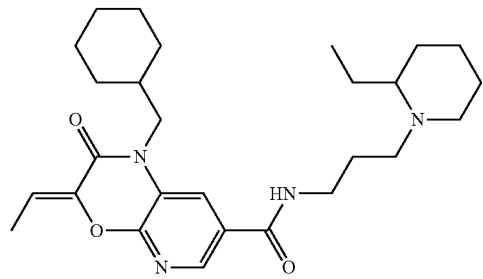 | (469) |
| 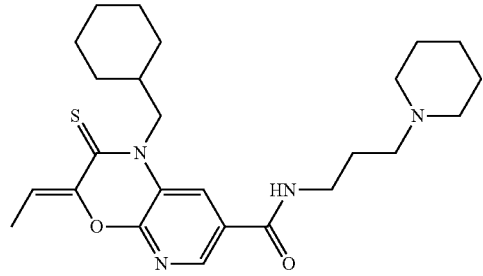 | (471) |

TABLE 1.3-continued
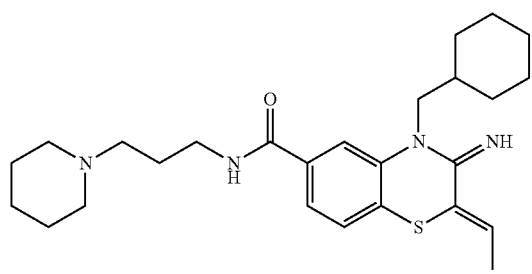 [SMILES: C/C=C1\Sc2ccc(C(=O)NCCCN3CCCCC3)cc2N(CC2CCCCC2)C1=N]
(473)
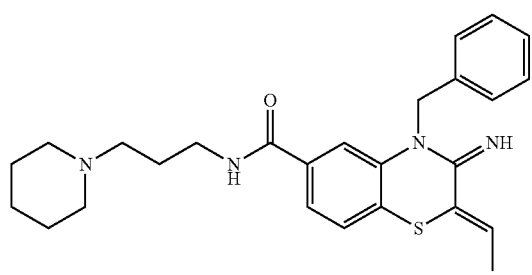 [SMILES: C/C=C1\Sc2ccc(C(=O)NCCCN3CCCCC3)cc2N(Cc2ccccc2)C1=N]
(475)
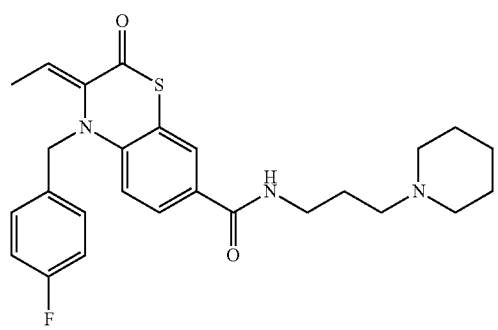 [SMILES: C/C=C1/C(=O)Sc2cc(C(=O)NCCCN3CCCCC3)ccc2N1Cc1ccc(F)cc1]
(477)
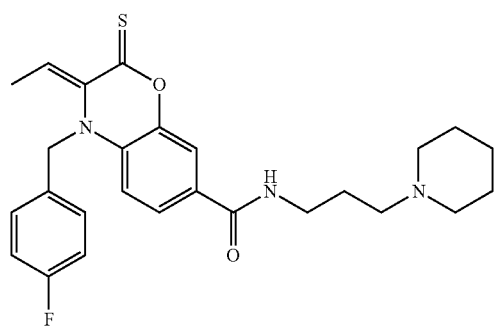 [SMILES: C/C=C1/C(=S)Oc2cc(C(=O)NCCCN3CCCCC3)ccc2N1Cc1ccc(F)cc1]
(479)
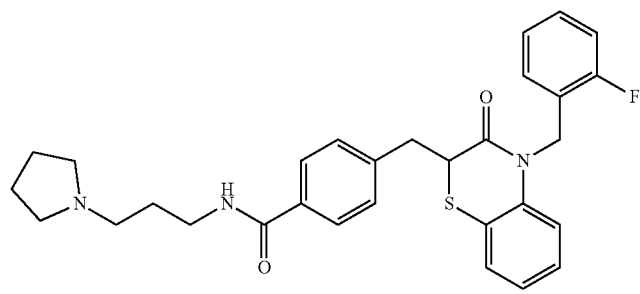 [SMILES: O=C(NCCCN1CCCC1)c1ccc(CC2Sc3ccccc3N(Cc3ccccc3F)C2=O)cc1]
(481)

TABLE 1.3-continued

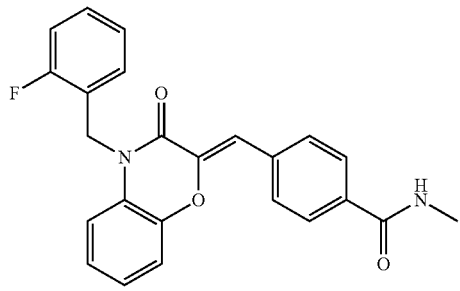 [SMILES: CNC(=O)c1ccc(/C=C2\Oc3ccccc3N(Cc3ccccc3F)C2=O)cc1]
(483)

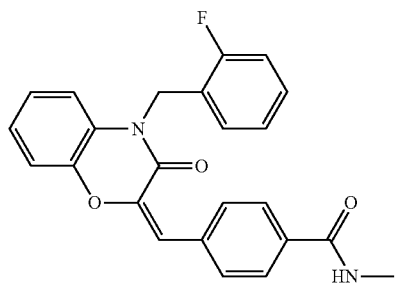 [SMILES: CNC(=O)c1ccc(/C=C2/Oc3ccccc3N(Cc3ccccc3F)C2=O)cc1]
(485)

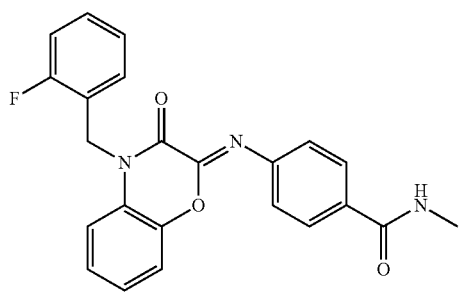 [SMILES: CNC(=O)c1ccc(/N=c2\oc3ccccc3n(Cc3ccccc3F)c2=O)cc1]
(487)

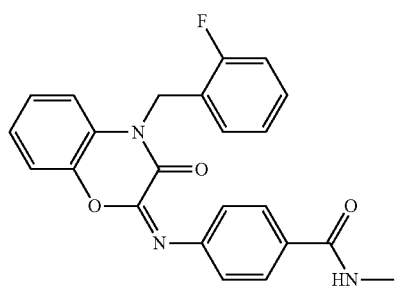 [SMILES: CNC(=O)c1ccc(/N=c2/oc3ccccc3n(Cc3ccccc3F)c2=O)cc1]
(489)

Compounds listed in Table 1.3 may also be represented by their chemical names as follows:

| ID | IUPAC Name |
|---|---|
| 203 | (2Z)-2-benzylidene-N-[3-(4-benzylpiperidin-1-yl)propyl]-4-(4-fluorobenzyl)-3-oxo-3,4-dihydro-2H-1,4-benzothiazine-6-carboxamide |
| 205 | N-[3-(4-benzylpiperidin-1-yl)propyl]-2-[(2E)-2-(3-bromo-4-methoxybenzylidene)-3-oxo-2,3-dihydro-4H-1,4-benzothiazin-4-yl]acetamide |
| 207 | 4-{(E)-[4-(3-chlorobenzyl)-3-oxo-3,4-dihydro-2H-1,4-benzothiazin-2-ylidene]methyl}-N-[2-(dibutylamino)ethyl]benzamide |
| 209 | N-[3-(4-benzylpiperidin-l-yl)propyl]-2-[(2Z)-2-(3-chlorobenzylidene)-3-oxo-2,3-dihydro-4H-1,4-benzothiazin-4-yl]acetamide |
| 211 | (2Z)-2-benzylidene-N-{3-[cyclohexyl(methyl)amino]propyl}-4-(4-fluorobenzyl)-3-oxo-3,4-dihydro-2H-1,4-benzothiazine-6-carboxamide |
| 213 | (2Z)-2-benzylidene-N-[3-(4-benzylpiperidin-l-yl)propyl]-4-(3-methylbenzyl)-3-oxo-3,4-dihydro-2H-1,4-benzothiazine-6-carboxamide |
| 215 | (2Z)-2-benzylidene-N-{3-[cyclohexyl(methyl)amino]propyl}-4-(3-methylbenzyl)-3-oxo-3,4-dihydro-2H-1,4-benzothiazine-6-carboxamide |

-continued

| ID | IUPAC Name |
|---|---|
| 217 | N-[3-(4-benzylpiperidin-l-yl)propyl]-2-[(2E)-2-(3-bromobenzylidene)-3-oxo-2,3-dihydro-4H-1,4-benzothiazin-4-yl]acetamide |
| 219 | (2Z)-N-[2-(azepan-l-yl)ethyl]-2-benzylidene-4-(3-methylbenzyl)-3-oxo-3,4-dihydro-2H-1,4-benzothiazine-6-carboxamide |
| 221 | N-[2-(4-benzylpiperidin-1-yl)ethyl]-4-{(E)-[4-(2,5-dimethylbenzyl)-3-oxo-3,4-dihydro-2H-1,4-benzothiazin-2-ylidene]methyl}benzamide |
| 223 | (2Z)-2-benzylidene-N-[3-(2-ethylpiperidin-1-yl)propyl]-4-(4-fluorobenzyl)-3-oxo-3,4-dihydro-2H-1,4-benzothiazine-6-carboxamide |
| 225 | 4-{(E)-[4-(3-chlorobenzyl)-3-oxo-3,4-dihydro-2H-1,4-benzothiazin-2-ylidene]methyl)-N-{3-[cyclohexyl(methyl)amino]propyl}benzamide |
| 227 | (2Z)-N-[3-(azepan-1-yl)propyl]-2-benzylideiie-4-(3-methylbenzyl)-3-oxo-3,4-dihydro-2H-1,4-benzothiazine-6-carboxamide |
| 229 | (2Z)-2-benzylidene-4-(4-fluorobenzyl)-N-[3-(3-methylpiperidin-l-yl)propyl]-3-oxo-3,4-dihydro-2H-1,4-benzothiazine-6-carboxamide |
| 231 | N-[2-(azepan-1-yl)ethyl]-4-{(E)-[4-(3-methylbenzyl)-3-oxo-3,4-dihydro-2H-1,4-benzothiazin-2-ylidene]methyl}benzamide |
| 233 | N-{3-[cyclohexyl(methyl)amino]propyl}-4-{(E)-[4-(3-methylbenzyl)-3-oxo-3,4-dihydro-2H-1,4-benzothiazin-2-ylidene]methyl}benzamide |
| 235 | N-[2-(azepan-1-yl)ethyl]-4-{(E)-[4-(3-chlorobenzyl)-3-oxo-3,4-dihydro-2H-1,4-benzothiazin-2-ylidene]methyl}benzamide |
| 237 | (2Z)-N-{2-[4-(2-fluorophenyl)piperazin-1-yl]ethyl}-2-[2-(4-methoxyphenyl)-2-oxoethylidene]-3-oxo-1,2,3,4-tetrahydroquinoxaline-6-carboxamide |
| 239 | 2-[(2Z)-2-(3-chlorobenzylidene)-3-oxo-2,3-dihydro-4H-1,4-benzothiazin-4-yl]-N-{3-[4-(4-methoxyphenyl)piperazin-1-yl]propyl}acetamide |
| 241 | (2Z)-2-benzylidene-N-{3-[4-(2,5-dimethylphenyl)piperazin-1-yl]propyl}-4-(3-methylbenzyl)-3-oxo-3,4-dihydro-2H-1,4-benzothiazine-6-carboxamide |
| 243 | 4-{(E)-[4-(3-chlorobenzyl)-3-oxo-3,4-dihydro-2H-1,4-benzothiazin-2-ylidene]methyl}-N-[(1-ethylpyrrolidin-2-yl)methyl]benzamide |
| 245 | N-{3-[cyclohexyl(methyl)amino]propyl}-4-{(E)-[4-(2-methylbenzyl)-3-oxo-3,4-dihydro-2H-1,4-benzothiazin-2-ylidene]methyl}benzamide |
| 247 | (2Z)-2-benzylidene-N-[3-(3,5-dimethylpiperidin-l-yl)propyl]-4-(3-methylbenzyl)-3-oxo-3,4-dihydro-2H-1,4-benzothiazine-6-carboxamide |
| 249 | (2Z)-2-benzylidene-N-[3-(3,5-dimethylpiperidin-l-yl)propyl]-4-(4-fluorobenzyl)-3-oxo-3,4-dihydro-2H-1,4-benzothiazine-6-carboxamide |
| 251 | N-{3-[benzyl(methyl)amino]propyl}-4-{(E)-[4-(3-methylbenzyl)-3-oxo-3,4-dihydro-2H-1,4-benzothiazin-2-ylidene]methyl}benzamide |
| 253 | N-[2-(azepan-1-yl)ethyl]-2-[(2E)-2-(3-chlorobenzylidene)-3-oxo-2,3-dihydro-4H-1,4-benzothiazin-4-yl]acetamide |
| 255 | 2-[(2E)-2-(3-bromo-4-methoxybenzylidene)-3-oxo-2,3-dihydro-4H-1,4-benzothiazin-4-yl]-N-{3-[4-(2-fluorophenyl)piperazin-1-yl]propyl}acetamide |
| 257 | N-{3-[benzyl(methyl)amino]propyl}-2-[(2Z)-2-(3-chlorobenzylidene)-3-oxo-2,3-dihydro-4H-1,4-benzothiazin-4-yl]acetamide |
| 259 | 2-[(2Z)-2-(3-chlorobenzylidene)-3-oxo-2,3-dihydro-4H-1,4-benzothiazin-4-yl]-N-{3-[4-(2-fluorophenyl)piperazin-1-yl]propyl}acetamide |
| 261 | N-{2-[butan-2-yl(cyclohexyl)amino]ethyl}-4-{(E)-[4-(2-fluorobenzyl)-3-oxo-3,4-dihydro-2H-1,4-benzothiazin-2-ylidene]methyl)benzamide |
| 263 | N-{2-[cyclohexyl(methyl)amino]ethyl}-4-{(E)-[4-(3-methylbenzyl)-3-oxo-3,4-dihydro-2H-1,4-benzoxazin-2-ylidene]methyl)benzamide |
| 265 | 2-[(2E)-2-(3-bromobenzylidene)-3-oxo-2,3-dihydro-4H-1,4-benzothiazin-4-yl]-7V-[3-(3,5-dimethylpiperidin-1-yl)propyl]acetamide |
| 267 | N-{3-[benzyl(butyl)amino]propyl{-4-{(E)-[4-(3-chlorobenzyl)-3-oxo-3,4-dihydro-2H-1,4-benzothiazin-2-ylidene]methyl}benzamide |
| 269 | N-[2-(azepan-1-yl)ethyl]-2-[(2E)-2-(3-bromo-4-methoxybenzylidene)-3-oxo-2,3-dihydro-4H-1,4-benzothiazin-4-yl]acetamide |
| 271 | 2-[(2Z)-2-(3-chlorobenzylidene)-3-oxo-2,3-dihydro-4H-1,4-benzothiazin-4-yl]-N-{3-[4-(4-fluorophenyl)piperazin-1-yl]propyl}acetamide |
| 273 | 2-[(2E)-2-(3-bromobenzylidene)-3-oxo-2,3-dihydro-4H-1,4-benzothiazin-4-yl]-N-[3-(2-ethylpiperidin-1-yl)propyl]acetamide |
| 275 | N-{3-[4-(5-chloro-2-methylphenyl)piperazin-1-yl]propyl}-4-{(E)-[4-(2-fluorobenzyl)-3-oxo-3,4-dihydro-2H-1,4-benzothiazin-2-ylidene]methyl}benzamide |
| 277 | N-[2-(dipropylamino)ethyl]-4-{(E)-[4-(3-methylbenzyl)-3-oxo-3,4-dihydro-2H-1,4-benzothiazin-2-ylidene]methyl}benzamide |
| 279 | (2Z)-N-[2-(azepan-l-yl)ethyl]-2-benzylidene-4-(4-fluorobenzyl)-3-oxo-3,4-dihydro-2H-1,4-benzothiazine-6-carboxamide |
| 281 | 4-{(E)-[4-(3-chlorobenzyl)-3-oxo-3,4-dihydro-2H-1,4-benzothiazin-2-ylidenee]methyl}-N-{3-[4-(2-fluorophenyl)piperazin-1-yl]propyl}benzamide |
| 283 | 2-[(2Z)-2-(3-chlorobenzylidene)-3-oxo-2,3-dihydro-4H-1,4-benzothiazin-4-yl]-N-{3-[4-(3-chlorophenyl)piperazin-1-yl]propyl}acetamide |
| 285 | 2-[(2E)-2-(3-chlorobenzylidene)-3-oxo-2,3-dihydro-4H-1,4-benzothiazin-4-yl]-N-[3-(2-ethylpiperidin-1-yl)propyl]acetamide |
| 287 | N-{3-[4-(5-chloro-2-methylphenyl)piperazin-1-yl]propyl}-4-{(E)-[4-(3-methylbenzyl)-3-oxo-3,4-dihydro-2H-1,4-benzoxazin-2-ylidene]methyl}benzamide |
| 291 | (2Z)-2-benzylidene-N-[3-(3,4-dihydroisoquinolin-2(1H)-yl)propyl]-4-(3-methylbenzyl)-3-oxo-3,4-dihydro-2H-1,4-benzothiazine-6-carboxamide |
| 293 | 2-[(2Z)-2-(3-bromo-4-methoxybenzylidene)-3-oxo-2,3-dihydro-4H-1,4-benzothiazin-4-yl]-N-{3-[4-(4-fluorophenyl)piperazin-1-yl]propyl}acetamide |

| ID | IUPAC Name |
|---|---|
| 295 | 4-{(E)-[4-(3-chlorobenzyl)-3-oxo-3,4-dihydro-2H-1,4-benzothiazin-2-ylidene]methyl}-N-[2-(pyrrolidin-1-yl)ethyl]benzamide |
| 297 | 2-[(2E)-2-(3-bromobenzylidene)-3-oxo-2,3-dihydro-4H1,4-benzothiazin-4-yl]-N-{2-[methyl(2-phenylethyl)amino]ethyl}acetamide |
| 299 | 4-{(E)-[4-(3-chlorobenzyl)-3-oxo-3,4-dihydro-2H-1,4-benzothiazin-2-ylidene]methyl}-N-[3-(3-methylpiperidin-1-yl)propyl]benzamide |
| 301 | (2Z)-2-benzylidene-N-{3-[4-(4-methoxyphenyl)piperazin-1-yl]propyl}-4-(3-methylbenzyl)-3-oxo-3,4-dihydro-2H-1,4-benzothiazine-6-carboxamide |
| 303 | (2Z)-N-[3-(azepan-l-yl)propyl]-2-benzylidene-4-(4-fluorobenzyl)-3-oxo-3,4-dihydro-2H1,4-benzothiazine-6-carboxamide |
| 305 | N-{3-[4-(2-fluorophenyl)piperazin-1-yl]propyl}-4-{(E)-[4-(3-methylbenzyl)-3-oxo-3,4-dihydro-2H-1,4-benzothiazin-2-ylidene]methyl}benzamide |
| 307 | N-{3-[4-(2-fluorophenyl)piperazin-1-yl]propyl}-4-{(E)-[4-(2-methylbenzyl)-3-oxo-3,4-dihydro-2H-1,4-benzothiazin-2-ylidene]methyl}benzamide |
| 309 | N-{3-[4-(4-methoxyphenyl)piperazin-1-yl]propyl}-4-{(E)-[4-(4-methylbenzyl)-3-oxo-3,4-dihydro-2H-1,4-benzothiazin-2-ylidene]methyl}benzamide |
| 311 | 2-[(2E)-2-(3-chlorobenzylidene)-3-oxo-2,3-dihydro-4H-1,4-benzothiazin-4-yl]-N-[3-(3-methylpiperidin-1-yl)propyl]acetamide |
| 313 | (2E)-2-(4-ethoxy-3-methoxybenzylidene)-N-{3-[4-(2-fluorophenyl)piperazin-l-yl]propyl}-4-methyl-3-oxo-3,4-dihydro-2H-1,4-benzothiazine-6-carboxamide |
| 315 | 2-[(2E)-2-(2-chlorobenzylidene)-3-oxo-2,3-dihydro-4h-1,4-benzothiazin-4-yl]-N-}3-[4-(4-fluorophenyl)piperazin-1-yl]propyl}acetamide |
| 317 | (2Z)-N-{3-[4-(2-fluorophenyl)piperazin-1-yl]propyl}-4-methyl-2-(3-methylbenzylidene)-3-oxo-3,4-dihydro-2H-1,4-benzothiazine-6-carboxamide |
| 319 | 2-[(2E)-2-(3-chlorobenzylidene)-3-oxo-2,3-dihydro-4H-1,4-benzothiazin-4-yl]-N-[3-(3,5-dimethylpiperidin-1-yl)propyl]acetamide |
| 321 | (2E)-N-{3-[4-(2-fluorophenyl)piperazin-1-yl]propyl}-2-(2-methoxybenzylidene)-4-methyl-3-oxo-3,4-dihydro-2H-1,4-benzothiazine-6-carboxamide |
| 323 | (2Z)-N-{3-[4-(4-fluorophenyl)piperazin-1-yl]propyl}-4-methyl-2-(2-methylbenzylidene)-3-oxo-3,4-dihydro-2H-1,4-benzothiazine-6-carboxamide |
| 421 | 4-{(Z)-[4-(4-chlorobenzyl)-3-oxo-3,4-dihydro-2H-1,4-benzoxazin-2-ylidene]methyl}-N-methylbenzamide |
| 423 | 4-{(Z)-[4-(4-chlorobenzyl)-3-thioxo-3,4-dihydro-2H-pyrido[4,3-b][1,4]oxazin-2-ylidene]methyl}-N-methylbenzamide |
| 425 | N-methyl-4-[(Z)-(4-methyl-3-oxo-3,4-dihydro-2H-1,4-benzoxazin-2-ylidene)methyl]benzamide |
| 427 | N-methyl-4-[(1Z)-1-(4-methyl-3-oxo-3,4-dihydro-2H-1,4-benzoxazin-2-ylidene)-2-phenylethyl]benzamide |
| 429 | N-methyl-4-[(1Z)-1-(4-methyl-3-oxo-3,4-dihydro-2H-1,4-benzoxazin-2-ylidene)-3-phenylpropyl]benzamide |
| 431 | N-methyl-4-[(1Z)-1-(4-methyl-3-oxo-3,4-dihydroquinoxalin-2(1H)-ylidene)-3-phenylpropyl]benzamide |
| 433 | N-methyl-4-[(1Z)-1-(4-methyl-3-oxo-3,4-dihydroquinoxalin-2(1H)-ylidene)-2-phenylethyl]benzamide |
| 435 | 4-{(Z)-[4-(cyclohexylmethyl)-3-oxo-3,4-dihydro-2H-1,4-benzoxazin-2-ylidene]methyl}-N-[2-(2-methylpiperidin-1-yl)ethyl]benzamide |
| 437 | 4-{(Z)-[4-(cyclohexylmethyl)-3-oxo-3,4-dihydropyrido[3,4-b]pyrazin-2(1H)-ylidene]methyl}-N-[2-(2-methylpiperidin-1-yl)ethyl]benzamide |
| 439 | 4-{(Z)-[1-(cyclohexylmethyl)-2-thioxo-1,2-dihydro-3H-pyrido[2,3-b][1,4]oxazin-3-ylidene]methyl}-N-[2-(2-methylpiperidin-1-yl)ethyl]benzamide |
| 441 | 4-{[(2Z)-1-benzyl-2-ethylidene-3-oxo-1,2,3,4-tetrahydroquinolin-4-yl]methyl}-N-[2-(piperidin-1-yl)ethyl]benzamide |
| 443 | 4-{[(2Z)-1-benzyl-2-ethylidene-3-oxo-1,2,3,4-tetrahydro-1,5-naphthyridin-4-yl]methyl}-N-[2-(piperidin-1-yl)ethyl]benzamide |
| 445 | 4-{[(3E)-4-benzyl-3-ethylidene-2-oxo-3,4-dihydro-1,6-naphthyridin-1(2H)-yl]methyl}-N-[2-(piperidin-1-yl)ethyl]benzamide |
| 447 | 4-{[(3E)-4-benzyl-3-ethylidene-2-thioxo-3,4-dihydro-1,6-naphthyridin-1(2H)-yl]methyl}-N-[2-(piperidin-1-yl)ethyl]benzamide |
| 449 | 4-{[(3Z)-4-(cyclohexylmethyl)-3-ethylidene-2-oxo-3,4-dihydroquinolin-1(2H)-yl]methyl}-N-[2-(piperidin-1-yl)ethyl]benzamide |
| 451 | (2Z)-2-benzylidene-3-oxo-N-[3-(2-propylpiperidin-1-yl)propyl]-3,4-dihydro-2H-1,4-benzothiazine-6-carboxamide |
| 453 | 4-benzyl-N-[3-(2-ethylpiperidin-l-yl)propyl]-2-imino-3-oxo-3,4-dihydro-2H-1,4-benzothiazine-6-carboxamide |
| 455 | 4-benzyl-N-[3-(2-ethylpiperidin-1-yl)propyl]-2-imino-3-oxo-3,4-dihydro-2H-1,4-benzoxazine-6-carboxamide |
| 457 | (2Z)-2-benzylidene-N-[3-(2-ethylpiperidin-1-yl)propyl]-3-oxo-3,4-dihydro-2H-1,4-benzoxazine-6-carboxamide |
| 459 | (3Z)-3-benzylidene-N-[3-(2-ethylpiperidin-1-yl)propyl]-2-oxo-2,3-dihydro-1H-pyrido[2,3-b][1,4]oxazine-7-carboxamide |

| ID | IUPAC Name |
|---|---|
| 461 | (3Z)-3-benzylidene-N-[3-(2-ethylpiperidin-1-yl)propyl]-2-oxo-2,3-dihydro-1H-pyrido[3,4-b][1,4]oxazine-7-carboxamide |
| 463 | (3Z)-3-benzylidene-N-[3-(2-ethylpiperidin-1-yl)propyl]-2-oxo-2,3-dihydro-1H-pyrido[3,4-b][1,4]thiazine-7-carboxamide |
| 465 | (2Z)-4-benzyl-2-ethylidene-N-[3-(2-ethylpiperidin-1-yl)propyl]-3-oxo-3,4-dihydro-2h-1,4-benzothiazine-6-carboxamide |
| 467 | (3Z)-1-benzyl-3-ethylidene-N-[3-(2-ethylpiperidin-1-yl)propyl]-2-oxo-2,3-dihydro-1H-pyrido[2,3-b][1,4]oxazine-7-carboxamide |
| 469 | (3Z)-1-(cyclohexylmethyl)-3-ethylidene-N-[3-(2-ethylpiperidin-1-yl)propyl]-2-oxo-2,3-dihydro-1H-pyrido[2,3-b][1,4]oxazine-7-carboxamide |
| 471 | (3Z)-1-(cyclohexylmethyl)-3-ethylidene-N-[3-(piperidin-1-yl)propyl]-2-thioxo-2,3-dihydro-1H-pyrido[2,3-6][1,4]oxazine-7-carboxamide |
| 473 | (2Z)-4-(cyclohexylmethyl)-2-ethylidene-3-imino-N-[3-(piperidin-1-yl)propyl]-3,4-dihydro-2H-1,4-benzothiazine-6-carboxamide |
| 475 | (2Z)-4-benzyl-2-ethylidene-3-imino-N-[3-(piperidin-1-yl)propyl]-3,4-dihydro-2H-1,4-benzothiazine-6-carboxamide |
| 477 | (3Z)-3-ethylidene-4-(4-fluorobenzyl)-2-oxo-N-[3-(piperidin-1-yl)propyl]-3,4-dihydro-2H-1,4-benzothiazine-7-carboxamide |
| 479 | (3Z)-3-ethylidene-4-(4-fluorobenzyl)-N-[3-(piperidin-l-yl)propyl]-2-thioxo-3,4-dihydro-2H-1,4-benzoxazine-7-carboxamide |
| 481 | 4-{[4-(2-fluorobenzyl)-3-oxo-3,4-dihydro-2H-1,4-benzothiazin-2-yl]methyl}-N-[3-(pyrrolidin-1-yl)prpoyl]benzamide |
| 483 | 4-{(Z)-[4-(2-fluorobenzyl)-3-oxo-3,4-dihydro-2H-1,4-benzoxazin-2-ylidene]methyl}-N-methylbenzamide |
| 485 | 4-{(E)-[4-(2-fluorobenzyl)-3-oxo-3,4-dihydro-2H-1,4-benzoxazin-2-ylidene]methyl}-N-methylbenzamide |
| 487 | 4-{[(2Z)-4-(2-fluorobenzyl)-3-oxo-3,4-dihydro-2H-1,4-benzoxazin-2-ylidene]amino}-N-methylbenzamide |
| 489 | 4-{[(2E)-4-(2-fluorobenzyl)-3-oxo-3,4-dihydro-2H-1,4-benzoxazin-2-ylidene]amino}-N-methylbenzamide |

In one embodiment of formula (IV), wherein the link of $A_4$-$A_4'$ is a double bond and $A_4'$ is $CR^{41}$.

In one embodiment of formula (IV), the compound having a structural formula (IVa):

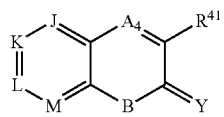

(IVa)

or a salt, solvate, or physiologically functional derivative thereof;
wherein:

$R^{41}$ is hydrogen, halogen, acyl, substituted acyl, alkoxycarbonyl, substituted alkoxycarbonyl, aryloxycarbonyl, substituted aryloxycarbonyl, —C(O)NR$^{42}$R$^{43}$, —NR$^{42}$R$^{43}$, alkyl, substituted alkyl, aryl, substituted aryl, arylalkyl, substituted arylalkyl, cycloheteroalkyl, substituted cycloheteroalkyl, heteroaryl, substituted heteroaryl, heteroarylalkyl, substituted heteroarylalkyl, heteroalkyl, or substituted heteroalkyl;

$R^{42}$ and $R^{43}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl, or alternatively, $R^{42}$ and $R^{43}$, taken together with the nitrogen atom to which they are attached, form a 4-, 5-, 6-, or 7-membered cycloheteroalkyl ring.

In one embodiment of formula (IVa), the compound having a structure selected from the group consisting of:

TABLE 1.4

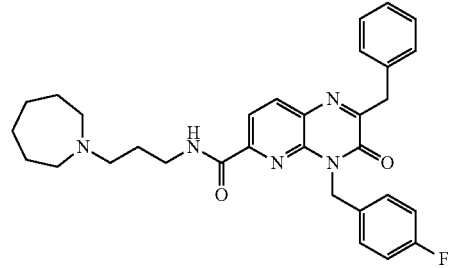 [SMILES: O=C(NCCCN1CCCCCC1)c1ccc2nc(Cc3ccccc3)c(=O)n(Cc3ccc(F)cc3)c2n1]

(491)

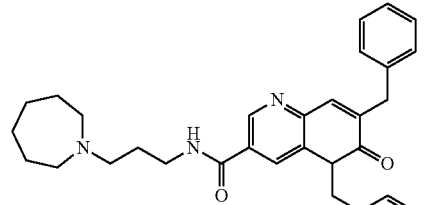

(493)

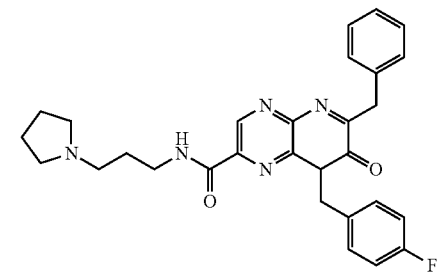 [SMILES: O=C(NCCCN1CCCC1)c1cnc2c(n1)C(Cc1ccc(F)cc1)C(=O)C(Cc1ccccc1)=N2]

(495)

Compounds listed in Table 1.4 may also be represented by their chemical names as follows:

| ID | IUPAC Name |
|---|---|
| 491 | N-[3-(azepan-1-yl)propyl]-2-benzyl-4-(4-fluorobenzyl)-3-oxo-3,4-dihydropyrido[2,3-b]pyrazine-6-carboxamide |
| 493 | N-[3-(azepan-1-yl)propyl]-7-benzyl-5-(4-fluorobenzyl)-6-oxo-5,6-dihydroquinoline-3-carboxamide |
| 495 | 6-benzyl-8-(4-fluorobenzyl)-7-oxo-N-[3-(pyrrolidin-1-yl)propyl]-7,8-dihydropyrido[2,3-b]pyrazine-2-carboxamide |

In one embodiment of formula (IV), wherein $A_4$ and $A_4'$ along with other atoms form a 5, 6, or 7-member ring system.

In one embodiment of formula (IV), the compound having a structural formula (IVb):

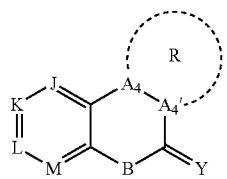

(IVb)

or a salt, solvate, or physiologically functional derivative thereof;
wherein:

R ring is an aryl, substituted aryl, cycloalkyl, substituted cycloalkyl, cycloheteroalkyl, substituted cycloheteroalkyl, heteroaryl or substituted heteroaryl ring. The R ring may be a four-, five-six-, or seven-membered carbocyclic or heterocyclic ring.

In one embodiment of formula (IVb), wherein R ring is a 5-member ring system.

In one embodiment of formula (IVb), the compound having a structural formula (IVb.0):

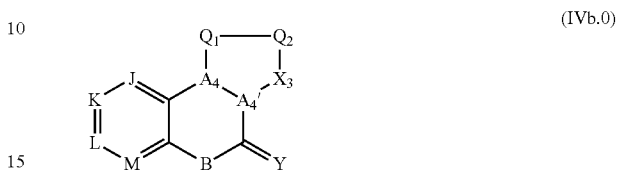

(IVb.0)

or a salt, solvate, or physiologically functional derivative thereof;
wherein:

$A_4$-$Q_1$, $Q_1$-$Q_2$, $Q_2$-$X_3$, $A_4'$-$X_3$, $A_4$-$A_4'$ are independently single or double bond;

$Q_1$, $Q_2$, and $X_3$ are independently S, O, N, N($R^{15}$), C($R^{15}$), C($R^{15}R^{16}$);

$A_4$ and $A_4'$ are independently N, C, or $CR^{17}$;

$R^{15}$, $R^{16}$, and $R^{17}$ are independently hydrogen, halogen, acyl, substituted acyl, alkoxycarbonyl, substituted alkoxycarbonyl, aryloxycarbonyl, substituted aryloxycarbonyl, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl.

In one embodiment of formula (IVb.0), the compound having a structure selected from the group consisting of:

TABLE 1.5

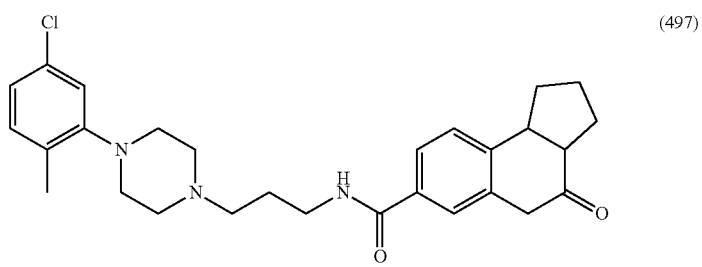

(497)

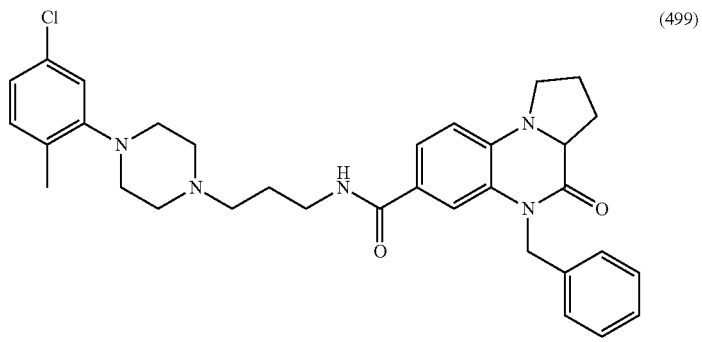

(499)

TABLE 1.5-continued

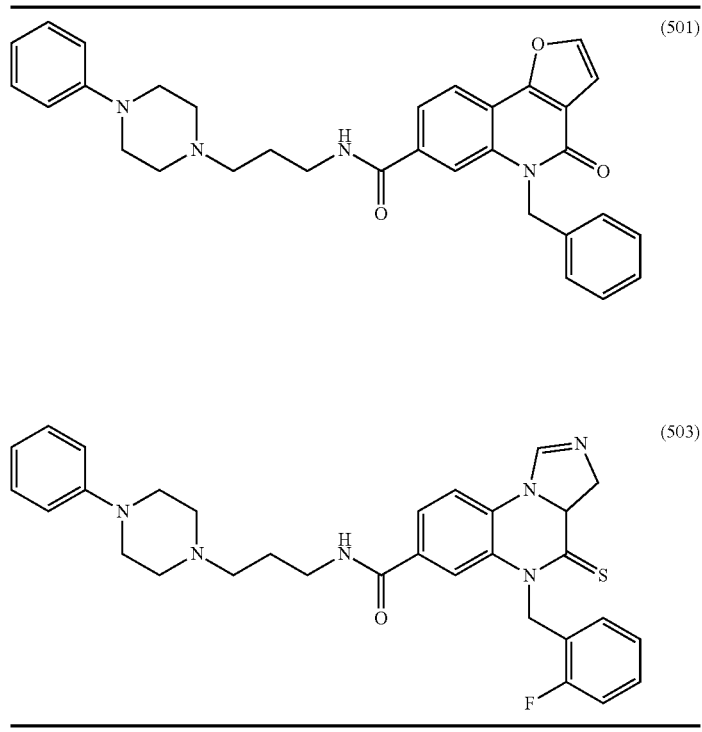

Compounds listed in Table 1.5 may also be represented by their chemical names as follows:

| ID | IUPAC Name |
|---|---|
| 497 | N-{3-[4-(5-chloro-2-methylphenyl)piperazin-1-yl]propyl}-4-oxo-2,3,3a,4,5,9b-hexahydro-1H-cyclopenta[a]naphthalene-7-carboxamide |
| 499 | 5-benzyl-N-{3-[4-(5-chloro-2-methylphenyl)piperazin-1-yl]propyl}-4-oxo-1,2,3,3a,4,5-hexahydropyrrolo[1,2-a]quinoxaline-7-carboxamide |
| 501 | 5-benzyl-4-oxo-N-[3-(4-phenylpiperazin-1-yl)propyl]-4,5-dihydrofuro[3,2-c]quinoline-7-carboxamide |
| 503 | 5-(2-fluorobenzyl)-N-[3-(4-phenylpiperazin-1-yl)propyl]-4-thioxo-3,3a,4,5-tetrahydroimidazo[1,5-a]quinoxaline-7-carboxamide |

In one embodiment of formula (IVb.0), wherein $A_4$-$Q_1$ and $Q_2$-$X_3$ are double bond, and $Q_1$-$Q_2$, $A_4'$-$X_3$, and $A_4$-$A_4'$ are single bond.

In one embodiment of formula (IVb.0), the compound having a structural formula (IVb.1):

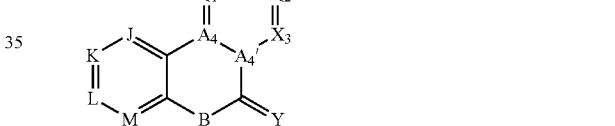
(IVb.1)

or a salt, solvate, or physiologically functional derivative thereof;
wherein:
$A_4$ is C;
$A_4'$ is N or $CR^{18}$;
$X_3$, $Q_1$ and $Q_2$ are independently N or $CR^{19}$;
$R^{18}$, and $R^{19}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl.

In one embodiment of formula (IVb.1), the compound having a structure selected from the group consisting of:

TABLE 1.6

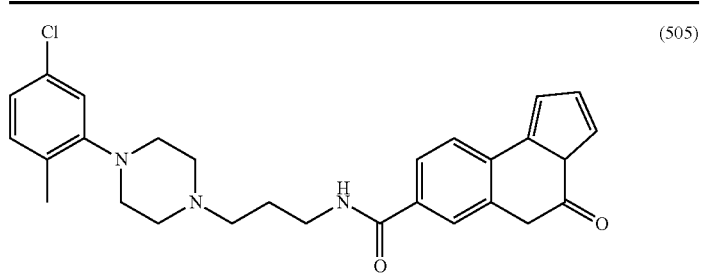
(505)

TABLE 1.6-continued

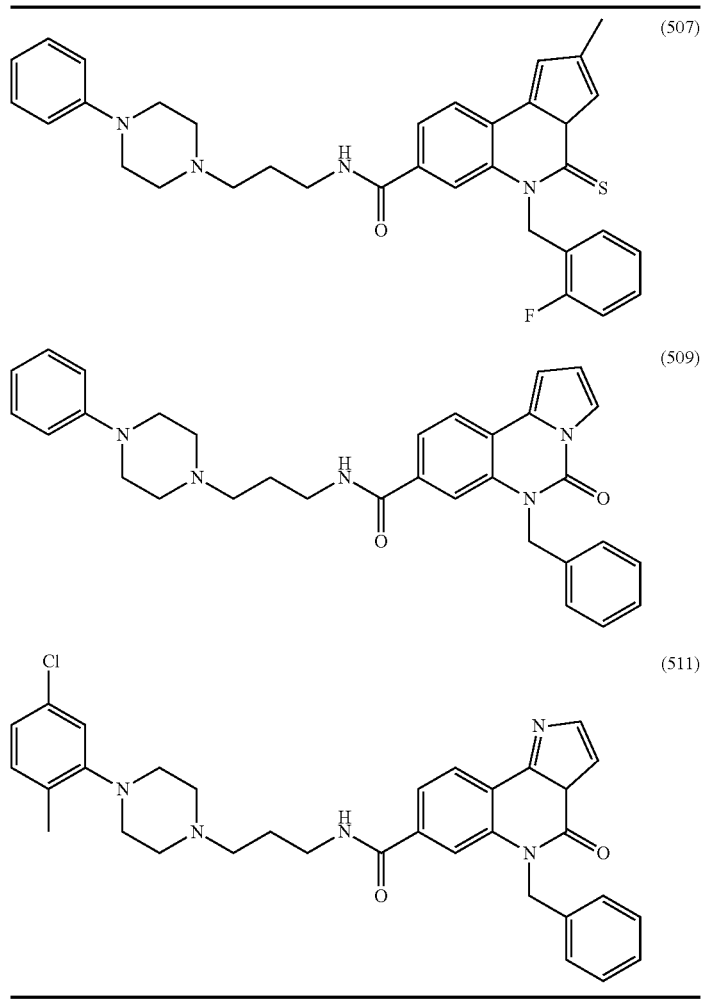

Compounds listed in Table 1.6 may also be represented by their chemical names as follows:

| ID | IUPAC Name |
|---|---|
| 505 | N-{3-[4-(5-chloro-2-methylphenyl)piperazin-1-yl]propyl}-4-oxo-4,5-dihydro-3aH-cyclopenta[a]naphthalene-7-carboxamide |
| 507 | 5-(2-fluorobenzyl)-2-methyl-N-[3-(4-phenylpiperazin-1-yl)propyl]-4-thioxo-4,5-dihydro-3aH-cyclopenta[c]quinoline-7-carboxamide |
| 509 | 6-benzyl-5-oxo-N-[3-(4-phenylpiperazin-1-yl)propyl]-5,6-dihydropyrrolo[1,2-c]quinazoline-8-carboxamide |
| 511 | 5-benzyl-N-{3-[4-(5-chloro-2-methylphenyl)piperazin-1-yl]propyl}-4-oxo-4,5-dihydro-3aH-pyrrolo[3,2-c]quinoline-7-carboxamide |

In one embodiment of formula (IVb), wherein the R ring is a 6-member-ring.

In one embodiment of formula (IVb), the compound having the structural formula (IVb.2):

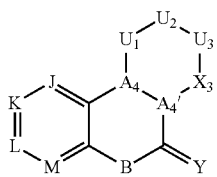

(IVb.2)

or a salt, solvate, or physiologically functional derivative thereof;

wherein:

$A_4$-$U_1$, $U_1$—$U_2$, $U_2$—$U_3$, $U_3$—$X_3$, $A_4'$-$X_3$, $A_4$-$A_4'$ are independently single or double bond; $U_1$, $U_2$, $U_3$, and $X_3$ are independently S, O, N, N($R^{20}$), C($R^{20}$), C($R^{20}OR^{21}$);

$A_4$ and $A_4'$ are independently N, C, or $CR^{22}$ $R^{20}$, $R^{21}$, and $R^{22}$ are independently hydrogen, halogen, acyl, substituted acyl, alkoxycarbonyl, substituted alkoxycarbonyl, aryloxycarbonyl, substituted aryloxycarbonyl, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl.

In one embodiment of formula (IVb.2), the compound having a structure selected from the group consisting of:

TABLE 1.7

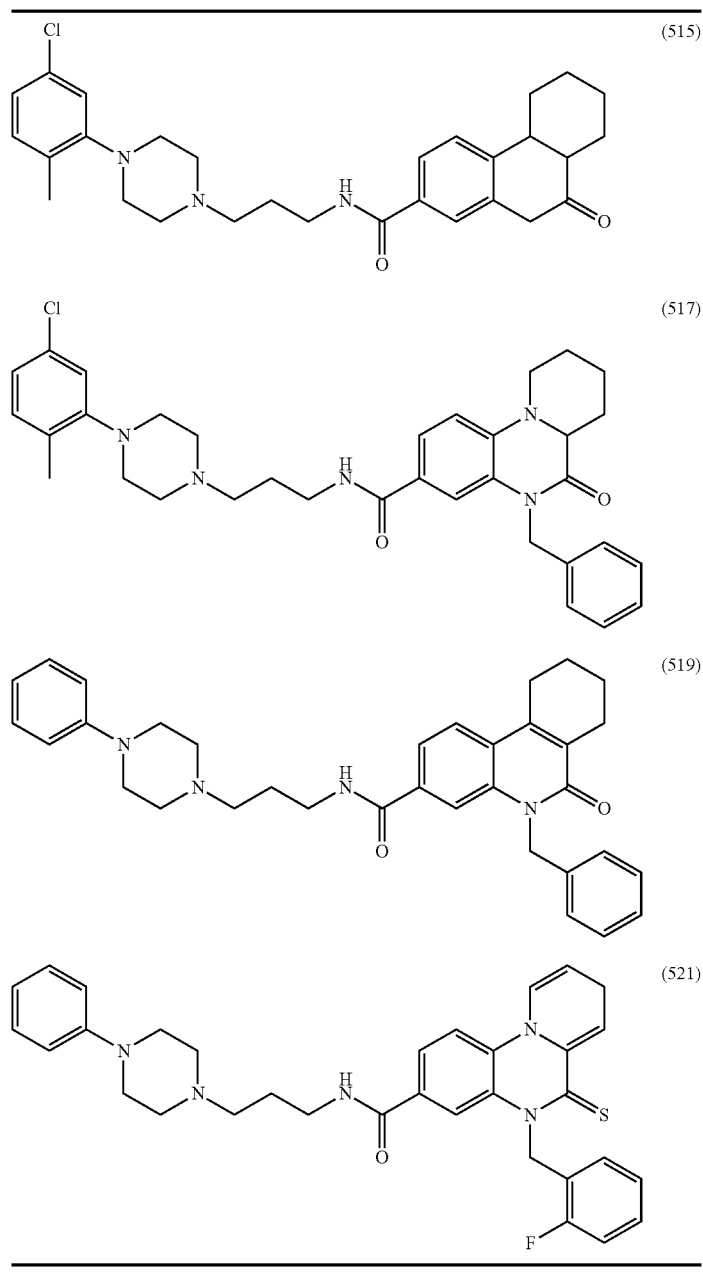

Compounds listed in Table 1.7 may also be represented by their chemical names as follows:

| ID | IUPAC Name |
|---|---|
| 515 | N-{3-[4-(5-chloro-2-methylphenyl)piperazin-1-yl]propyl}-9-oxo-4b,5,6,7,8,8a,9,10-octahydrophenanthrene-2-carboxamide |
| 517 | 5-benzyl-N-{3-[4-(5-chloro-2-methylphenyl)piperazin-1-yl]propyl}-6-oxo-6,6a,7,8,9,10-hexahydro-5H-pyrido[1,2-a]quinoxaline-3-carboxamide |
| 519 | 5-benzyl-6-oxo-N-[3-(4-phenylpiperazin-1-yl)propyl]-5,6,7,8,9,10-hexahydrophenanthridine-3-carboxamide |
| 521 | 5-(2-fluorobenzyl)-N-[3-(4-phenylpiperazin-1-yl)propyl]-6-thioxo-6,8-dihydro-5H-pyrido[1,2-a]quinoxaline-3-carboxamide |

In one embodiment of formula (IVb.2), wherein $U_1$, $U_2$, $U_3$, $X_3$, $A_4'$, and $A_4$ form a 6-membered cycloheteo ring.

In one embodiment of formula (IVb.2), wherein $A_4$ is N, and B is $NR^5$.

In one embodiment of formula (IVb.2), the compound having a structural formula (IVb.21):

(IVb.21)

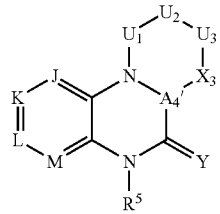

or a salt, solvate, or physiologically functional derivative thereof.
In one embodiment of formula (IVb.21), the compound having a structure selected from the group consisting of:
TABLE 1.8
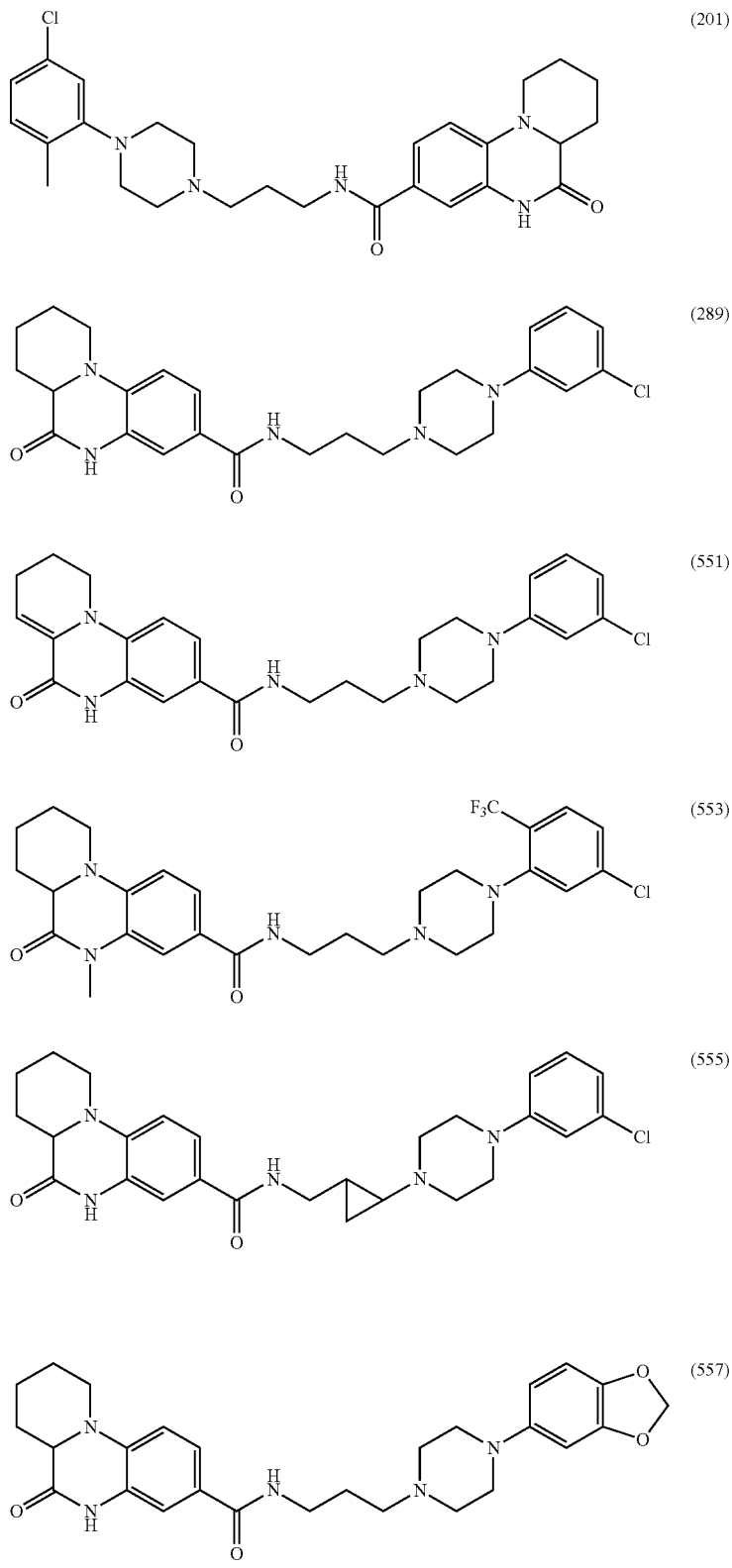

Compounds listed in Table 1.8 may also be represented by their chemical names as follows:

| ID | IUPAC Name |
|---|---|
| 201 | N-{3-[4-(5-chloro-2-methylphenyl)piperazin-1-yl]propyl}-6-oxo-6,6a,7,8,9,10-hexahydro-5H-pyrido[1,2-a]quinoxaline-3-carboxamide |
| 289 | N-{3-[4-(3-chlorophenyl)piperazin-1-yl]propyl}-6-oxo-6,6a,7,8,9,10-hexahydro-5H-pyrido[1,2-a]quinoxaline-3-carboxamide |
| 551 | N-{3-[4-(3-chlorophenyl)piperazin-1-yl]propyl}-6-oxo-6,8,9,10-tetrahydro-5H-pyrido[1,2-a]quinoxaline-3-carboxamide |
| 553 | N-(3-{4-[5-chloro-2-(trifluoromethyl)phenyl]piperazin-1-yl}propyl)-5-methyl-6-oxo-6,6a,7,8,9,10-hexahydro-5H-pyrido[1,2-a]quinoxaline-3-carboxamide |
| 555 | N-({2-[4-(3-chlorophenyl)piperazin-1-yl]cyclopropyl}methyl)-6-oxo-6,6a,7,8,9,10-hexahydro-5H-pyrido[1,2-a]quinoxaline-3-carboxamide |
| 557 | N-{3-[4-(1,3-benzodioxol-5-yl)piperazin-1-yl]propyl}-6-oxo-6,6a,7,8,9,10-hexahydro-5H-pyrido[1,2-a]quinoxaline-3-carboxamide |

In one embodiment of formula (IVb.2), wherein $U_1$, $U_2$, $U_3$, $X_3$, $A_4'$, and $A_4$ form an benzene ring.

In one embodiment of formula (IVb.2), the compound having a structural formula (IVb.22):

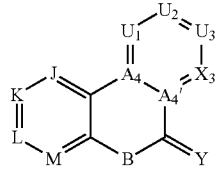

(IVb.22)

or a salt, solvate, or physiologically functional derivative thereof.

In one embodiment of formula (IVb.22), the compound having a structure selected from the group consisting of:

TABLE 1.9

Compounds listed in Table 1.9 may also be represented by their chemical names as follows:

| ID | IUPAC Name |
|---|---|
| 525 | N-{3-[4-(5-chloro-2-methylphenyl)piperazin-1-yl]propyl}-9-oxo-9,10-dihydrophenanthrene-2-carboxamide |
| 527 | 5-(2-fluorobenzyl)-N-[3-(4-phenylpiperazin-1-yl)propyl]-6-thioxo-5,6-dihydrophenanthridine-3-carboxamide |
| 529 | 6-benzyl-5-oxo-N-[3-(4-phenylpiperazin-1-yl)propyl]-5,6-dihydrobenzo[c][2,6]naphthyridine-8-carboxamide |
| 531 | 5-benzyl-N-{3-[4-(5-chloro-2-methylphenyl)piperazin-1-yl]propyl}-6-oxo-5,6-dihydrophenanthridine-3-carboxamide |
| 535 | N-{3-[4-(3-chlorophenyl)piperazin-1-yl]propyl}-6-oxo-5,6-dihydrophenanthridine-3-carboxamide |
| 537 | N-[3-(morpholin-4-yl)propyl]-6-oxo-5,6-dihydrophenanthridine-3-carboxamide |

In one embodiment of formula (I), wherein m=1; n=3; A is "$Z_3$, $A_4$-$X_4$, and $A_5$-$X_5$"; B is $Z_4$.

In one embodiment of formula (I), the compound having a structural of formula (V):

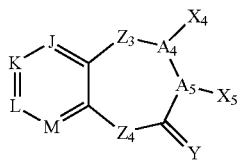
(V)

or a salt, solvate, or physiologically functional derivative thereof;

wherein:

$A_4$-$X_4$, $A_5$-$X_5$ are independently $NR^1$, $C=CR^1$ (E and Z isomers), $C=NR^1$, $C=O$ or $C(R^1R^2)$;

$Z_3$ and $Z_4$ are independently O, S, $NR^3$, or $C(R^3R^4)$; or alternatively, $Z_3$-$A_4$-$X_4$, or $X_4$-$A_4$-$A_5$-$X_5$, together with other atoms, form a six- or seven-member ring which is optionally substituted.

In one embodiment of formula (V), the compound having a structure selected from the group consisting of:

TABLE 2.0

(801)

(803)

(805)

(807)

(809)

Compounds listed in Table 2.0 may also be represented by their chemical names as follows:

| ID | IUPAC Name |
|---|---|
| 801 | 4-{(Z)-[5-(2-fluorobenzyl)-4-oxo-4,5-dihydro-1,5-benzothiazepin-2(3H)-ylidene]methyl}-N-[3-(pyrrolidin-1-yl)propyl]benzamide |
| 803 | 4-{(E)-[5-(2-fluorobenzyl)-4-oxo-4,5-dihydro-1,5-benzothiazepin-2(3H)-ylidene]methyl}-N-[3-(pyrrolidin-1-yl)propyl]benzamide |
| 805 | 4-{[(2Z)-5-(2-fluorobenzyl)-4-oxo-4,5-dihydro-1,5-benzothiazepin-2(3H)-ylidene]amino}-N-[3-(pyrrolidin-1-yl)propyl]benzamide |
| 807 | 4-{[(2E)-5-(2-fluorobenzyl)-4-oxo-4,5-dihydro-1,5-benzothiazepin-2(3H)-ylidene]amino}-N-[3-(pyrrolidin-1-yl)propyl]benzamide |
| 809 | 4-{2-[5-(2-fluorobenzyl)-4-oxo-2,3,4,5-tetrahydro-1,5-benzothiazepin-3yl]ethyl}-N-[3-(pyrrolidin-1-yl)propyl]benzamide |

In one embodiment of formula (V), wherein $Z_3$-$A_4$ is double bond, $A_4$-$X_4$ is $CR^1$, $A_5$-$X_5$ is $C(R^1R^2)$, $NR^1$, $C=CR^1$ (E and Z isomers), or $C=NR^1$ (E and Z isomers).

In one embodiment of formula (V), the compound having the structural formula (Va):

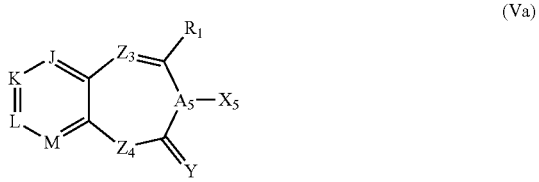
(Va)

or a salt, solvate, or physiologically functional derivative thereof;

wherein:

$Z_3$ and $Z_4$ are independently O, N, S, $N(R^3)$, or $C(R^3R^4)$;

In one embodiment of formula (V), wherein $A_4$-$A_5$ is double bond, $A_4(X_4)$ is $CR^1$, and $A_5(X_5)$ is $CR^2$.

In one embodiment of formula (V), the compound having the structural formula (Vb):

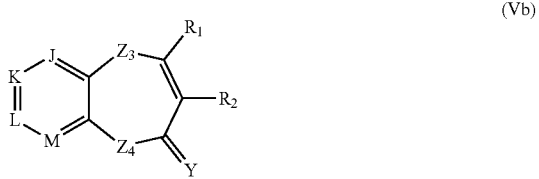
(Vb)

or a salt, solvate, or physiologically functional derivative thereof.

In one embodiment of formula (V), the compounds having a structure selected from the group consisting of:

TABLE 2.1

(811)

TABLE 2.1-continued

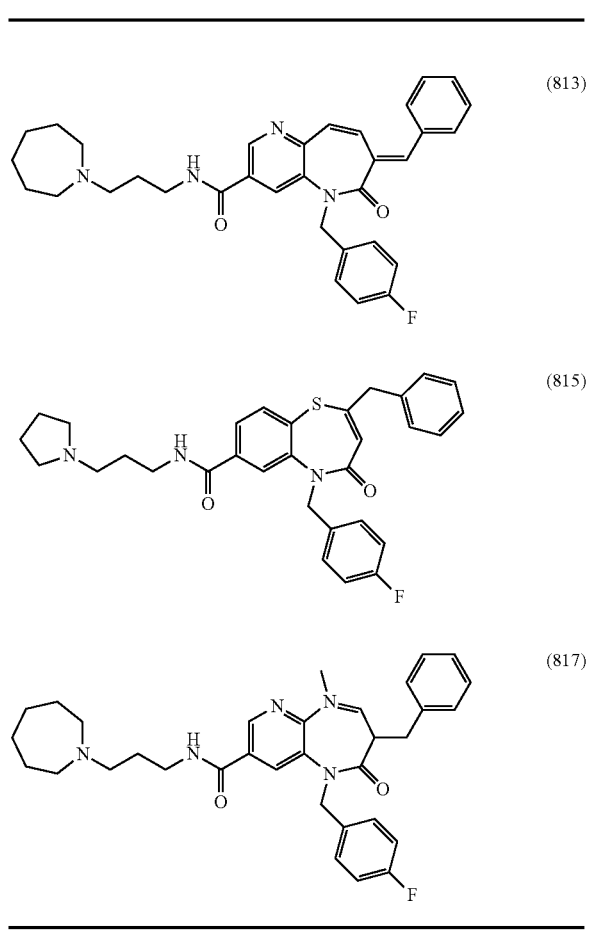

Compounds listed in Table 2.1 may also be represented by their chemical names as follows:

| ID | IUPAC Name |
|---|---|
| 811 | 2-benzyl-5-(4-fluorobenzyl)-3-methyl-4-oxo-N-[3-(pyrrolidin-1-yl)propyl]-4,5-dihydro-3H-1-benzazepine-7-carboxamide |
| 813 | (7E)-N-[3-(azepan-1-yl)propyl]-7-benzylidene-5-(4-fluorobenzyl)-6-oxo-6,7-dihydro-5H-pyrido[3,2-b]azepine-3-carboxamide |
| 815 | 2-benzyl-5-(4-fluorobenzyl)-4-oxo-N-[3-(pyrrolidin-1-yl)propyl]-4,5-dihydro-1,5-benzothiazepine-7-carboxamide |
| 817 | N-[3-(azepan-1-yl)propyl]-3-benzyl-1-(4-fluorobenzyl)-5-methyl-2-oxo-2,5-dihydro-1H-pyrido[2,3-b][1,4]diazepine-8-carboxamide |

In one embodiment of formula (V), wherein Z3 is $NR^3$, or $C(R^3R^4)$.

In one embodiment of formula (V), wherein $R^3$ forms a 5-member ring system with A4-X4.

In one embodiment of formula (V), the compound having the structural formula (Vc):

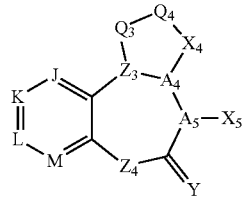

(Vc)

or a salt, solvate, or physiologically functional derivative thereof;

wherein:

$Z_3$-$Q_3$, $Q_3$-$Q_4$, $Q_4$-$X_4$, $A_4$-$X_4$, $Z_3$-$A_4$ are independently single or double bond;

$Q_3$, $Q_4$, and $X_4$ are independently S, O, N, $N(R^{16})$, $C(R^{16})$, $C(R^{16}R^{17})$;

$Z_3$ and $A_4$ are independently N, C, or $CR^{18}$;

$R^{16}$, $R^{17}$, and $R^{18}$ are independently hydrogen, halogen, acyl, substituted acyl, alkoxycarbonyl, substituted alkoxycarbonyl, aryloxycarbonyl, substituted aryloxycarbonyl, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl.

In one embodiment of formula (Vc), the compound having a structure selected from the group consisting of:

TABLE 2.2

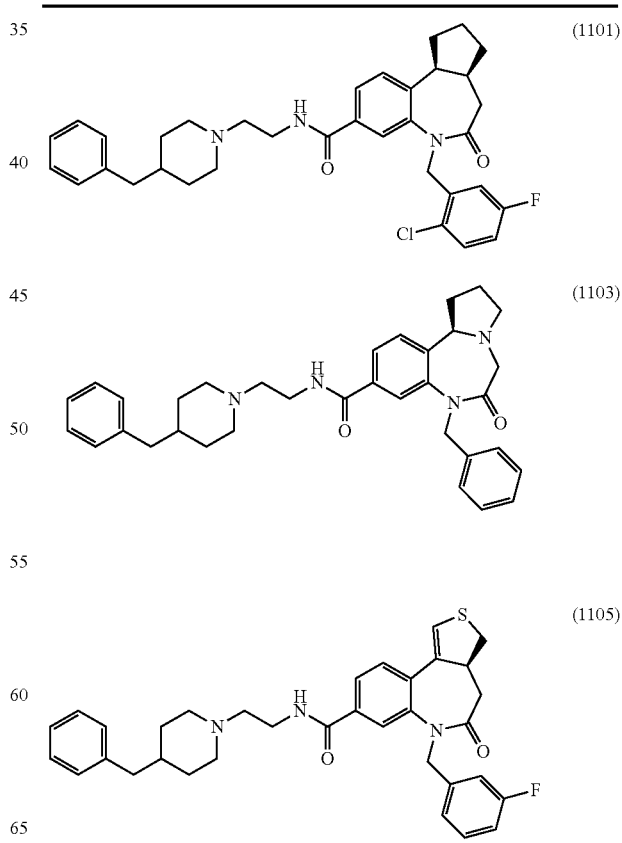

TABLE 2.2-continued

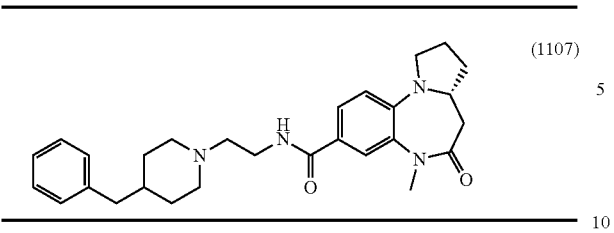
(1107)

Compounds listed in Table 2.2 may also be represented by their chemical names as follows:

| ID | IUPAC Name |
|---|---|
| 1101 | (7aS,10aS)-N-[2-(4-benzylpiperidin-1-yl)ethyl]-5-(2-chloro-5-fluorobenzyl)-6-oxo-5,6,7,7a,8,9,10,10a-octahydrobenzo[b]cyclopenta[d]azepine-3-carboxamide |
| 1103 | (11bR)-7-benzyl-N-[2-(4-benzylpiperidin-1-yl)ethyl]-6-oxo-2,3,5,6,7,11b-hexahydro-1H-pyrrolo[1,2-d][1,4]benzodiazepine-9-carboxamide |
| 1105 | (3aS)-N-[2-(4-benzylpiperidin-1-yl)ethyl]-6-(3-fluorobenzyl)-5-oxo-3a,4,5,6-tetrahydro-3H-thieno[3,4-d][1]benzazepine-8-carboxamide |
| 1107 | (7aR)-N-[2-(4-benzylpiperidin-1-yl)ethyl]-5-methyl-6-oxo-6,7,7a,8,9,10-hexahydro-5H-pyrrolo[1,2-a][1,5]benzodiazepine-3-carboxamide |

In one embodiment of formula (Vc), wherein Z3-Q3 and Q4-X4 are double bond.

In one embodiment of formula (Vc), wherein Z3-A4, Q3-Q4, and A4-X4 are single bond.

In one embodiment of formula (Vc), the compound having the structural formula (Vc. 1):

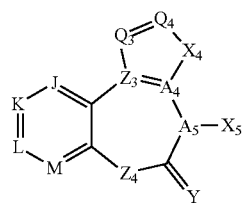
(Vc.1)

or a salt, solvate, or physiologically functional derivative thereof;
wherein:
$Z_3$ is C;
$A_4$ is N or $CR^{18}$;
$X_4$, $Q_3$ and $Q_4$ are independently N or $CR^{16}$ In one embodiment of formula (Vc. 1), the compound having a structure selected from the group consisting of:

TABLE 2.3

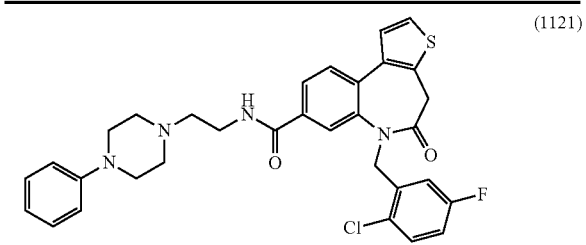
(1121)

TABLE 2.3-continued

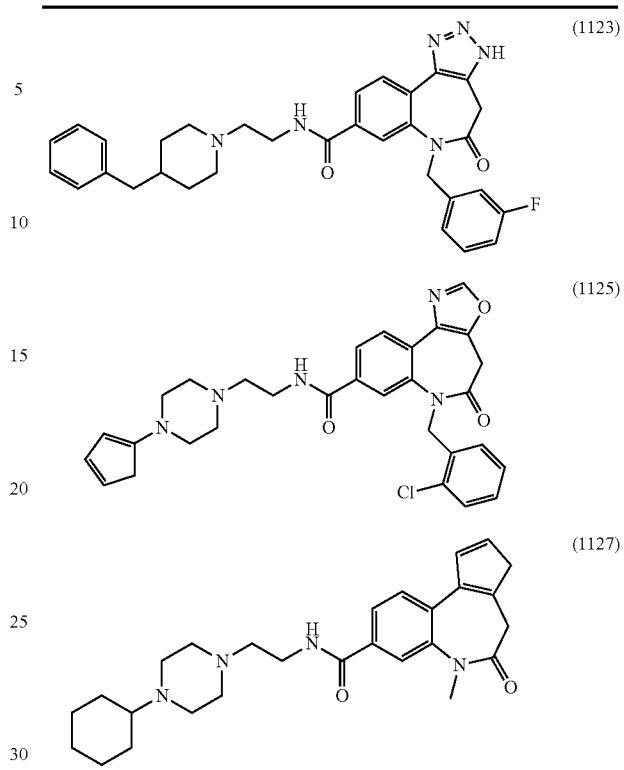
(1123)

(1125)

(1127)

Compounds listed in Table 2.3 may also be represented by their chemical names as follows:

| ID | IUPAC Name |
|---|---|
| 1121 | 6-(2-chloro-5-fluorobenzyl)-5-oxo-N-[2-(4-phenylpiperazin-1-yl)ethyl]-5,6-dihydro-4H-thieno[2,3-d][1]benzazepine-8-carboxamide |
| 1123 | N-[2-(4-benzylpiperidin-1-yl)ethyl]-6-(3-fluorobenzyl)-5-oxo-3,4,5,6-tetrahydro[1,2,3]triazolo[4,5-d][1]benzazepine-8-carboxamide |
| 1125 | 6-(2-chlorobenzyl)-N-{2-[4-(cyclopenta-1,3-dien-1-yl)piperazin-1-yl]ethyl}-5-oxo-5,6-dihydro-4H-[1,3]oxazolo[5,4-d][1]benzazepine-8-carboxamide |
| 1127 | N-[2-(4-cyclohexylpiperazin-1-yl)ethyl]-5-methyl-6-oxo-5,6,7,8-tetrahydrobenzo[b]cyclopenta[d]azepine-3-carboxamide |

In one embodiment of formula (V), wherein $R^3$ forms a 6-member ring system with $A_4$-$X_4$.

In one embodiment of formula (V), the compound having the structural formula (Vd):

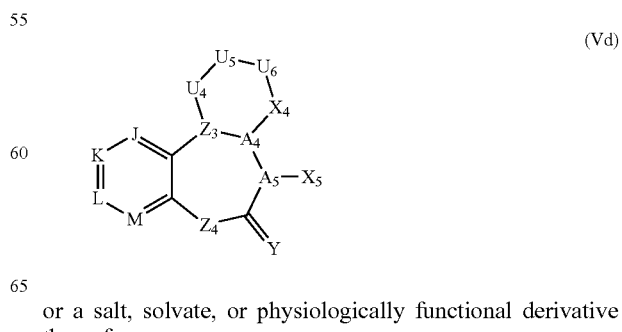
(Vd)

or a salt, solvate, or physiologically functional derivative thereof;

wherein:

$Z_3$—$U_4$, $U_4$—$U_5$, $U_5$—$U_6$, $U_6$—$X_4$, $A_4$-$X_4$, $Z_3$-$A_4$ are independently single or double bond; $U_4$, $U_5$, $U_6$, and $X_4$ are independently S, O, N, $N(R^{19})$, $C(R^{19})$, $C(R^{19}R^{20})$;

$Z_3$ and $A_4$ are independently N, C, or $CR^{21}$ $R^{19}$, $R^{20}$, and $R^{21}$ are independently hydrogen, halogen, acyl, substituted acyl, alkoxycarbonyl, substituted alkoxycarbonyl, aryloxycarbonyl, substituted aryloxycarbonyl, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl.

In one embodiment of formula (Vd), the compound having a structure selected from the group consisting of:

TABLE 2.4

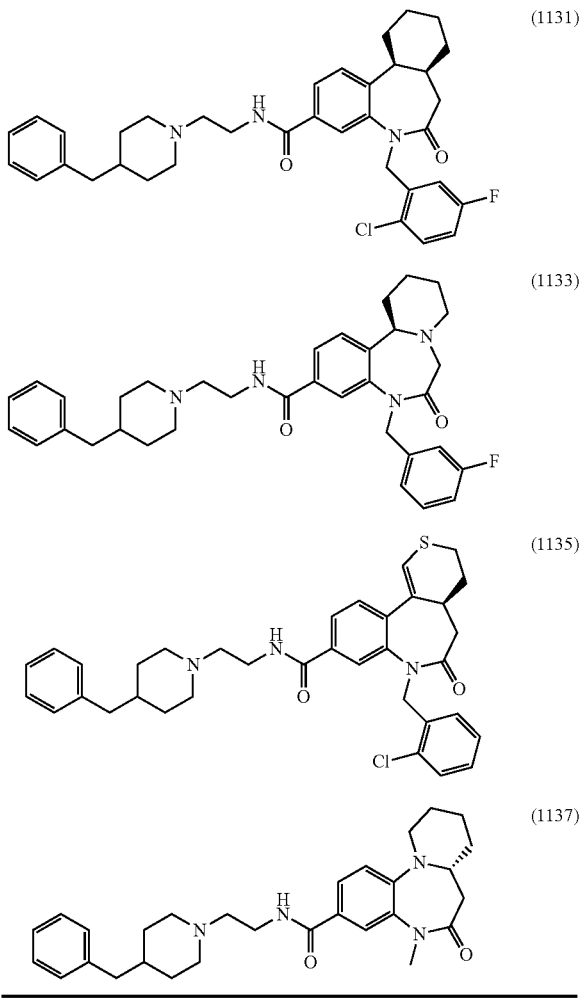

(1131)

(1133)

(1135)

(1137)

Compounds listed in Table 2.4 may also be represented by their chemical names as follows:

| ID | IUPAC Name |
|----|------------|
| 1131 | (7aS,11aS)-N-[2-(4-benzylpiperidin-1-yl)ethyl]-5-(2-chloro-5-fluorobenzyl)-6-oxo-6,7,7a,8,9,10,11,11a-octahydro-5H-dibenzo[b,d]azepine-3-carboxamide |

-continued

| ID | IUPAC Name |
|----|------------|
| 1133 | (12aR)-N-[2-(4-benzylpiperidin-1-yl)ethyl]-5-(3-fluorobenzyl)-6-oxo-5,6,7,9,10,11,12,12a-octahydropyrido[1,2-d][1,4]benzodiazepine-3-carboxamide |
| 1135 | (4aR)-N-[2-(4-benzylpiperidin-1-yl)ethyl]-7-(2-chlorobenzyl)-6-oxo-3,4,4a,5,6,7-hexahydrothiopyrano[4,3-d][1]benzazepine-9-carboxamide |
| 1137 | (7aR)-N-[2-(4-benzylpiperidin-1-yl)ethyl]-5-methyl-6-oxo-5,6,7,7a,8,9,10,11-octahydropyrido[1,2-a][1,5]benzodiazepine-3-carboxamide |

In one embodiment of formula (Vd), wherein $Z_3$—$U_4$, $U_4$—$U_5$, $U_5$—$U_6$, $U_6$—$X_4$, $A_4$-$X_4$, $Z_3$-$A_4$ together form an aromatic system.

In one embodiment of formula (Vd), the compound having the structural formula (Vd.1):

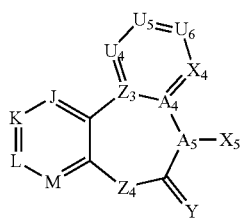

(Vd.1)

or a salt, solvate, or physiologically functional derivative thereof;

wherein:

$Z_3$ and $A_4$ are C;

$U_4$, $U_5$, $U_6$, and $X_4$ are independently N or $CR^{19}$

In one embodiment of formula (Vd.1), the compound having a structure selected from the group consisting of:

TABLE 2.5

(1141)

(1143)

TABLE 2.5-continued

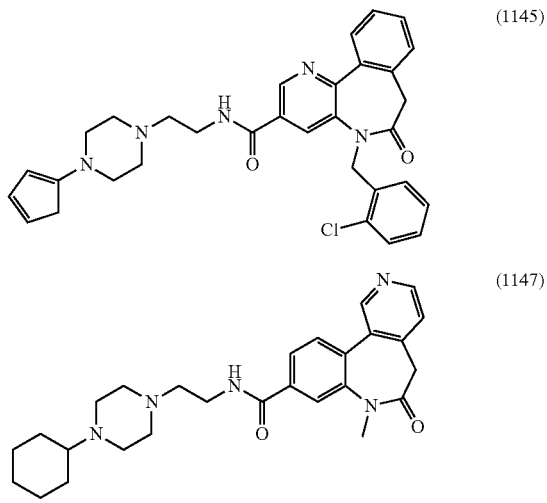

(1145)

(1147)

Compounds listed in Table 2.5 may also be represented by their chemical names as follows:

| ID | IUPAC Name |
|---|---|
| 1141 | 5-(2-chloro-5-fluorobenzyl)-6-oxo-N-[2-(4-phenylpiperazin-1-yl)ethyl]-6,7-dihydro-5H-dibenzo[b,d]azepine-3-carboxamide |
| 1143 | N-[2-(4-benzylpiperidin-1-yl)ethyl]-7-(3-fluorobenzyl)-6-oxo-6,7-dihydro-5H-pyrido[3,2-d][1]benzazepine-9-carboxamide |
| 1145 | 5-(2-chlorobenzyl)-N-{2-[4-(cyclopenta-1,3-dien-1-yl)piperazin-1-yl]ethyl}-6-oxo-6,7-dihydro-5H-pyrido[2,3-a][3]benzazepine-3-carboxamide |
| 1147 | N-[2-(4-cyclohexylpiperazin-1-yl)ethyl]-7-methyl-6-oxo-6,7-dihydro-5H-pyrido[4,3-d][1]benzazepine-9-carboxamide |

In one embodiment of formula (V), wherein $A_4$-$X_4$ and $A_5$-$X_5$ form a 5-member ring system.

In one embodiment of formula (V), the compound having the structural formula (Ve):

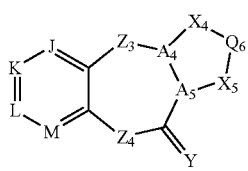

(Ve)

or a salt, solvate, or physiologically functional derivative thereof;
wherein:
$A_4$-$X_4$, $X_4$-$Q_6$, $Q_6$-$X_5$, $A_5$-$X_5$, $A_4$-$A_5$ are independently single or double bond;
$X_4$, $X_5$, and $Q_6$ are independently S, O, N, N($R^{22}$), C($R^{22}$), or C($R^{22}R^{23}$);
$A_4$ and $A_5$ are independently N, C, or C$R^{24}$;
$R^{22}$, $R^{23}$, and $R^{24}$ are independently hydrogen, halogen, acyl, substituted acyl, alkoxycarbonyl, substituted alkoxycarbonyl, aryloxycarbonyl, substituted aryloxycarbonyl, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl.

In one embodiment of formula (Ve), the compound having a structure selected from the group consisting of:

TABLE 2.6

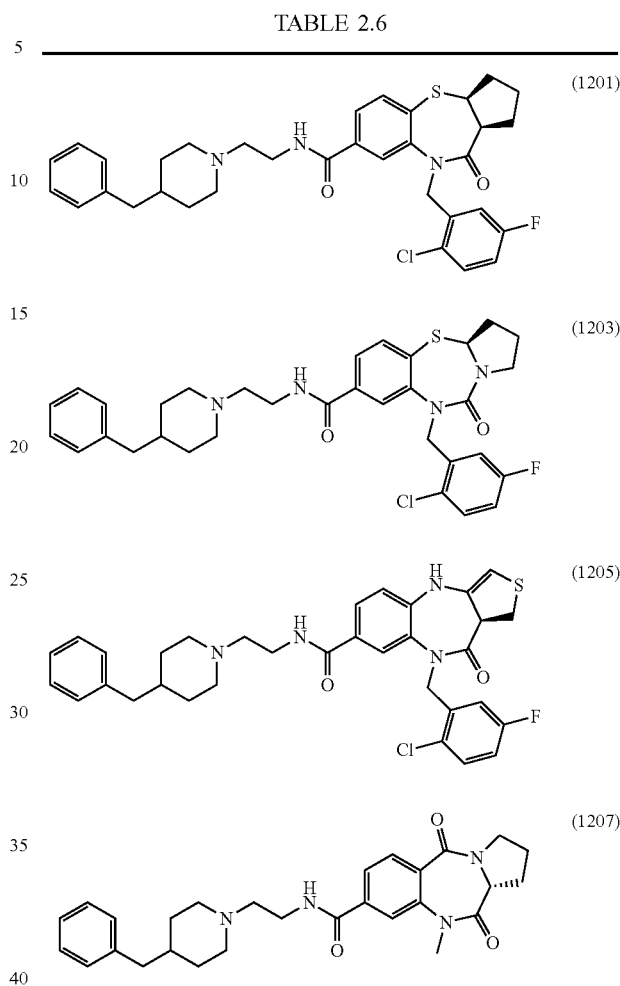

(1201)

(1203)

(1205)

(1207)

Compounds listed in Table 2.6 may also be represented by their chemical names as follows:

| ID | IUPAC Name |
|---|---|
| 1201 | (3aS,10aS)-N-[2-(4-benzylpiperidin-1-yl)ethyl]-9-(2-chloro-5-fluorobenzyl)-10-oxo-2,3,3a,9,10,10a-hexahydro-1H-benzo[b]cyclopenta[f][1,4]thiazepine-7-carboxamide |
| 1203 | (11aS)-N-[2-(4-benzylpiperidin-1-yl)ethyl]-6-(2-chloro-5-fluorobenzyl)-5-oxo-1,2,3,5,6,11a-hexahydropyrrolo[2,1-b][1,3,5]benzothiadiazepine-8-carboxamide |
| 1205 | (10aR)-N-[2-(4-benzylpiperidin-1-yl)ethyl]-9-(2-chloro-5-fluorobenzyl)-10-oxo-4,9,10,10a-tetrahydro-1H-thieno[3,4-b][1,5]benzodiazepine-7-carboxamide |
| 1207 | (11aR)-N-[2-(4-benzylpiperidin-1-yl)ethyl]-10-methyl-5,11-dioxo-2,3,5,10,11,11a-hexahydro-1H-pyrrolo[2,1-c][1,4]benzodiazepine-8-carboxamide |

In one embodiment of formula (Ve), wherein A4-X4 and Q6-X5 are double bond.

In one embodiment of formula (Ve), the compound wherein A4-A5, X4-Q6, and A5-X5 are single bond.

In one embodiment of formula (Ve), the compound having the structural formula (Ve.1):

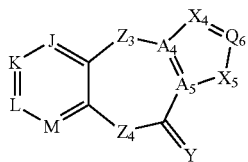
(Ve.1)

or a salt, solvate, or physiologically functional derivative thereof;
wherein:
A4 and A5 are C;
X5 is S, O, N, NR²⁴, or CR²⁴
X4, and Q₆ are independently N or CR²⁰.

In one embodiment of formula (Ve. 1), the compound having a structure selected from the group consisting of:

TABLE 2.7

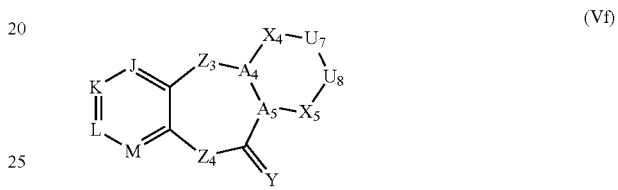

Compounds listed in Table 2.7 may also be represented by their chemical names as follows:

| ID | IUPAC Name |
|---|---|
| 1215 | 9-(2-chloro-5-fluorobenzyl)-10-oxo-N-[2-(4-phenylpiperazin-1-yl)ethyl]-9,10-dihydrothieno[3,2-b][1,5]benzothiazepine-7-carboxamide |
| 1217 | N-[2-(4-benzylpiperidin-1-yl)ethyl]-9-(2-chloro-5-fluorobenzyl)-10-oxo-9,10-dihydro-1H-[1,2,3]triazolo[4,5-b][1,5]benzoxazepine-7-carboxamide |

-continued

| ID | IUPAC Name |
|---|---|
| 1219 | 9-(2-chloro-5-fluorobenzyl)-N-{2-[4-(cyclopenta-1,3-dien-1-yl)piperazin-1-yl]ethyl}-10-oxo-9,10-dihydro-4H-furo[3,2-b][1,5]benzodiazepine-7-carboxamide |
| 1221 | N-[2-(4-cyclohexylpiperazin-1-yl)ethyl]-5-methyl-4,10-dioxo-3,4,5,10-tetrahydrobenzo[b]cyclopenta[e]azepine-7-carboxamide |

In one embodiment of formula (V), wherein A₄-X₄ and A₅-X₅ form a 6-member ring system.

In one embodiment of formula (V), the compound having the structural formula (Vf):

(Vf)

[structure]

or a salt, solvate, or physiologically functional derivative thereof;
wherein:
A4-X4, X4-U7, U7-U8, U8-X5, A5-X5, and A4-A5 are independently single or double bond;
X4, U7, U8, and X5 are independently S, O, N, N(R²⁵), C(R²⁵), or C(R²⁵R²⁶);
A4 and A5 are independently N, C, or CR²⁷
R²⁵, R²⁶, and R²⁷ are independently hydrogen, halogen, acyl, substituted acyl, alkoxycarbonyl, substituted alkoxycarbonyl, aryloxycarbonyl, substituted aryloxycarbonyl, alkyl, substituted alkyl, aryl, substituted aryl, arylalkyl, substituted arylalkyl, heteroaryl, substituted heteroaryl, heteroarylalkyl, substituted heteroarylalkyl, heteroalkyl;

In one embodiment of formula (Vf), the compound of having a structure selected from the group consisting of:

TABLE 2.8

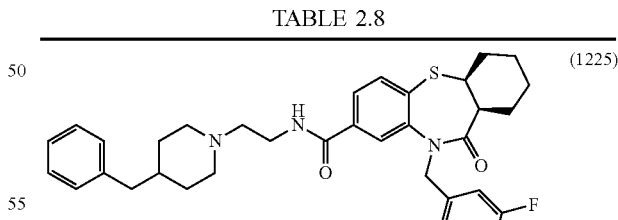

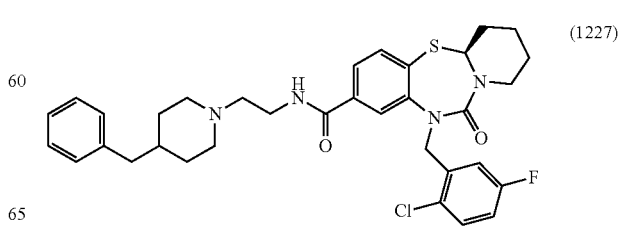

TABLE 2.8-continued

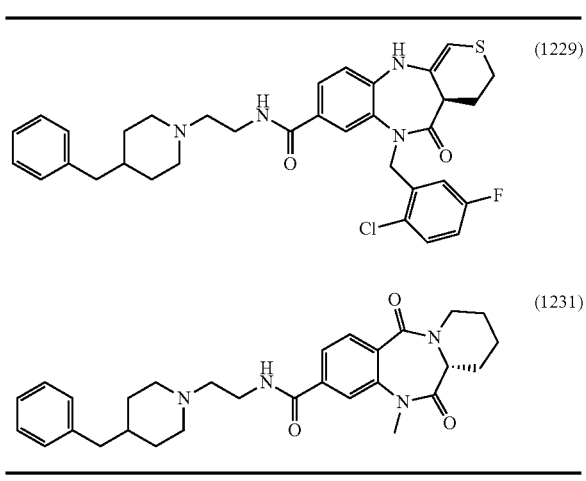

Compounds listed in Table 2.8 may also be represented by their chemical names as follows:

| ID | IUPAC Name |
|---|---|
| 1225 | (4aS,11aS)-N-[2-(4-benzylpiperidin-1-yl)ethyl]-10-(2-chloro-5-fluorobenzyl)-11-oxo-1,2,3,4,4a,10,11,11a-octahydrodibenzo[b,f][1,4]thiazepine-8-carboxamide |
| 1227 | (11aS)-N-[2-(4-benzylpiperidin-1-yl)ethyl]-5-(2-chloro-5-fluorobenzyl)-6-oxo-5,6,9,10,11,11a-hexahydro-8H-pyrido[2,1-b][1,3,5]benzothiadiazepine-3-carboxamide |
| 1229 | (4aR)-N-[2-(4-benzylpiperidin-1-yl)ethyl]-6-(2-chloro-5-fluorobenzyl)-5-oxo-3,4,4a,5,6,11-hexahydrothiopyrano[3,4-b][1,5]benzodiazepine-8-carboxamide |
| 1231 | (6aR)-N-[2-(4-benzylpiperidin-1-yl)ethyl]-5-methyl-6,12-dioxo-5,6,6a,7,8,9,10,12-octahydropyrido[2,1-c][1,4]benzodiazepine-3-carboxamide |

In one embodiment of formula (Vf), wherein A4-X4, X4-U7, U7-U8, U8-X5, A5-X5, and A4-A5 together form an aromatic system.

In one embodiment of formula (Vf), the compound having the structural formula (Vf.1):

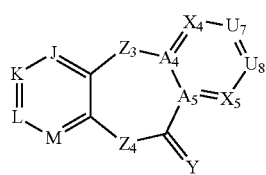

(Vf.1)

or a salt, solvate, or physiologically functional derivative thereof;

wherein:

A4 and A5 are C;

X4, U7, U8, and X5 are independently N or CR$^{25}$

In one embodiment of formula (Vf. 1), the compound having a structure selected from the group consisting of:

TABLE 2.9

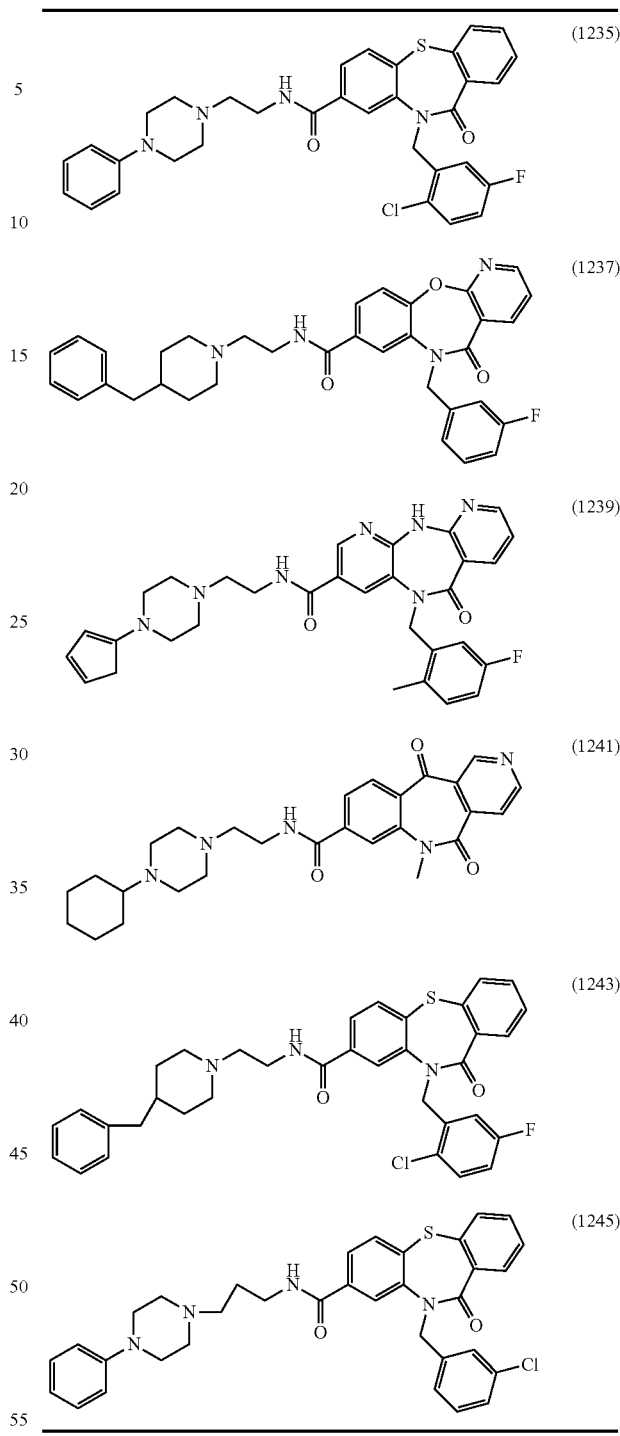

Compounds listed in Table 2.9 may also be represented by their chemical names as follows:

| ID | IUPAC Name |
|---|---|
| 1235 | 10-(2-chloro-5-fluorobenzyl)-11-oxo-N-[2-(4-phenylpiperazin-1-yl)ethyl]-10,11-dihydrodibenzo[b,f][1,4]thiazepine-8-carboxamide |
| 1237 | N-[2-(4-benzylpiperidin-1-yl)ethyl]-6-(3-fluorobenzyl)-5-oxo-5,6-dihydropyrido[2,3-b][1,5]benzoxazepine-8-carboxamide |

| ID | IUPAC Name |
|---|---|
| 1239 | N-{2-[4-(cyclopenta-1,3-dien-1-yl)piperazin-1-yl]ethyl}-5-(5-fluoro-2-methylbenzyl)-6-oxo-6,11-dihydro-5H-dipyrido[3,2-b:2',3'-e][1,4]diazepine-3-carboxamide |
| 1241 | N-[2-(4-cyclohexylpiperazin-1-yl)ethyl]-6-methyl-5,11-dioxo-6,11-dihydro-5H-pyrido[4,3-c][1]benzazepine-8-carboxamide |
| 1243 | N-[2-(4-benzylpiperidin-1-yl)ethyl]-10-(2-chloro-5-fluorobenzyl)-11-oxo-10,11-dihydrodibenzo[b,f][1,4]thiazepine-8-carboxamide |
| 1245 | 10-(3-chlorobenzyl)-11-oxo-N-[3-(4-phenylpiperazin-1-yl)propyl]-10,11-dihydrodibenzo [b,f][1,4]thiazepine-8-carboxamide |

In one embodiment of formula (I), wherein n=3, m=0, and A is "$A_{61}$-$A_{62}$-$A_{63}$".

In one embodiment of formula (I), the compound having the structural formula (VI):

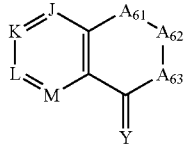

(VI)

or a salt, solvate, or physiologically functional derivative thereof;
wherein:

$A_{61}$, $A_{62}$ and $A_{63}$ are independently C, N, O, S, $NR^1$, C=$CR^1$ (E and Z isomers), C=$NR^1$ (E and Z isomers), or C($R^1R^2$);

$A_{61}$-$A_{62}$ and $A_{62}$-$A_{63}$ are independently single or double bond.

In one embodiment of formula (VI), wherein $A_{61}$ and $A_{62}$ are C, and they along with three other atoms form a 5-member ring.

In one embodiment of formula (VI), the compound having a structural formula (VIa):

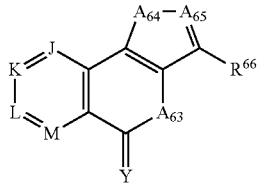

(VIa)

or a salt, solvate, or physiologically functional derivative thereof;
wherein:

$A_{64}$ is O or S;
$A_{65}$ is N or $CR^1$;
$R^{66}$ is hydrogen, alkyl, or substituted alkyl.

In one embodiment of formula (VIa), wherein $A_{63}$ is C, $A_{63}$ and $R^{66}$ along with four other atoms form a substituted 6-member aromatic ring.

In one embodiment of formula (VIa), the compound having a structural formula (VIa.1):

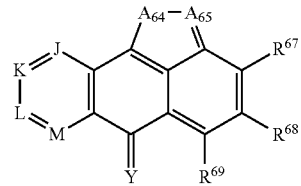

(VIa.1)

or a salt, solvate, or physiologically functional derivative thereof;
wherein:

$R^{67}$, $R^{68}$ and $R^{69}$ are independently hydrogen, halogen, acyl, substituted acyl, alkoxycarbonyl, substituted alkoxycarbonyl, aryloxycarbonyl, substituted aryloxycarbonyl, —$CONR^{70}R^{71}$, —$NR^{70}R^{71}$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl, or substituted heteroalkyl;

$R^{70}$ and $R^{71}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{70}$ and $R^{71}$, taken together with the nitrogen atom to which they are attached, form a 4-, 5-, 6-, or 7-membered cycloheteroalkyl ring;

In one embodiment of formula (VIa.1), wherein J, K, L and M are $CR^5$, $R^{68}$ is H, $R^{67}$ is a substituted 6-member cycloheteroalkyl ring, and $R^{69}$ is —$NHR^{70}$.

In one embodiment of formula (VIa.1), the compound having a structure formula (VIa.11):

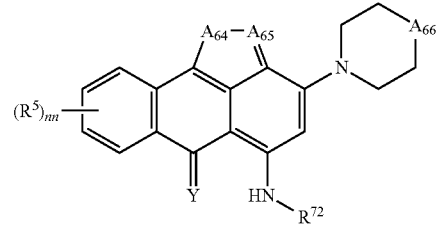

(VIa.11)

or a salt, solvate, or physiologically functional derivative thereof;
wherein nn is an integer from 0 to 4;
$A_{66}$ is $NR^{73}$, or $CR^{73}R^{74}$;
$R^{72}$, $R^{73}$, and $R^{74}$ are independently hydrogen, halogen, cyano, nitro, amino, substituted amino, sulfonyl, substituted sulfonyl, acyl, substituted acyl, alkoxycarbonyl, substituted alkoxycarbonyl, aryloxycarbonyl, substituted aryloxycarbonyl, —$CONR^{75}R^{76}$, $S(O)_2NR^{75}R^{76}$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

$R^{75}$ and $R^{76}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{75}$ and $R^{76}$, taken together with the nitrogen atom to which they are attached, form a 4-, 5-, 6-, or 7-membered cycloheteroalkyl ring.

In one embodiment of formula (VIa.11), the compounds having the following structures:
TABLE 3.0
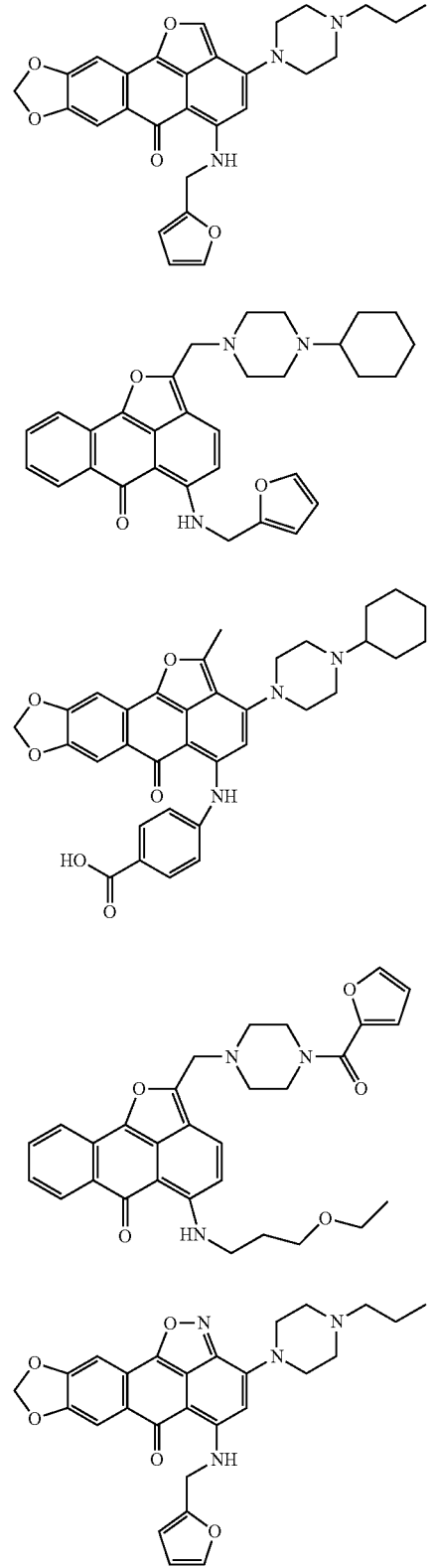
TABLE 3.0-continued
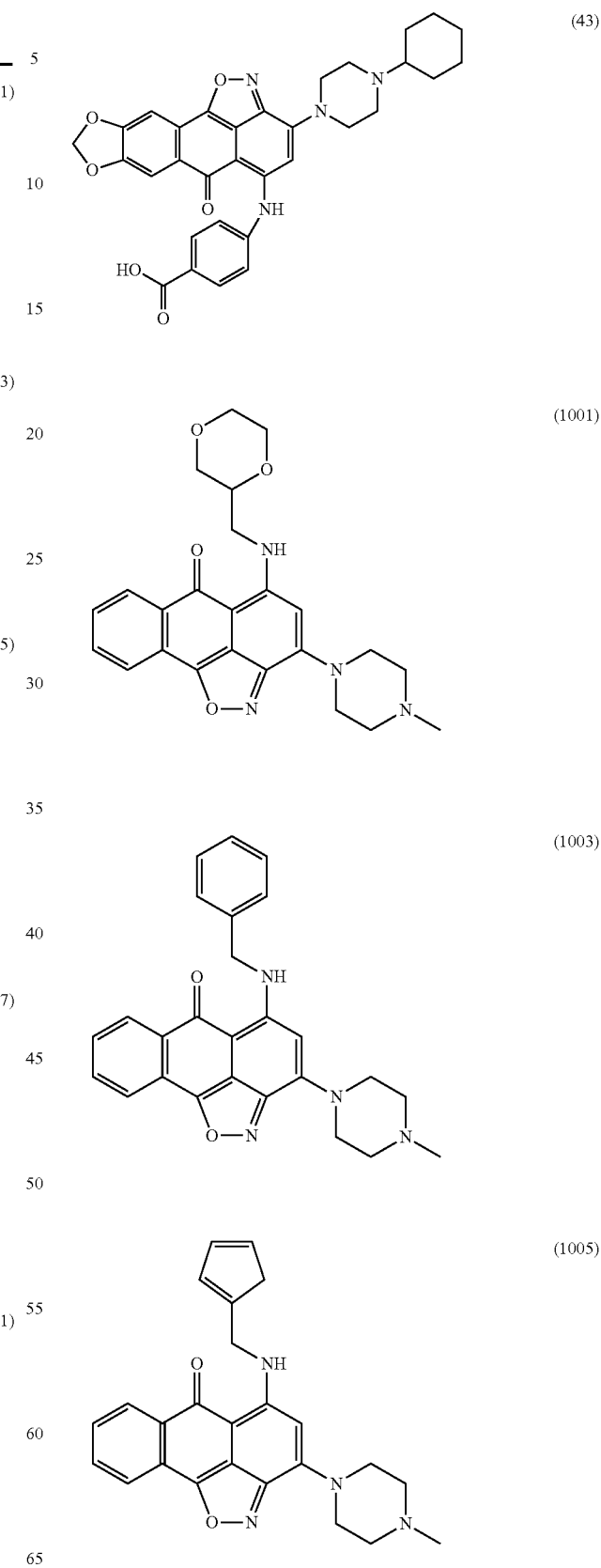

TABLE 3.0-continued
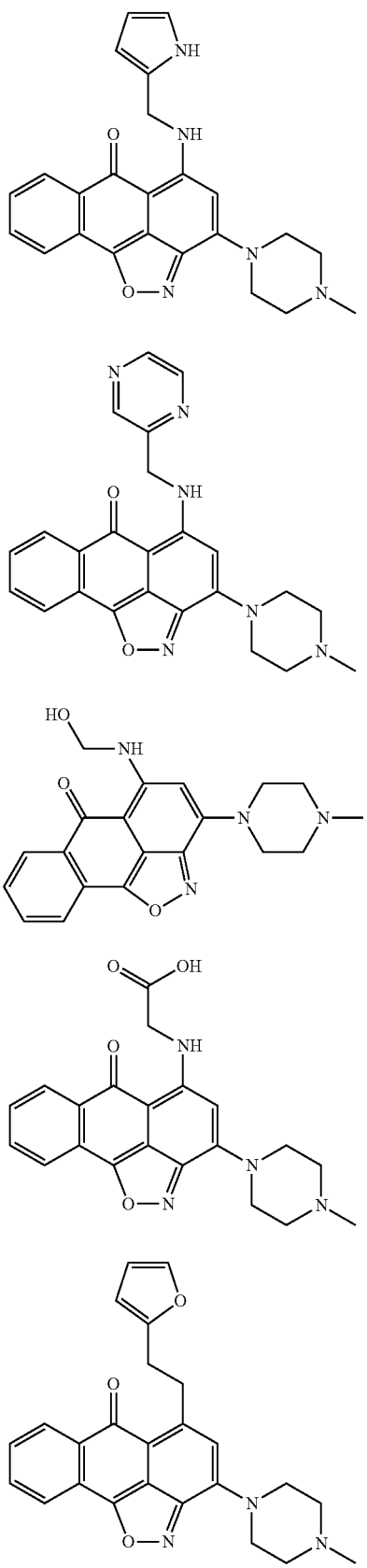
(1007)
(1009)
(1011)
(1013)
(1015)
TABLE 3.0-continued
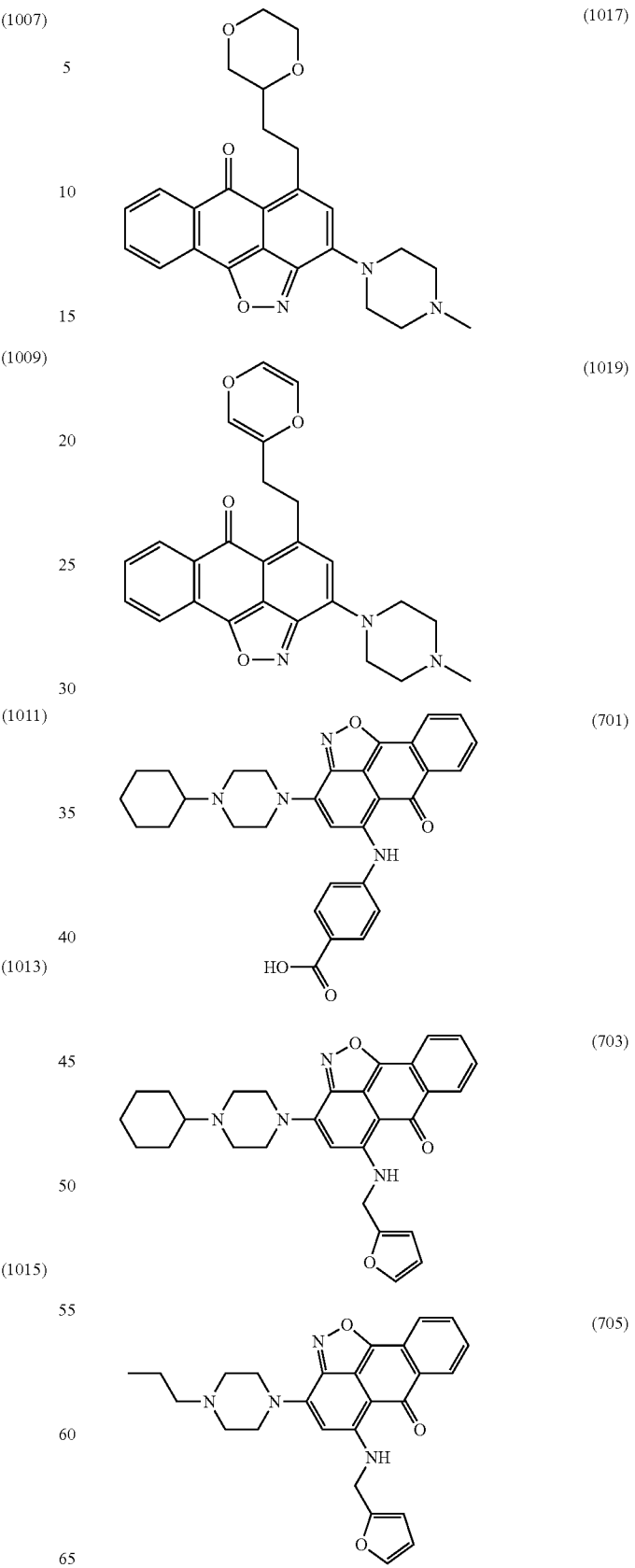
(1017)
(1019)
(701)
(703)
(705)

TABLE 3.0-continued
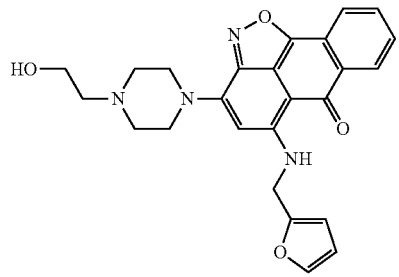 [SMILES: O=C1c2ccccc2-c2onc3c(N4CCN(CCO)CC4)cc(NCc4ccco4)c1c23] (707)
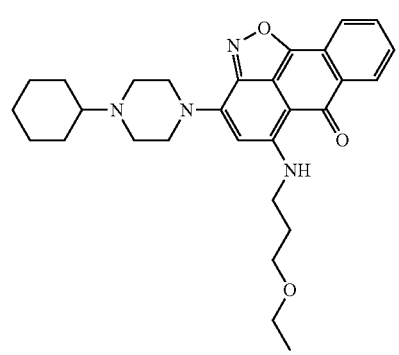 [SMILES: CCOCCCNc1cc(N2CCN(C3CCCCC3)CC2)c2noc3c2c1C(=O)c1ccccc1-3] (709)
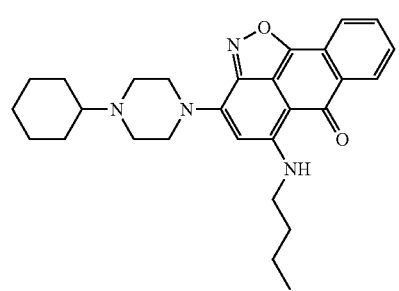 [SMILES: CCCCNc1cc(N2CCN(C3CCCCC3)CC2)c2noc3c2c1C(=O)c1ccccc1-3] (711)
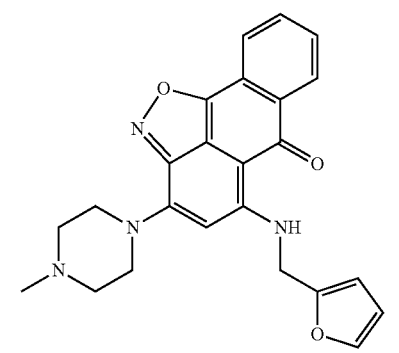 [SMILES: CN1CCN(c2cc(NCc3ccco3)c3c4c(onc24)-c2ccccc2C3=O)CC1] (713)
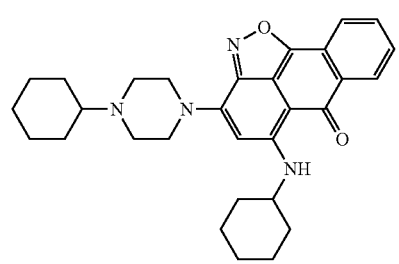 [SMILES: O=C1c2ccccc2-c2onc3c(N4CCN(C5CCCCC5)CC4)cc(NC4CCCCC4)c1c23] (715)
TABLE 3.0-continued
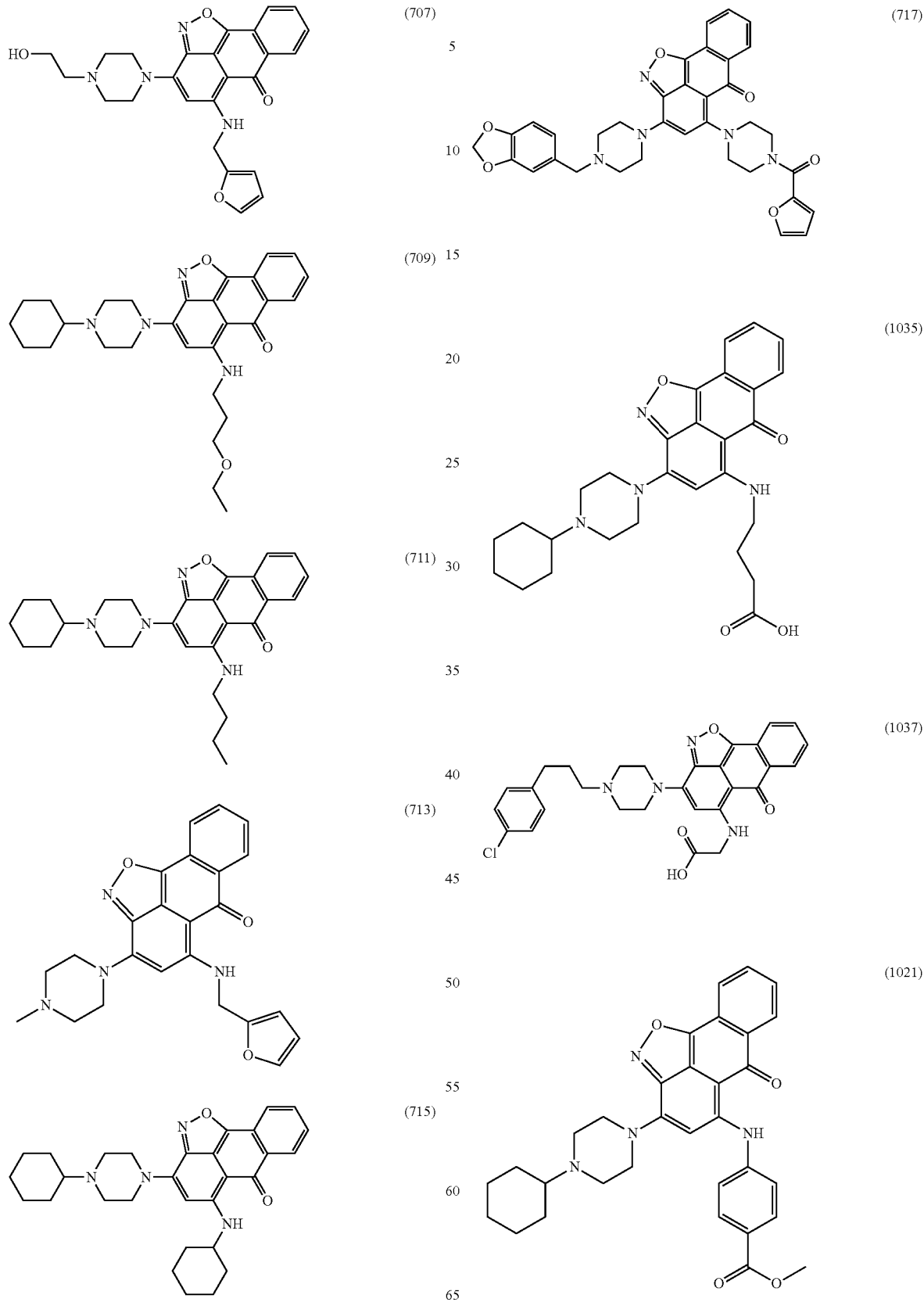

TABLE 3.0-continued
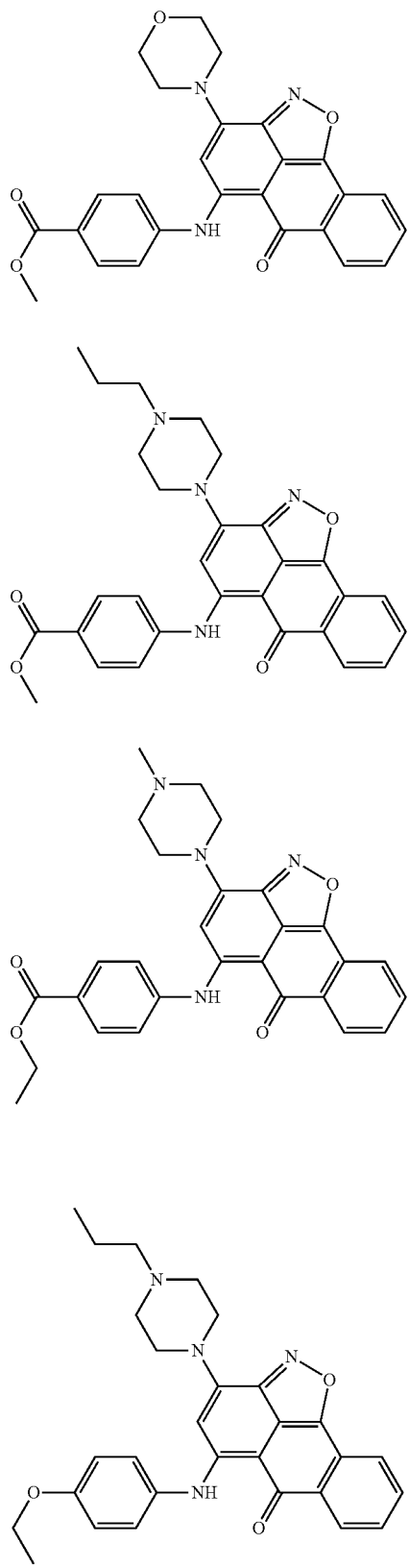
(1023)
(1025)
(1027)
(1029)
TABLE 3.0-continued
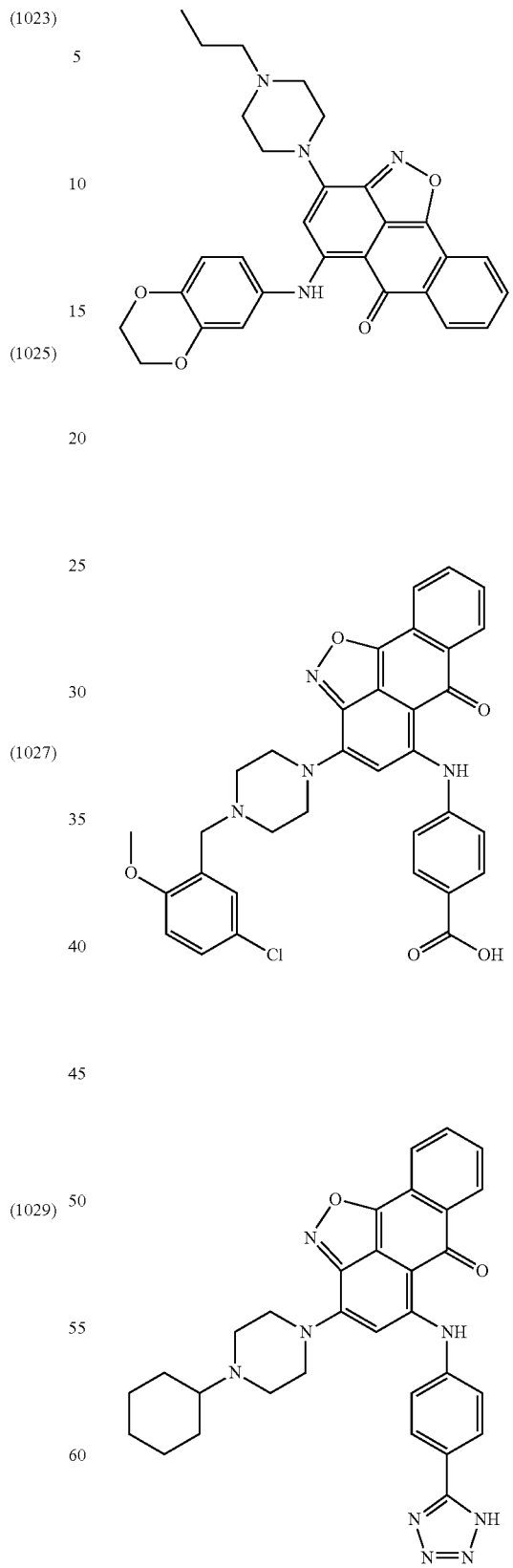
(1031)
(1033)
(1039)

TABLE 3.0-continued

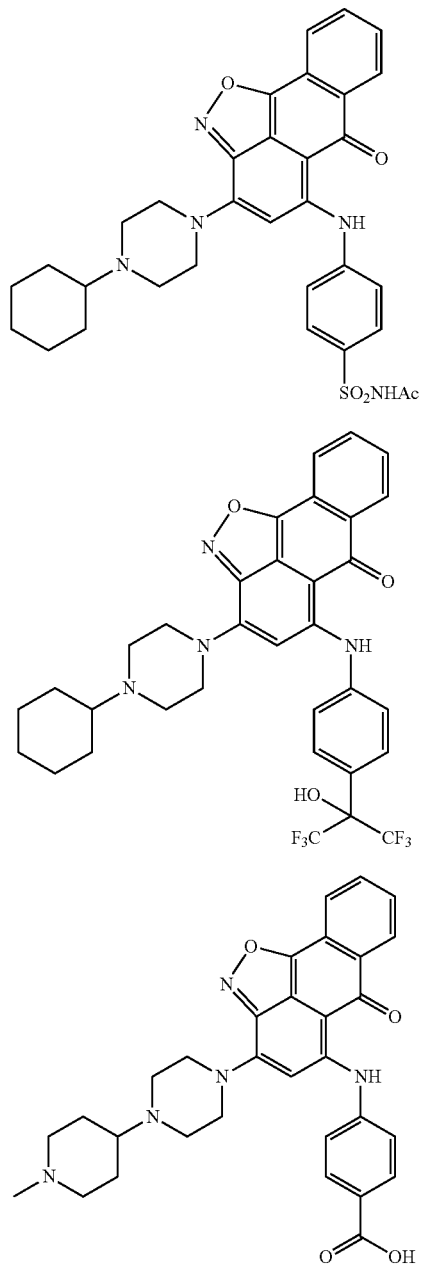

(1041)

(1043)

(1045)

Compounds listed in Table 3.0 may also be represented by their chemical names as follows:

| ID | IUPAC Name |
|---|---|
| 11 | 5-[(furan-2-ylmethyl)amino]-3-(4-propylpiperazin-1-yl)-6H-furo[4',3',2':5,10]anthra[2,3-d][1,3]dioxol-6-one |
| 13 | 2-[(4-cyclohexylpiperazin-1-yl)methyl]-5-[(furan-2-ylmethyl)amino]-6H-anthra[9,1-bc]furan-6-one |
| 15 | 4-{3-(4-cyclohexylpiperazin-1-yl)-2-methyl-6-oxo-6H-furo[4',3',2':5,10]anthra[2,3-d][1,3amino}benzoic acid |
| 17 | 5-[(3-ethoxypropyl)amino]-2-{[4-(furan-2-ylcarbonyl)piperazin-1-yl]methyl}-6H-anthra[9,1-bc]furan-6-one |
| 41 | 5-[(furan-2-ylmethyl)amino]-3-(4-propylpiperazin-1-yl)-6H-[1,3]dioxolo[6,7]anthra[1,9-cd]isoxazol-6-one |
| 43 | 4-{[3-(4-cyclohexylpiperazin-1-yl)-6-oxo-6H-[1,3]dioxolo[6,7]anthra[1,9-cd]isoxazol-5-yl]amino}benzoic acid |

| ID | IUPAC Name |
|---|---|
| 1001 | 5-[(1,4-dioxan-2-ylmethyl)amino]-3-(4-methylpiperazin-1-yl)-6H-anthra[1,9-cd]isoxazol-6-one |
| 1003 | 5-(benzylamino)-3-(4-methylpiperazin-1-yl)-6H-anthra[1,9-cd]isoxazol-6-one |
| 1005 | 5-[(cyclopenta-1,3-dien-1-ylmethyl)amino]-3-(4-methylpiperazin-1-yl)-6H-anthra[1,9-cd]isoxazol-6-one |
| 1007 | 3-(4-methylpiperazin-1-yl)-5-[(1H-pyrrol-2-ylmethyl)amino]-6H-anthra[1,9-cd]isoxazol-6-one |
| 1009 | 3-(4-methylpiperazin-1-yl)-5-[(pyrazin-2-ylmethyl)amino]-6H-anthra[1,9-cd]isoxazol-6-one |
| 1011 | 5-[(hydroxymethyl)amino]-3-(4-methylpiperazin-1-yl)-6H-anthra[1,9-cd]isoxazol-6-one |
| 1013 | N-[3-(4-methylpiperazin-1-yl)-6-oxo-6H-anthra[1,9-cd]isoxazol-5-yl]glycine |
| 1015 | 5-[2-(furan-2-yl)ethyl]-3-(4-methylpiperazin-1-yl)-6H-anthra[1,9-cd]isoxazol-6-one |
| 1017 | 5-[2-(1,4-dioxan-2-yl)ethyl]-3-(4-methylpiperazin-1-yl)-6H-anthra[1,9-cd]isoxazol-6-one |
| 1019 | 5-[2-(1,4-dioxin-2-yl)ethyl]-3-(4-methylpiperazin-1-yl)-6H-anthra[1,9-cd]isoxazol-6-one |
| 701 | 4-{[3-(4-cyclohexylpiperazin-1-yl)-6-oxo-6H-anthra[1,9-cd]isoxazol-5-yl]amino}benzoic acid |
| 703 | 3-(4-cyclohexylpiperazin-1-yl)-5-[(furan-2-ylmethyl)amino]-6H-anthra[1,9-cd]isoxazol-6-one |
| 705 | 5-[(furan-2-ylmethyl)amino]-3-(4-propylpiperazin-1-yl)-6H-anthra[1,9-cd]isoxazol-6-one |
| 707 | 5-[(furan-2-ylmethyl)amino]-3-[4-(2-hydroxyethyl)piperazin-1-yl]-6H-anthra[1,9-cd]isoxazol-6-one |
| 709 | 3-(4-cyclohexylpiperazin-1-yl)-5-[(3-ethoxypropyl)amino]-6H-anthra[1,9-cd]isoxazol-6-one |
| 711 | 5-(butylamino)-3-(4-cyclohexylpiperazin-1-yl)-6H-anthra[1,9-cd]isoxazol-6-one |
| 713 | 5-[(furan-2-ylmethyl)amino]-3-(4-methylpiperazin-1-yl)-6H-anthra[1,9-cd]isoxazol-6-one |
| 715 | 5-(cyclohexylamino)-3-(4-cyclohexylpiperazin-1-yl)-6H-anthra[1,9-cd]isoxazol-6-one |
| 717 | 3-[4-(1,3-benzodioxol-5-ylmethyl)piperazin-1-yl]-5-[4-(furan-2-ylcarbonyl)piperazin-1-yl]-6H-anthra[1,9-cd]isoxazol-6-one |
| 1021 | methyl 4-{[3-(4-cyclohexylpiperazin-1-yl)-6-oxo-6H-anthra[1,9-cd]isoxazol-5-yl]amino}benzoate |
| 1023 | methyl 4-{[3-(morpholin-4-yl)-6-oxo-6H-anthra[1,9-cd]isoxazol-5-yl]amino}benzoate |
| 1025 | methyl 4-{[6-oxo-3-(4-propylpiperazin-1-yl)-6H-anthra[1,9-cd]isoxazol-5-yl]amino}benzoate |
| 1027 | ethyl 4-{[3-(4-methylpiperazin-1-yl)-6-oxo-6H-anthra[1,9-cd]isoxazol-5-yl]amino}benzoate |
| 1029 | 5-[(4-ethoxyphenyl)amino]-3-(4-propylpiperazin-1-yl)-6H-anthra[1,9-cd]isoxazol-6-one |
| 1031 | 5-(2,3-dihydro-1,4-benzodioxin-6-ylamino)-3-(4-propylpiperazin-1-yl)-6H-anthra[1,9-cd]isoxazol-6-one |
| 1033 | 4-({3-[4-(5-chloro-2-methoxybenzyl)piperazin-1-yl]-6-oxo-6H-anthra[1,9-cd]isoxazol-5-yl}amino)benzoic acid |
| 1035 | 4-{[3-(4-cyclohexylpiperazin-1-yl)-6-oxo-6H-anthra[1,9-cd]isoxazol-5-yl]amino}butanoic acid |
| 1037 | N-(3-{4-[3-(4-chlorophenyl)propyl]piperazin-1-yl}-6-oxo-6H-anthra[1,9-cd]isoxazol-5-y)glycine |
| 1039 | 3-(4-cyclohexylpiperazin-1-yl)-5-{[4-(1H-tetrazol-5-yl)phenyl]amino}-6H-anthra[1,9-cd]isoxazol-6-one |
| 1041 | N-(4-{[3-(4-cyclohexylpiperazin-1-yl)-6-oxo-6H-anthra[1,9-cd]isoxazol-5-yl]phenyl}sulfonyl)acetamide |
| 1043 | 3-(4-cyclohexylpiperazin-1-yl)-5-{[4-(1,1,1,3,3,3-hexafluoro-2-hydroxypropan-2-yl)phenyl]amino}-6H-anthra[1,9-cd]isoxazol-6-one |
| 1045 | 4-({3-[4-(1-methylpiperidin-4-yl)piperazin-1-yl]-6-oxo-6H-anthra[1,9-cd]isoxazol-5-yl}amino)benzoic acid |

5.3 Synthesis of the Compounds

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyl-lithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; Et₃N: triethylamine; DCM: dichloromethane; DCE: dichloroethane; DME: dimethoxyethane; DBA: diethylamine; DAST: diethylaminosulfur trifluoride; EtMgBr: ethylamgnesium bromide; BSA: bovine serum albumin; TFA: trifluoracetic acid; DMF: N,N-dimethylformamide; SOCl₂: thionyl chloride; CDI: carbonyl diirnidazole; rt: room temperature; HPLC: high performance liquid chromatography; TLC: thin-layer chromatography. The compounds described herein may be prepared in a variety of ways known to one skilled in the art.

The procedures described herein for synthesizing compounds the present invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^{1}$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

Scheme 1. Examples of General Reaction Scheme for Formula IVd (compound 481):

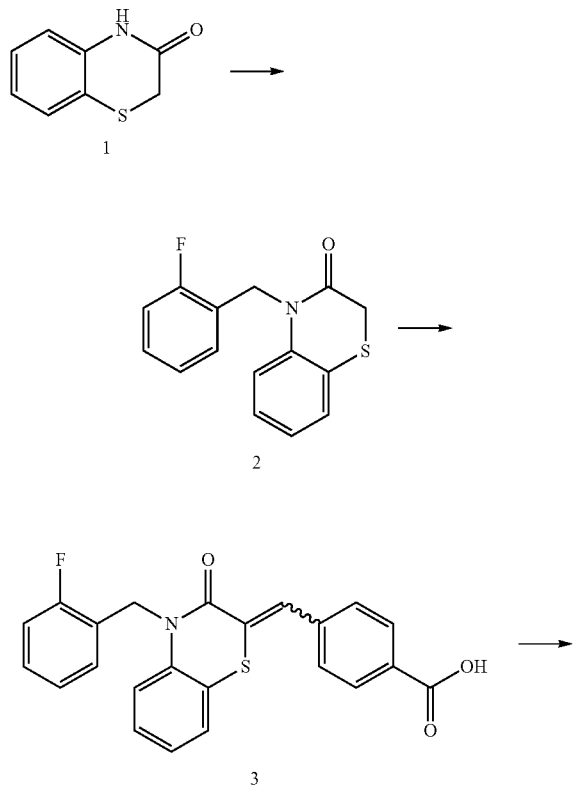

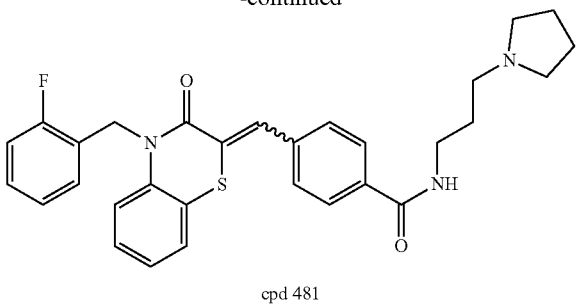

cpd 481

4-(2-fluorobenzyl)-2H-benzo[b][1,4]thiazin-3 (4H)-one (2)

To a mixture of 2H-benzo[b][1,4]thiazin-3(4H)-one (1.0 g, 6.1 mmole) and 1-(bromomethyl)-2-fluorobenzene (0.76 mL, 1.05 equiv) in DMF (10 mL) was added t-BuOK (0.75 g) at 0° C. The reaction mixture was warmed to room temperature and stirred overnight. Water was added and the resulted solid was filtrated, rinsed with water, and dried under vacuum to provide 4-(2-fluorobenzyl)-2H-benzo[b][1,4]thiazin-3(4H)-one (1.51 g, 91%).

4-((Z)-(4-(2-fluorobenzyl)-3,4-dihydro-3-oxobenzo[b][1,4]thiazin-2-ylidene)methyl)benzoic Acid (3)

4-(2-fluorobenzyl)-2H-benzo[b][1,4]thiazin-3 (4H)-one (1 g, 3.66 mmole) and methyl 4-formylbenzoate (1.2 g) were dissolved in THF (20 mL) and to the solution was added NaOEt (1 g). The reaction solution was heated at 70° C. overnight and aqueous HCl (5%, 10 mL) was added to quench the reaction. The mixture was extracted with EtOAc (50 mL) twice and combined organic layers were dried over anhydrous magnesium sulfate. After filtration, the solvent was removed under vacuum to give 4-((Z)-(4-(2-fluorobenzyl)-3,4-dihydro-3-oxobenzo[b][1,4]thiazin-2-ylidene) methyl)benzoic acid (1.13 g, 71%).

4-((Z)-(4-(2-fluorobenzyl)-3,4-dihydro-3-oxobenzo[b][1,4]thiazin-2-ylidene)methyl)-N-(3-(pyrrolidin-1-yl)propyl)benzamide (cpd 481)

To a solution of 4-((Z)-(4-(2-fluorobenzyl)-3,4-dihydro-3-oxobenzo[b][1,4]thiazin-2-ylidene)methyl)benzoic acid (704 mg, 1.74 mmole) and DMF (2 drops) in Methylene chloride (10 mL) was added (COCl)₂ (0.23 mL) dropwise. The reaction solution was stirred at room temperature for 1 h and the solvent was evaporated to give the acid chloride. To another solution of 3-(pyrrolidin-1-yl)propan-1-amine (267 mg) and DIPEA (0.3 mL) in Methylene chloride (10 mL) was added the above acid chloride in Methylene chloride (10 mL). The mixture was stirred at room temperature for 6 h. The solution was washed with saturated sodium bicarbonate (50 mL), water (50 mL) and dried over anhydrous magnesium sulfate. After filtration, the residue was purified through chromatography (CH2Cl2:MeOH 5:1) to give 4-((Z)-(4-(2-fluorobenzyl)-3,4-dihydro-3-oxobenzo[b][1,4]thiazin-2-ylidene)methyl)-N-(3-(pyrrolidin-1-yl)propyl)benzamide (797 mg, 89%). HNMR (300 MHz, CD₃OD), ppm: 7.94 (d, 2H), 7.89 (s, 1H), 7.77 (d, 2H), 7.36-7.25 (m 2H), 7.16 (m, 2H), 7.12-7.02 (m, 4H), 5.44 (s, 2H), 3.52 (t, 2H), 3.30 (m, 4H), 3.14 (t, 2H), 2.15-1.98 (m, 6H). LCMS (ESI+) M/z: 516 (M+H)

Scheme 2. Examples of General Reaction Scheme for Formula IVb (compound 289):

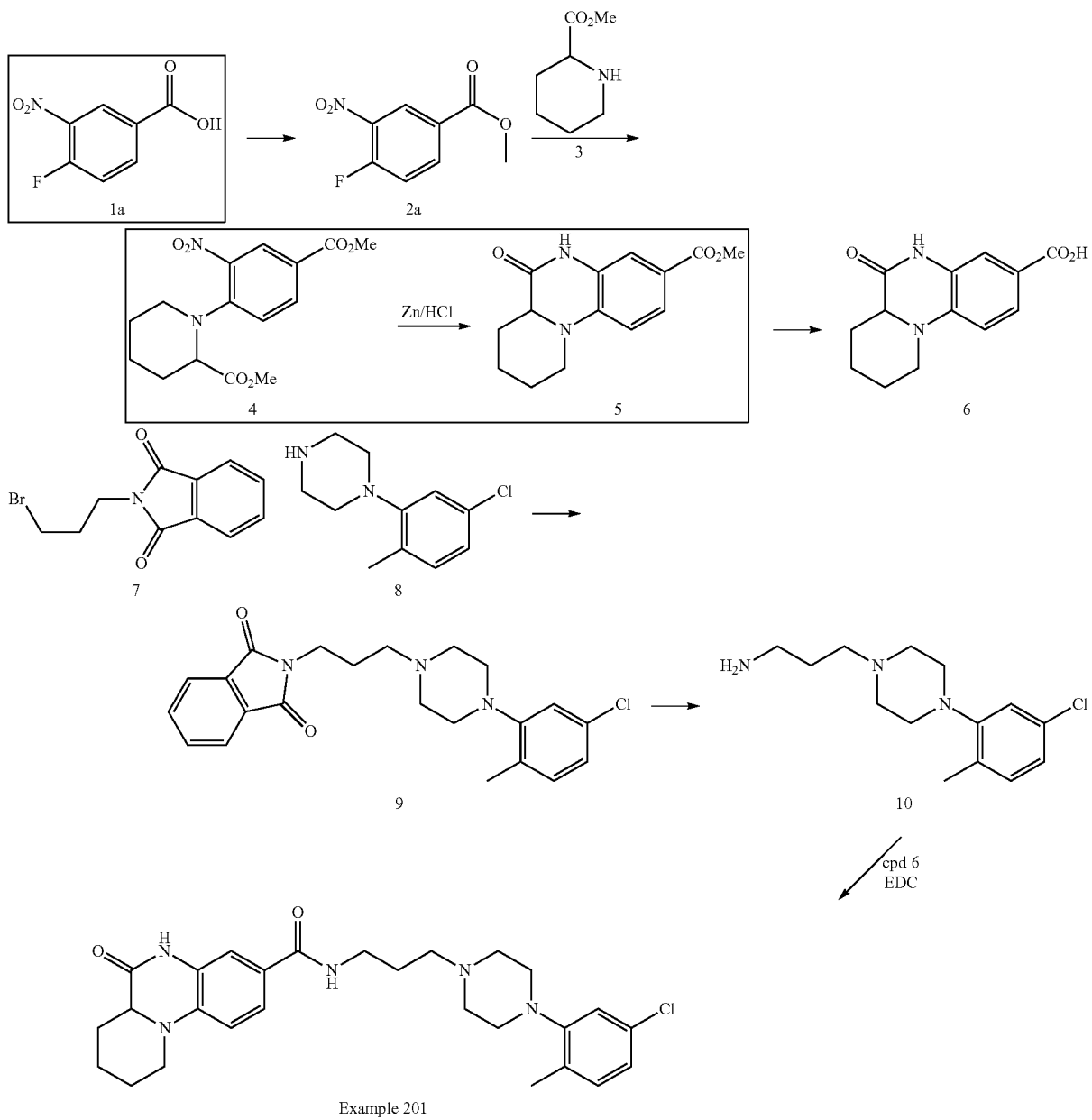

Example 201

Methyl 1-(4-(methoxycarbonyl)-2-nitrophenyl)piperidine-2-carboxylate (4)

To a mixture of methyl 4-fluoro-3-nitrobenzoate (6.46 g, 32.5 mmole) and methyl piperidine-2-carboxylate (5.57 g, 1.2 equiv) in DMF (80 mL) was added $Cs_2CO_3$ (12.7 g). The reaction mixture was stirred at 55° C. overnight. The solid was filtered and the filtrate was evaporated. The residue was recrystallized with EtOAc/Hexane to give Methyl 1-(4-(methoxycarbonyl)-2-nitrophenyl)piperidine-2-carboxylate (9.4 g, 90%).

Methyl 6,6a,7,8,9,10-hexahydro-6-oxo-5H-pyrido[1,2-a]quinoxaline-3-carboxylate (5)

Methyl 1-(4-(methoxycarbonyl)-2-nitrophenyl)piperidine-2-carboxylate (1.3 g, 4.0 mmole) was dissolved in EtOAc (20 mL) and 1N HCl (20 mL) and to the solution was added Zinc (0.80 g). The reaction mixture was reflux overnight then cooled to room temperature. The organic layer was washed with water and dried over anhydrous magnesium sulfate. After filtration, the solvent was removed to give Methyl 6,6a,7,8,9,10-hexahydro-6-oxo-5H-pyrido[1,2-a]quinoxaline-3-carboxylate (0.92 g, 88%).

6,6a,7,8,9,10-hexahydro-6-oxo-5H-pyrido[1,2-a]quinoxaline-3-carboxylic acid (6)

Methyl 6,6a,7,8,9,10-hexahydro-6-oxo-5H-pyrido[1,2-a]quinoxaline-3-carboxylate (0.762 g, 0.29 mmole) and LiOH (0.25 g) were suspended in MeOH (5 mL), THF (5 ml) and Water (2 mL). The mixture was stirred at room temperature overnight. The reaction was evaporated to near dryness, and 2N HCl was added to adjust the PH about 2. The solid was filtered and dried to provide 6,6a,7,8,9,10-hexahydro-6-oxo-5H-pyrido[1,2-a]quinoxaline-3-carboxylic acid as white solid (0.72 g, 100%). 2-(3-(4-(5-chloro-2-methylphenyl)piperazin-1-yl)propyl)isoindoline-1,3-dione (9) A mixture of 2-(3-bromopropyl)isoindoline-1,3-dione (2.68 g, 10 mmol) and NaI (20 mmol) in acetone was refluxed for 5 h, then to it was added 1-(5-chloro-2-methylphenyl)piperazine (2.11 g, 10.0 mmol). The reflux was continued for 12 h. Reaction was then cooled to room temperature, filtered through celite and concentrated. The crude product was recrystalized from acetone to give the title compound as a white solid (3.21 g, 81%).

3-(4-(5-chloro-2-methylphenyl)piperazin-1-yl)propan-1-amine (10)

A solution of 2-(3-(4-(5-chloro-2-methylphenyl)piperazin-1-yl)propyl)isoindoline-1,3-dione (397 mg, 1.0 mmol) and hydrazine monohydrate (52 mg, 1.04 mmol) in ethanol (5 mL) was heated at 70° C. for 12 h. After the reaction cooled to room temperature, the solid was filtered off, and filtrate was evaporated to give the title compound, used without further purification.

(6aS/R)—N-{3-[4-(5-chloro-2-methylphenyl)piperazin-1-yl]propyl}-6-oxo-6,6a,7,8,9,10-hexahydro-5H-pyrido[1,2-a]quinoxaline-3-carboxamide (cpd 201)

To a solution of 6,6a,7,8,9,10-hexahydro-6-oxo-5H-pyrido[1,2-a]quinoxaline-3-carboxylic acid (200 mg, 0.80 mmole), 3-(4-(5-chloro-2-methylphenyl)piperazin-1-yl)propan-1-amine (1.0 mmol), DMAP (10 mg) and DIPEA (0.30 mL) in DMF (5 mL) was added EDC (0.377 g, 2.0 mmole). The reaction solution was stirred at room temperature overnight. The solvent removed and EtOAc (60 mL) was added. The organic layer was washed with saturated sodium bicarbonate (10 mL), water (10 mL) and dried over anhydrous magnesium sulfate. After filtration and concentration, the residue was purified by column chromatography with 0-10% methanol in dichloromethane to provide the N-(3-(4-(5-chloro-2-methylphenyl)piperazin-1-yl)propyl)-6,6a,7,8,9,10-hexahydro-6-oxo-5H-pyrido[1,2-a]quinoxaline-3-carboxamide as white solid (6.28 g, 78%). $^1$HNMR (300 MHz, dmso-d6), ppm: 10.48 (s, 1H), 8.27 (t, 1H), 7.41 (dd, 1H), 7.29 (d, 1H), 7.15 (d, 1H), 6.97 (d, 1H), 6.96 (s, 1H), 6.83 (d, 1H), 3.83 (d, 1H), 3.57 (dd, 1H), 3.26 (q, 2H), 2.84 (m, 4H), 2.73 (dt, 1H), 2.40 (t, 2H), 2.20 (s, 3H), 2.00 (m, 1H), 1.83 (m, 1H), 1.69 (m, 3H), 1.52-1.33 (m, 3H). MS (ESI+) M/z: 496, 498 (M+H).

Scheme 3. Example of General Reaction Scheme for Formula VI compound 703:

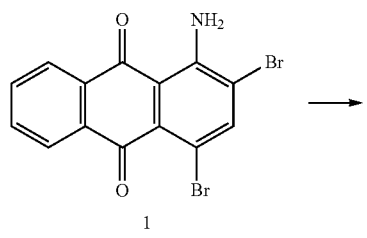

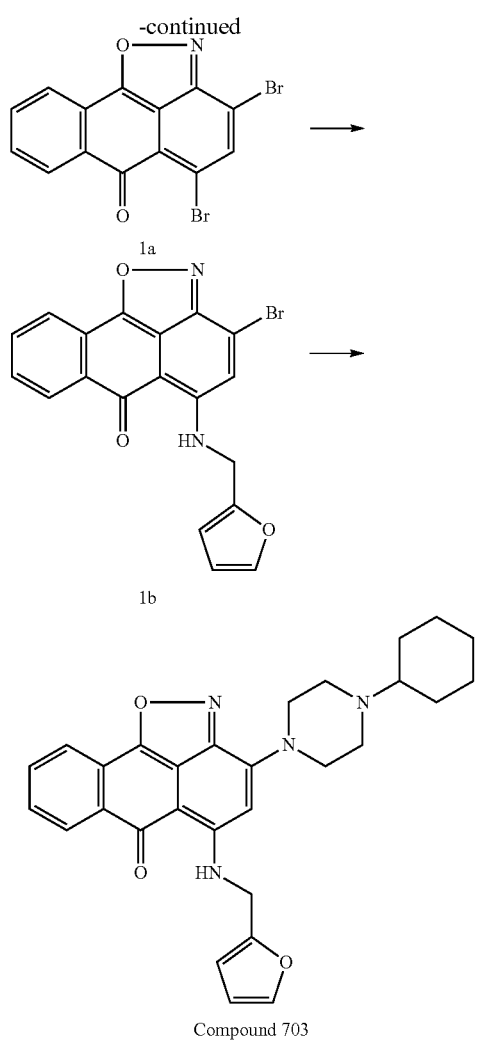

Compound 703

The synthesis of compound 703 was carried out as: NaNO$_2$ (0.57 g, 8.3 mmol) was added to 5.2 mL concentrated H$_2$SO$_4$ at 30-40° C. over 20 minutes. The mixture was stirred for 30 minutes. Then 2.9 g compound 1 was added to the solution and the solution was stirred for 4 hours at 50-55° C. The resulting solution was poured into ice (50 g) and the yellow precipitate was filtered, washed with 50 mL ice-water, followed by 150 mL 1:1 mixture of ethanol-ether. The wet filter cake was added to a solution of NaN$_3$ (0.78 g, 12 mmol) in 100 mL of water and stirred for 30 minutes. The product was filtered, washed with 100 mL water, followed by 50 mL of a mixture (9:1) of acetone and water. The product was suspended in 30 mL toluene and heated to 70° C. for 8 hours. Then the suspension was filtered, washed with 50 mL of methanol and dried to give yellow solid.

$^1$HNMR (400 MHz, CCl4 and DMSO-d6), ppm: 10.31 (br t, 1H), 8.45 (d, 1H), 8.06 (d, 1H), 7.63 (m, 1H), 7.54 (m, 1H), 7.46 (s, 1H), 6.41 (d, 1H), 6.36 (d, 1H), 6.08 (s, 1H), 4.75 (d, 2H), 3.94 (m, 4H), 2.59 (m, 4H), 2.38 (m, 2H), 1.60 (m, 2H), 0.89 (t, 3H).

Examples for Spectral Information for Other Compounds

Compound 205: $^1$HNMR (400 MHz, CCl4 and DMSO-d6), ppm: 7.87 (d, 1H), 7.69 (s, 1H), 7.66 (dd, 1H), 7.28 (d, 1H), 7.20 (m, 3H), 7.13-6.96 (m, 7H), 4.50 (s, 2H) 3.94 (s, 3H), 3.18 (q, 2H), 2.83 (m, 2H), 2.49 (t, 2H), 2.26 (m, 2H), 1.80-1.11 (m, 9H).

Compound 207: $^1$HNMR (400 MHz, CCl4 and DMSO-d6), ppm: 8.00 (br s, 1H), 7.91 (d, 2H), 7.89 (s, 1H), 7.32-6.94 (m, 8H), 5.32 (s, 2H), 3.33 (q, 2H), 2.55 (t, 2H), 2.43 (m, 4H), 1.45-1.25 (m, 8H), 0.82 (t, 6H).

Compound 209: $^1$HNMR (400 MHz, CCl4 and DMSO-d6), ppm: 77.95 (br s, 1H), 7.73 (s, 1H), 7.62 (s, 1H), 7.55 (d, 1H) 7.43 (t, 1H), 7.33 (d, 1H), 7.26 (d, 1H), 7.22-7.14 (m, 3H), 7.10-6.95 (m, 5H), 4.52 (s, 2H), 3.14 (q, 2H), 2.80 (m, 2H), 2.47 (m, 2H), 2.45 (m, 2H), 1.77 (m, 2H), 1.55 (m, 4H), 1.43 (m, 1H), 1.18 (m, 2H).

Compound 211: $^1$HNMR (400 MHz, DMSO-d6), ppm: 8.23 (t, 1H), 7.84 (s, 1H), 7.62 (m, 3H), 7.42 (m, 3H), 7.34 (m, 3H), 7.26 (d, 1H), 7.01 (t, 2H), 5.40 (s, 2H), 3.23 (q, 2H), 2.40 (m, 2H), 2.28 (m, 1H), 2.15 (s, 3H), 1.75-1.50 (m, 7H), 1.20-1.00 (m, 5H).

Compound 213: $^1$HNMR (400 MHz, CCl4 and DMSO-d6), ppm: 8.31 (br s, 1H), 7.85 (s, 1H), 7.62 (m, 2H), 7.55 (s, 1H), 7.50-7.25 (m, 5H), 7.21-6.95 (m, 9H), 5.37 (s, 2H), 3.10 (m, 2H), 2.79 (m, 2H), 2.48 (m, 2H), 2.30 (s, 3H), 2.25 (m, 2H), 1.78 (m, 2H), 1.70-1.35 (m, 5H), 1.19 (m, 2H).

Compound 215: $^1$HNMR (400 MHz, DMSO-d6), ppm: 8.29 (br s, 1H), 7.87 (s, 1H), 7.62 (m, 2H), 7.52 (s, 1H), 7.42 (m, 3H), 7.30 (m, 7.33 (m, 1H), 7.26 (m, 1H), 7.13 (m, 1H), 7.10-6.93 (m, 3H), 5.33 (s, 2H), 3.18 (m, 2H), 2.40 (m, 2H), 2.26 (s, 3H), 2.22 (m, 1H), 2.10 (s, 3H), 1.69 (m, 4H), 1.57 (m, 3H), 1.20-1.00 (m, 5H).

Compound 217: $^1$HNMR (400 MHz, CCl4 and DMSO-d6), ppm: 7.95 (t, 1H), 7.78 (s, 1H), 7.74 (s, 1H), 7.61 (d, 1H), 7.49 (d, 1H), 7.37 (t, 1H), 7.27 (d, 1H), 7.24-7.14 (m, 3H), 7.12-6.98 (m, 5H), 4.54 (s, 2H), 3.17 (q, 2H), 2.81 (m, 2H), 2.47 (m, 2H), 2.26 (m, 2H), 1.77 (m, 2H), 1.55 (m, 4H), 1.45 (m, 1H), 1.20 (m, 2H).

Compound 219: $^1$HNMR (400 MHz, DMSO-d6), ppm: 8.06 (br s, 1H), 7.58 (s, 1H), 7.63 (d, 2H), 7.58 (s, 1H), 7.44 (m, 3H), 7.35 (m, 1H), 7.27 (d, 1H), 7.17 (t, 1H), 7.11 (s, 1H), 7.08 (d, 1H), 7.00 (d, 1H), 5.38 (s, 2H), 3.32 (m, 2H), 2.65 (m, 6H), 2.31 (s, 3H), 1.55 (m, 8H).

Compound of the disclosure: $^1$HNMR (400 MHz, DMSO-d6), ppm: 10.16 (br s, 1H), 8.42 (d, 1H), 8.06 (d, 1H), 7.63 (m, 1H), 7.52 (m, 1H), 5.96 (s, 1H), 3.79 (m, 4H), 3.54 (m, 6H), 2.69 (m, 4H), 2.31 (m, 1H), 1.95 (m, 2H), 1.61 (m, 4H), 1.62 (m, 1H), 1.20 (m, 8H).

Compound of the disclosure: $^1$HNMR (400 MHz, CCl4 and DMSO-d6), ppm: 10.31 (br t, 1H), 8.45 (d, 1H), 8.06 (d, 1H), 7.63 (m, 1H), 7.54 (m, 1H), 7.46 (s, 1H), 6.41 (d, 1H), 6.36 (d, 1H), 6.08 (s, 1H), 4.74 (d, 2H), 3.94 (m, 4H), 2.73 (m, 4H), 2.31 (m, 1H), 1.81 (m, 4H), 1.62 (m, 1H), 1.15 (m, 5H).

Compound of the disclosure: $^1$HNMR (400 MHz, CCl4 and DMSO-d6), ppm: 10.31 (br t, 1H), 8.45 (d, 1H), 8.06 (d, 1H), 7.63 (m, 1H), 7.54 (m, 1H), 7.46 (s, 1H), 6.41 (d, 1H), 6.36 (d, 1H), 6.06 (s, 1H), 4.78 (d, 2H), 3.94 (m, 4H), 3.84 (M, 1H), 3.57 (m, 2H), 2.67 (m, 4H), 2.52 (m, 2H).

Compound of the disclosure: $^1$HNMR (400 MHz, CDCl3), ppm: 11.92 (s, 1H), 8.58 (d, 1H), 8.14 (m, 3H), 7.76 (t, 1H), 7.66 (t, 1H), 7.47 (d, 2H), 6.40 (s, 1H), 3.94 (m, 7H), 2.78 (m, 4H), 2.32 (m, 1H), 1.90 (m, 4H), 1.69 (m, 1H), 1.23 (m, 5H).

Compound 711: $^1$HNMR (400 MHz, DMSO-d6), ppm: 10.14 (t, 1H), 8.42 (d, 1H), 8.07 (d, 1H), 7.89 (t, 1H), 7.83 (t, 1H), 6.09 (s, 1H), 3.95 (m, 4H), 3.56 (m, 2H), 2.70 (m, 4H), 2.31 (m, 1H), 2.85-2.40 (m, 9H), 1.24 (m, 4H), 1.10 (m, 1H), 0.97 (t, 3H).

Compound 1033: $^1$HNMR (400 MHz, DMSO-d6), ppm: 11.85 (s, 1H), 8.42 (d, 1H), 8.10 (d, 1H), 8.02 (d, 2H), 7.79 (t, 1H), 7.64 (t, 1H), 7.50 (d, 2H), 7.31 (s, 1H) 7.17 (d, 1H), 6.91 (d, 1H), 6.42 (s, 1H), 3.92 (m, 4H), 3.79 (s, 3H), 3.52 (s, 2H), 2.62 (m, 4H).

Compound 1035: $^1$HNMR (400 MHz, DMSO-d6), ppm: 10.16 (s, 1H), 8.42 (m, 1H), 8.06 (m, 1H), 7.63 (m, 1H), 7.52 (m, 1H), 6.10 (s, 1H), 4.01 (m, 4H), 3.58 (m, 2H), 2.79 (m, 5H), 2.37 (m, 2H), 2.00-1.80 (m, 6H), 1.63 (m, 1H) 1.28 (m, 4H), 1.10 (m, 1H).

Compound 1243: $^1$HNMR (400 MHz, CCl4 and DMSO-d6), ppm: 8.11 (br s, 1H), 8.01 (s, 1H), 7.64 (m, 2H), 7.57 (m, 2H), 7.41 (m, 1H), 7.32 (m, 2H), 7.17 (m, 2H), 7.10-7.02 (m, 4H), 6.94 (dt, 1H), 5.72 (d, 1H), 5.00 (d, 1H), 3.31 (q, 2H), 2.82 (m, 2H), 2.45 (m, 2H), 2.35 (t, 2H), 1.90 (m, 2H), 1.51 (m, 2H), 1.47 (m, 1H), 1.20 (m, 2H).

5.3 Biological Activities

Compound inhibition in a radiometric based mixed micelle assay: In a final reaction volume of 25 µL, TrkA (h) (3 nM) is incubated with the kinase reaction buffer (20 mM HEPES (pH 7.5), 10 mM MgCl2, 1 mM EGTA, 0.02% Brij 35, 0.02 mg/ml BSA, 0.1 mM Na3VO4, 2 mM DTT, 1% DMSO), 0.2 mg/ml substrate PolyEY(4:1) and 2 nM MnCl2, and [33P-ATP] (specific activity approx. 500 cpm/pmol, concentration as required). The reaction is initiated by the addition of the MgATP mix. After incubation for at least 40 minutes at room temperature, the reaction is stopped by the addition of L of a 3% phosphoric acid solution. 10 µL of the reaction is then spotted onto a P30 filtermat and washed three times for 5 minutes in 75 mM phosphoric acid and once in methanol prior to drying and scintillation counting. TrkA: Recombinant Human Cytoplasmic Domain (amino acids 441-796), Histidine-tagged, expressed in insect cells. Activated in vitro via auto-phosphorylation. Mw=42.8 kDa. Substrates for kinases: poly(EY) for TRKA; poly(EY)(4:1) with 2 mM MnCl$_2$, average Mw=16 kDa Standard conditions (unless otherwise specified): 30 nM TRKA, 0.2 mg/ml poly(EY)+2 mM MnCl$_2$, and 10 µM ([γ-$^{33}$P]) ATP. Using the similar assay condition with other kinases of recombinant human cytoplasmic domain, the activities of other kinases could be also measured.

The TrkA kinase antagonist activity of a compound which may be used in the present invention may be determined by these assays. In particular, the compounds of the present invention aforementioned examples, including tables 1.1 to 3.0 had activity in antagonizing the TrkA kinase activity in the aforementioned assays, generally with an IC50 of less than about 25 µM. Preferred compounds within the present invention had activity in antagonizing the TrkA kinase activity in the aforementioned assays with an IC50 of less than about 2.5 µM. Further preferred compounds within the present invention had activity in antagonizing the TrkA kinase activity in the aforementioned assays with an IC50 of less than about 0.25 µM. The much further preferred compounds within the present invention had activity in antagonizing the TrkA kinase activity in the aforementioned assays with an IC50 of less than about 0.1 µM. For examples, Compound A of the present invention (i.e., Compound 201) has an IC50 of 0.085 µM; Compound B of the present invention has an IC50 of 0.007 µM and has more than about 10 µM of the IC50 values antagonizing, for instances, the following structurally related protein kinases, TrkB, TrkC, ABL1, AKT1, ALK5/TGFB-R1, ARAF, AXL, BMX, BTK, CDK1/cyclinB, CDK2/cyclinA, CDK2/cyclinE, c-MET, c-Src, EPHA1, FES/FPS, FGFR1, FGR, FLT1, FLT3 (CD), FMS, FYN, IGF-1R, IR, ITK, JAK3, JNK3, LCK, LYN, MEK1, MEK2, MLK1/MAP3K9, MUSK, P38a/MAPK14, P38b/MAPK11, PDGFRa, PDGFRb, PKA, PKCalpha, PKCbetaI, PKCbetaII, PKCdelta, PKCepsilon, PKCeta, PKCgamma, PKCiota, PKCmu/PKD1, PKCtheta, PKCzeta, PKD2/PRKD2, PKGIa, PKGIb, RAF1, RET, TEC, TGFbR2, TIE2/TEK, VEGFR2/KDR, VEGFR3/FLT4 (duplicate, with a positive control compound of a pan-kinase inhibitor, staurosporine or K-252a). Such a result is indicative of the intrinsic activity of the compounds in use as isoform-selective antagonists of TrkA kinase activity.

Compound Inhibition in a Live, Whole Cell Based Functional Assay:

There are several methods to measure whole length TrkA activation stimulated by its natural ligand or angonist NGF in live cells. For example, the PathHunter Profiling services offered by DiscoveRx (Fremont, Calif.). The PathHunter technology is an adaptation of enzyme fragment complementation that provides a novel, generic functional cell-based assay format for detecting protein-protein interactions. In this cell-based assay approach, with U2OS cell background, a small peptide epitope (PK) is expressed recombinantly on the intracellular C-terminus of TrkA (human full length). This is co-expressed with a larger sequence, termed enzyme acceptor (EA) that is attached to a cytoplasmic protein SHC1 which will interact with TrkA intracellularly. NGF induced activation of TrkA receptor causes either homo- or hetero-dimerization of TrkA resulting in cross-phosphorylation. The SHC1-EA fusion protein then binds the phosphorylated TrkA receptor forcing complementation of the PK and EA fragment. This interaction generates an active beta-galactosidase enzyme, which is detected using a chemiluminescent substrate.

In such cell-based functional assays, Compound C of the present invention inhibits NGF stimulated TrkA activation at low nanomolar concentration (cellular $IC_{50}$=0.047 µM, mean of triplicate), while virtually has no effect on either BDNF stimulated TrkB, or NT3 stimulated TrkC activation ($IC_{50}$>10 µM in both cases, triplicate, with a postive control compound of pan-kinase inhibitor, staurosporine or K-252a, an internal agonist control and a negative control compound).

Mode of Inhibition with Respect to ATP.

The TrkA kinase assays were performed at room temperature. Four concentrations of compounds (0, 0.037, 0.11, and 0.33 µM) were added into Enzyme/substrate mixture using acoustic technology, and incubated for 40 min to ensure all compounds were equilibrated and bound to the enzyme. Then various concentrations of ATP (10, 100, 200, 350, and 500 µM ATP with 0.2 mg/ml poly(EY)) were added to initiate the reaction. The activity was monitored every 5-15 min for time course. Such kinetic analysis shows that Compound D, for example, inhibits TrkA non-competitively with respect to ATP: Lineweaver-Burk double-reciprocal plots showing differences in Vmax but not in km for the 4 conditions.

Mode of Inhibition with Respect to Substrate.

The kinase assays were performed similar manner to ATP study. Various concentrations of compounds (0, 0.037, 0.11, and 0.33 µM) were added into Enzyme/substrate mixture using acoustic technology, and incubated for 40 min to ensure all compounds were equilibrated and bound to the enzyme. Then 10 µM ATP and various concentrations of substrate (0.02, 0.05, 0.1, 0.2, and 0.5 mg/ml poly(EY)) were added to initiate the reaction. The activity was monitored every 5-15 min for time course. Such kinetic analysis shows that Compound D, for example, inhibits TrkA non-competitively with respect to substrate: Lineweaver-Burk double-reciprocal plots showing differences in Vmax but not in km for the 4 conditions.

Chronic Constriction Injury (CCI) Model of Neuropathic Pain in Rats.

The CCI model is one of the most commonly used mono-neuropathic pain model firstly described in details by Bennett and Xie (Bennett G J, Xie Y K. Pain. 1988; 33(1):87-107). It mimics important clinical chronic pain symptoms such as mechanical allodynia and thermal hyperalgesia. Chronic constriction injury of the sciatic nerve was produced by tying four loose ligatures around the left sciatic nerve according to the method of Bennett and Xie. This procedure resulted in tactile allodynia in the left hindpaw. Calibrated von Frey filaments were used to determine the lowest mechanical (tactile) threshold required to evoke a brisk paw withdrawal reflex in the rat hindpaws. Rats were allowed to acclimatize in wire mesh cages for 15-20 min prior to von Frey testing. Assessment of paw withdrawal thresholds (PWTs) using von Frey filaments was undertaken prior to CCI-surgery (pre-surgery baseline on day 0). Before the drug dosing on day 14, the pre-dose baseline was recorded for each rat. Rats were included in the study only if they did not exhibit motor dysfunction (e.g., paw dragging or dropping) and their PWT was below to 4 g. Drug-naïve CCI-rats (n=4-6 per group) were used. The oral vehicle was 0.5% CMC-Na/0.1% Tween 80 in distilled water. The positive control gabapentin was dissolved in the vehicle and orally given at 100 mg/kg (by oral gavage). Test compound was suspended in the vehicle and orally given at 50 mg/kg and 100 mg/kg. Each CCI-rat was administered a single oral dose of test compound, gabapentin or vehicle control, 2 hours before assessment of PWT.

The results have demonstrated that oral administration of, for example, Compound D of present invention significantly reduced mechanical allodynia in CCI rats of neuropathic pain model in a dose-dependent manner. In addition, at the same oral dose of 100 mg/kg, Compound D is about 98% more effective in suppressing mechanical allodynia in CCI neuropathic pain compared to gabapentin, the current gold standard medication for neuropathic pain, while even 50 mg/kg oral Compound D is about 28% more effective than 100 mg/kg oral gabapentin. Of note, CCI-rats dosed with gabapentin have shown drowsiness or motor incoordination, which is consistent with known side effect of gabapentin. However, no such effect or other abnormality was observed in CCI-rats dosed with Compound D.

Furthermore, there is no statistically significant difference of anti-allodynia effects as measured on day 14 and on day 20 for the same group of CCI-rats treated with the same single oral dose of Compound D at 100 mg/kg, indicating that there is no tolerance issue.

Spinal Nerve Ligation (SNL) Mono-Neuropathic Pain Model in Rats.

The surgical procedure will be performed according to the method firstly described by Kim and Chung (Kim S H, Chung J M. Pain. 1992; 50(3):355-63.). This procedure will result in tactile allodynia in the left hindpaw. Rats will be included in the study only if they do not exhibit motor dysfunction (e.g., paw dragging or dropping) and their PWT is below to 4.0 g. The dose-response anti-allodynia effects of test compound: on day 14 after surgery, rats will be treated with test compound at one of four doses, vehicle or positive control by oral gavage, and PWT is determined by calibrated von Frey filaments at time points of 0 (right before the drug dosing, Pre-Dose Baseline), 0.5, 1, 2, 4 and 6 hr. Tolerance effects: 6 days following the day 14 test, i.e. on day 20 after surgery, the same procedure on day 14 will be repeated on day 20 with the same group of CCI-rats treated with the same (effective) dose as on day 14. The results of anti-allodynia effects of test compound as tested on day 14 and on day 20 will be compared to see if there is any tolerance effect of test compound in animals. The anti-allodynia effects of repeated administration of test compound: Administration of test compound will start on day 7 after surgery, once a day for 7 days. PWT will be determined by calibrated von Frey filaments once a day, 2 hour after compound dosing. After 7 days dosing, the measurement will be continued, every other day without compound dosing for another 7 days. PWT will be determined at the time points as given above. Thermal hyperalgesia effects. Thermal hyperalgesia may be assessed in the SNL rats by plantar test with a single dose of TEST COMPOUND at the time points given above.

D2.2.3. Streptozotocin-Induced Diabetic Poly-Neuropathic Pain Model[a].

Diabetic peripheral neuropathy is a long-term complication of diabetes mellitus. Rats will receive i.p. injections of streptozotocin (STZ, 50 mg/kg dissolved in citrate buffer at pH 4.5 immediately before the injection) to induce insulin-dependent diabetes mellitus and produce tactile allodynia. One week later, blood glucose level will be assayed, from samples taken from the tail vein, using standard test strips and colorimeter. Only animals with a blood glucose level >350 mg/dL will be considered diabetic and included for the testing. Typical features of neuropathic pain (tactile allodynia) will be developed in hindpaws beginning around 2 to 3 weeks after STZ injection. After 4 weeks, a stable level of allodynia will be usually reached. At this point, the rats with PWT below 4.5 g will be enrolled for compound testing. The allodynic state will remain intact until the $8^{th}$ week after STZ injection. All animals will be observed daily and weighed regularly during the study period. This model of neuropathic pain mimics the symptoms of neuropathy in diabetic patients (Lynch J J, 3rd, et al Eur J Pharmacol. 1999; 364(2-3):141-6; Calcutt N A, J Neurol Sci. 2004; 220(1-2):137-9). The dose-response anti-allodynia effects of test compound: On day 28 after STZ injection, rats will be treated with test compound at one of four doses, or controls (vehicle and positive) by oral gavage, and PWT will be determined by calibrated von Frey filaments at time points of 0 (right before the drug dosing, Pre-Dose Baseline), 0.5, 1, 2, 4 and 6 hr. Tolerance effects: 6 days following the day 28 test, i.e. on day 34 after STZ injection, the same procedure on day 28 will be repeated on day 34 with the same group of STZ-rats treated with the same (effective) dose as on day 28. The two results of anti-allodynia effects of test compound as measured on day 28 and on day 34 will be compared to see if there is any tolerance effect of test compound in animals. The anti-allodynia effects of repeated administration of test compound: Administration (p.o.) of test compound will start on day 21 after STZ injection, once a day for 7 days. PWT will be determined by calibrated von Frey filaments once a day, 1 hour after compound dosing. After 7 days dosing, the measurement will be continued, every other day without compound dosing for another 7 days. PWT is determined at the time points as given above. The thermal hyperalgesia assessment by plantar test may be performed in STZ models with a single dose and PWL will be determined, at time points as given above.

5.4 Therapeutic Uses

In accordance with the present invention, a compound of the present invention, or a salt, solvate, ester, and/or a prodrug thereof, or a pharmaceutical composition containing the compound, or a salt, solvate, ester, and/or a prodrug thereof, is administered to a patient, preferably a human, suffering from a variety of disorders. These include cancers, anxiety, generalized pain disorder, acute pain, chronic pain, inflammatory pain and neuropathic pain.

While the invention has been described and illustrated with reference to certain preferred embodiments, those skilled in the art will appreciate that various changes, modifications and substitutions can be made therein without departing from the spirit and scope of the invention.

5.5 Therapeutic/Prophylactic Administration

The present compounds, or salts, solvates, esters, and/or prodrugs thereof, or pharmaceutical compositions containing the present compounds, or salts, solvates, esters, and/or prodrugs thereof, may be advantageously used in human medicine. As previously described in Section 6.4 above, the present compounds are useful for the treatment or prevention of various diseases.

When used to treat or prevent the above-mentioned diseases or disorders, the present compounds may be administered or applied solely, or in combination with other active agents (e.g., other pain agents).

The present invention provides methods of treatment and prophylaxis by administration to a patient in need of such treatment a therapeutically effective amount of one or more compounds of the present invention, or salts, solvates, esters, and/or prodrugs thereof. The patient may be an animal, more preferably, a mammal and most preferably, a human.

The present compounds, or salts, solvates, esters, and/or prodrugs thereof, may be administered orally. The present compounds, or salts, solvates, esters, and/or prodrugs thereof, may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner and will depend in-part upon the site of the medical condition. In most instances, administration will result in the release of the present compounds, or salts, solvates, esters, and/or prodrugs thereof, into the bloodstream of a patient.

In specific embodiments, it may be desirable to administer one or more of the present compounds, or salts, solvates, esters, and/or prodrugs thereof, locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In some embodiments, administration can be accomplished by direct injection at the site (or former site) of cancer or arthritis.

In certain embodiments, it may be desirable to introduce one or more the present compounds, or salts, solvates, esters, and/or prodrugs thereof, into the central nervous system of a patient by any suitable route, including intraventricular, intrathecal and epidural injection. Intraventricular injection may be facilitated by an intraventricular catheter, for example, attached to a reservoir, such as an Ommaya reservoir.

The present compounds, or salts, solvates, esters, and/or prodrugs thereof, may also be administered directly to the lung by inhalation. For administration by inhalation, the present compounds, or salts, solvates, esters, and/or prodrugs thereof, may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas), may be used to deliver compounds of the invention directly to the lung.

Alternatively, a Dry Powder Inhaler ("DPI") device may be used to administer the present compounds, or salts, solvates, esters, and/or prodrugs thereof, to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of the invention and a suitable powder base such as lactose or starch for these systems.

Another type of device that may be used to deliver the present compounds, or salts, solvates, esters, and/or prodrugs thereof, to the lung is a liquid spray device supplied, for example, by Aradigm Corporation, Hayward, Calif. Liquid spray systems use extremely small nozzle holes to aerosolize liquid drug formulations that may then be directly inhaled into the lung. In some embodiments, a nebulizer is used to deliver the present compounds, or salts, solvates, esters, and/or prodrugs thereof, to the lung. Nebulizers create aerosols from liquid drug formulations by using, for example, ultrasonic energy to form fine particles that may be readily inhaled (see e.g., Verschoyle et al., *British J. Cancer,* 1999, 80, Suppl. 2, 96. Nebulizers are available from a number of commericial sources such as Sheffield/Systemic Pulmonary Delivery Ltd. Aventis and Batelle Pulmonary Therapeutics.

In other embodimenst, an electrohydrodynamic ("EHD") aerosol device is used to deliver the present compounds, or salts, solvates, esters, and/or prodrugs thereof, to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering the present compounds, or salts, solvates, esters, and/or prodrugs thereof, to the lung with an EHD aerosol device and such optimization is routinely performed by one of skill in the art. EHD aerosol devices may more efficiently deliver drugs to the lung than existing pulmonary delivery technologies.

In other embodiments, the present compounds, or salts, solvates, esters, and/or prodrugs thereof, can be delivered in a vesicle, in particular a liposome (See, Langer, 1990, *Science,* 249:1527-1533; Treat et al., in "Liposomes in the Therapy of Infectious Disease and Cancer," Lopez-Berestein and Fidler (eds.), Liss, New York, pp. 353-3$^{65}$ (1989); see generally "Liposomes in the Therapy of Infectious Disease and Cancer," Lopez-Berestein and Fidler (eds.), Liss, New York, pp. 353-365 (1989)).

In other embodiments, the present compounds, or salts, solvates, esters, and/or prodrugs thereof, can be delivered via sustained release systems. In still other embodiments, the sustained release system is an oral sustained release systems. In still other embodiments, a pump may be used (See, Langer, supra; Sefton, 1987, *CRC Crit RefBiomed Eng.* 14:201; Saudek et al., 1989, *N. Engl. J Med.* 321:574).

In still other embodiments, polymeric materials can be used in the pharmaceutical compositions containing the present compounds, or salts, solvates, esters, and/or prodrugs thereof. (for exemplary polymeric materials, see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In still other embodiments, polymeric materials are used for sustained release delivery of oral pharmaceutical compositions. Exemplary polymers include, but are not limited to, sodium carboxymethylcellulose, hydroxypropylcellulose, hydroxypropylmethylcellulose and hydroxyethylcellulose (most preferred, hydroxypropyl methylcellulose). Other cellulose ethers have been described (Alderman, *Int. J. Pharm. Tech. & Prod. Mfr.,* 1984, 5(3) 1-9). Factors affecting drug release are well known to the skilled artisan and have been described in the art (Bamba et al., *Int. J. Pharm.,* 1979, 2, 307).

In other embodiments, enteric-coated preparations can be used for oral sustained release administration. Coating materials include, but are not limited to, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.,* 2000, 26:695-708). In still other embodiments, OROS™ osmotic devices are used for oral sustained release delivery devices (Theeuwes et al., U.S. Pat. No. 3,845,770; Theeuwes et al., U.S. Pat. No. 3,916,899).

In still other embodiments, a controlled-release system can be placed in proximity of the target of the present compounds, or salts, solvates, esters, and/or prodrugs thereof, thus requiring only a fraction of the systemic dose (See, e.g., Goodson, in "Medical Applications of Controlled Release," supra, vol. 2, pp. 115-138 (1984)). Other controlled-release systems discussed in Langer, 1990, *Science* 249:1527-1533 may also be used.

5.6 Pharmaceutical Compositions of the Invention

In one aspect, the present invention provides pharmaceutical compositions comprising one or more compounds of the present invention including the compound having structural formula (I) to (VI) and any of their subgeneric groups and specific embodiments described above in Section 5.2.

The present pharmaceutical compositions contain a therapeutically effective amount of one or more compounds of the present invention, or salts, solvates, esters, and/or prodrugs thereof, preferably in purified form, together with a suitable amount of a pharmaceutically acceptable vehicle, so as to provide a form for proper administration to a patient. When administered to a patient, the present compounds and the pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, $20^{th}$ Edition, 2000).

For topical administration a compound may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent such as another anti-cancer agent.

In some embodiments, the present compounds, or salts, solvates, esters, and/or prodrugs thereof, are formulated in accordance with routine procedures as a pharmaceutical composition adapted for intravenous administration to human beings. Typically, compounds for intravenous administration are solutions in sterile isotonic aqueous buffer. For injection, the present compounds, or salts, solvates, esters, and/or prodrugs thereof, may be formulated in aqueous solutions, preferably, in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the present compounds, or salts, solvates, esters, and/or prodrugs thereof, are administered by infusion, it can be dispensed, for example, with an infusion bottle containing sterile pharmaceutical grade water or saline. When the present compounds, or salts, solvates, esters, and/or prodrugs thereof, are administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the invention with a pharmaceutically acceptable vehicle. In some embodiments, the pharmaceutically acceptable vehicle is a liquid such as alcohol, water, polyethylene glycol or a perfluorocarbon. Optionally, another material may be added to alter the aerosol properties of the solution or suspension of compounds disclosed herein. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

The present compounds, or salts, solvates, esters, and/or prodrugs thereof, may also be formulated in rectal or vaginal pharmaceutical compositions such as suppositories or retention enemas, e.g., containing conventional suppository bases such as cocoa butter or other glycerides.

In addition to the formulations described previously, the present compounds, or salts, solvates, esters, and/or prodrugs thereof, may also be formulated as a depot preparation. Such long acting formulations may be administered by implantation (for example, subcutaneously or intramuscularly) or by intramuscular injection. Thus, for example, the present compounds, or salts, solvates, esters, and/or prodrugs thereof, may be formulated with suitable polymeric or hydrophobic materials (for example, as an emulsion in an acceptable oil) or ion exchange resins, or as sparingly soluble derivatives, for example, as a sparingly soluble salt.

5.7 Therapeutic Doses

The present compounds, or a salt, prodrug or softdrug, salt of prodrug or softdrug, solvate or hydrate thereof and a pharmaceutically acceptable vehicle is provided, will generally be used in an amount effective to achieve the intended purpose. For use to treat or prevent diseases or disorders characterized by down regulated apoptosis the compounds and/or pharmaceutical compositions thereof, are administered or applied in a therapeutically effective amount.

The amount of the present compounds, or salts, solvates, esters, and/or prodrugs thereof, that will be effective in the treatment of a particular disorder or condition disclosed herein will depend on the nature of the disorder or condition, and can be determined by standard clinical techniques known in the art. In addition, in vitro or in vivo assays may optionally be employed to help identify optimal dosage ranges. The amount of the present compounds, or salts, solvates, esters, and/or prodrugs thereof, administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the present compounds, or salts, solvates, esters, and/or prodrugs thereof, are delivered by oral sustained release administration. Dosing may be repeated intermittently, may be provided alone or in combination with other drugs and may continue as long as required for effective treatment of the disease state or disorder.

Suitable dosage ranges for oral administration depend on the potency of the present compounds, but are generally between about 0.001 mg to about 200 mg of a compound of the invention per kilogram body weight. Dosage ranges may be readily determined by methods known to the artisan of ordinary skill.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

The present compounds, or salts, solvates, esters, and/or prodrugs thereof, are preferably assayed in vitro and in vivo, for the desired therapeutic or prophylactic activity, prior to use in humans. For example, in vitro assays can be used to determine whether administration of a specific compound of the invention or a combination of compounds is preferred for inducing apoptosis in cells which over-express bcl-2 proteins. The present compounds, or salts, solvates, esters, and/or prodrugs thereof, may also be demonstrated to be effective and safe using animal model systems.

Preferably, a therapeutically effective dose of the present compounds, or salts, solvates, esters, and/or prodrugs thereof, will provide therapeutic benefit without causing substantial toxicity. Toxicity of the present compounds, or salts, solvates, esters, and/or prodrugs thereof, may be determined using standard pharmaceutical procedures and may be readily ascertained by the skilled artisan. The dose ratio between toxic and therapeutic effect is the therapeutic index. The present compounds, or salts, solvates, esters, and/or prodrugs thereof, generally exhibit particularly high therapeutic indices in treating apoptosis associated disease and disorders. The dosage of the present compounds, or salts, solvates, esters, and/or prodrugs thereof, will preferably be within a range of circulating concentrations that include an effective dose with little or no toxicity.

5.8 Combination Therapy

In certain embodiments of the present invention, the present compounds, or salts, solvates, esters, and/or prodrugs thereof, can be used in combination therapy with at least one additional active or therapeutic agent. The present compounds, or salts, solvates, esters, and/or prodrugs thereof, and the at least one additional active or therapeutic agent can act additively or, more preferably, synergistically. In some embodiments, the present compounds, or salts, solvates, esters, and/or prodrugs thereof are administered concurrently, sequentially, or separately with the administration of another therapeutic agent. Exemplary active or chemotherapeutic agents include, but are not limited to, aceglatone, aclarubicin, altretamine, aminoglutethimide; 5-aminogleavulinic acid, amsacrine, anastrozole, ancitabine hydrochloride, 17-la antibody, antilymphocyte immunoglobulins, antineoplaston a10, asparaginase, pegaspargase, azacitidine, azathioprine, batimastat, benzoporphyrin derivative, bicalutamide, bisantrene hydrochloride, bleomycin sulphate, brequinar sodium, broxuridine, busulphan, campath-ih, caracemide, carbetimer, carboplatin, carboquone, carmofur, carmustine, chlorambucil, chlorozotocin, chromomycin, cisplatin, cladribine, *corynebacterium parvum*, cyclophosphamide, cyclosporin, cytarabine, dacarbazine, dactinomycin, daunorubicin hydrochloride, decitabine, diaziquone, dichlorodiethylsulphide, didemnin b., docetaxel, doxifluridine, doxorubicin hychloride, droloxifene, echinomycin, edatrexate, elliptinium, elmustine, enloplatin, enocitabine, epirubicin hydrochloride, estramustine sodium phosphate, etanidazole, ethoglucid, etoposide, fadrozole hydrochloride, fazarabine, fenretinide, floxuridine, fludarabine phosphate, fluorouracil, flutamide, formestane, fotemustine, gallium nitrate, gencitabine, gusperimus, homoharringtonine, hydroxyurea, idarubicin hydrochloride, ifosfamide, ilmofosine, improsulfan tosylate, inolimomab, interleukin-2; irinotecan, jm-216, letrozole, lithium gamolenate, lobaplatin, lomustine, lonidamine, mafosfamide, meiphalan, menogaril, mercaptopurine, methotrexate, methotrexate sodium, miboplatin, miltefosine, misonidazole, mitobronitol, mitoguazone dihydrochioride, mitolactol, mitomycin, mitotane, mitozanetrone hydrochloride, mizoribine, mopidamol, muitlaichilpeptide, muromonabcd3, mustine hydrochloride, mycophenolic acid, mycophenolate mofetil, nedaplatin, nilutamide, nimustine hydrochloride, oxaliplatin, paclitaxel, pcnu, penostatin, peplomycin sulphate, pipobroman, pirarubicin, piritrexim isethionate, piroxantrone hydrochloride, plicamycin, porfimer sodium, prednimustine, procarbazine hydrochloride, raltitrexed, ranimustine, razoxane, rogletimide, roquinimex, sebriplatin, semustine, sirolimus, sizofiran, sobuzoxane, sodium bromebrate, sparfosic acid, sparfosate sodium, sreptozocin, sulofenur, tacrolimus, tamoxifen, tegafur, teloxantrone hydrochloride, temozolomide, teniposide, testolactone, tetrasodium mesotetraphenylporphine-sulphonate, thioguanine, thioinosine, thiotepa, topotecan, toremifene, treosulfan, trimetrexate, trofosfamide, tumor necrosis factor, ubenimex, uramustine, vinblastine sulphate, vincristine sulphate, vindesine sulphate, vinorelbine tartrate, vorozole, zinostatin, zolimomab aritox, and zorubicin hydrochloride, and the like, either individually or in any combination, an inhibitor of protein kinase A (PKA), an inhibitor of cAMP signaling, a nonsteroidal anti-inflammatory drug, a prostaglandin synthesis inhibitor, a local anesthetic, an anticonvulsant, an antidepressant, an opioid receptor agonist, and a neuroleptic, a benzodiazepine, a barbiturate, a neurosteroid and a inhalation anesthetic, a anesthetic and another pain killer.

All publications and patent applications herein are incorporated by reference to the same extent as if each individual publication or patent application was specifically and individually indicated to be incorporated by reference. The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound having a structural formula (IVb.21):

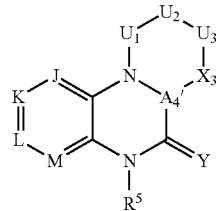

(IVb.21)

or a salt, ester, or prodrug thereof, wherein

J, K, and M are CH, and L is C—CONR$^8$R$^9$;

$U_1$, $U_2$, and $X_3$ are independently C(R$^{20}$) or C(R$^{20}$R$^{21}$);

$U_3$ is C(R$^{20}$R$^{21}$);

$A_4'$ is C or CR$^{22}$;

N—$U_1$, $U_2$—$U_3$, and $U_3$—$X_3$ are a single bond;

$A_4'$-$X_3$ and $U_1$—$U_2$ are independently single or double bond;

Y is O or S;

R$^5$ is hydrogen, alkyl, arylalkyl, or substituted arylalkyl;

R$^8$ is hydrogen and R$^9$ is C$_{1-6}$ alkyl substituted with an N-piperazinyl ring which is substituted at the nitrogen atom by phenyl, substituted phenyl, or 5-10 membered heteroaryl; and R$^{20}$, R$^{21}$, and R$^{22}$ are hydrogen.

2. The compound of claim 1, wherein Y is O.

3. The compound of claim 1, which is selected from the group consisting of:

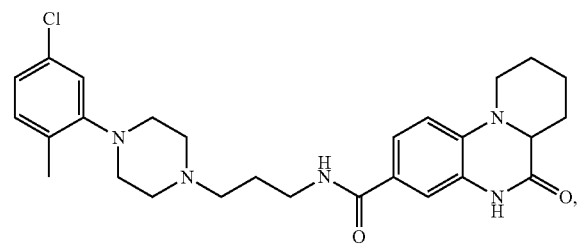

(201)

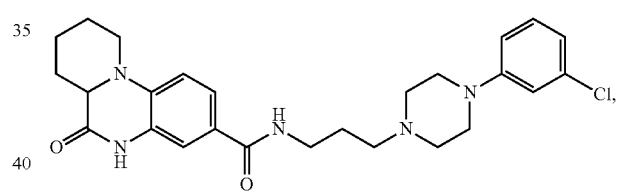

(289)

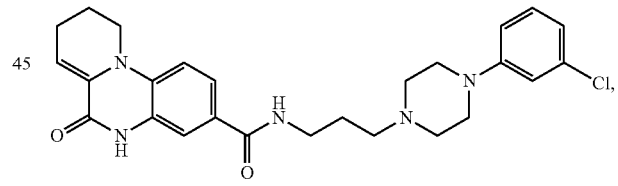

(551)

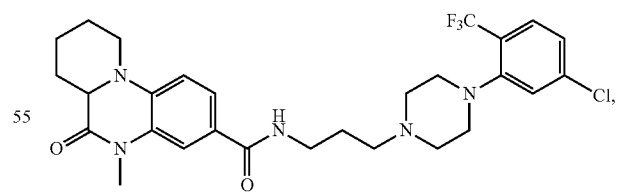

(553)

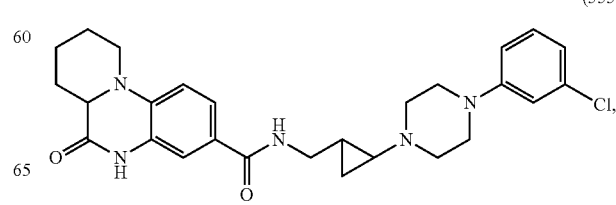

(555)

-continued

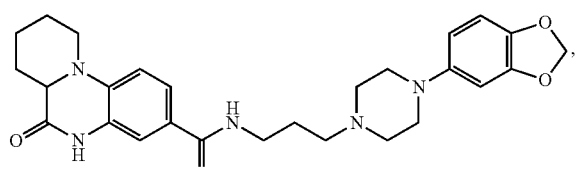
(557)

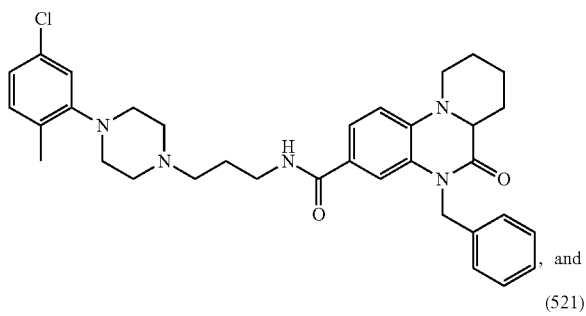
(517)

, and

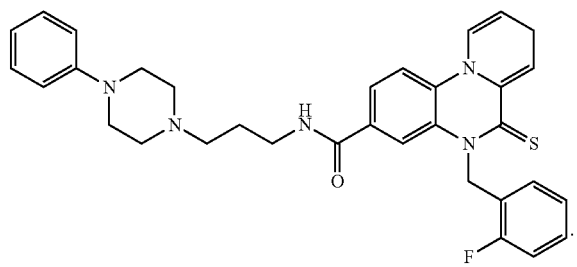
(521)

4. A pharmaceutical composition, comprising a therapeutically effective amount of a compound of claim 1, or a salt, ester, or prodrug thereof, and at least one pharmaceutically acceptable vehicle.

5. The pharmaceutical composition of claim 4, wherein the composition is formulated as: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, or an intracerebral unit dosage form.

6. The pharmaceutical composition of claim 4, wherein the composition is formulated as: an oral unit dosage form, which is suitable for administration of about 0.001 mg to about 200 mg of the compound per kilogram body weight to a patient in need thereof.

7. The pharmaceutical composition of claim 4, wherein the composition is formulated as: an intravenous unit dosage form, which is suitable for administration of about 0.01 mg to about 100 mg of the compound per kilogram of body weight to a patient in need thereof.

8. The pharmaceutical composition of claim 4, wherein the composition is formulated as:
(a) an intranasal unit dosage form, which is suitable for administration of about 0.01 mg to about 1 mg of the compound per kilogram of body weight to a patient in need thereof;
(b) a suppository unit dosage form, which is suitable for administration of about 0.01 mg to about 50 mg of the compound per kilogram of body weight to a patient in need thereof and comprises active ingredient in the range of about 0.5% to about 10% by weight; or
(c) an intradermal, intramuscular, intraperitoneal, subcutaneous, epidural, sublingual, or intracerebral unit dosage form, which is suitable for administration of about 0.001 mg to about 200 mg of the compound per kilogram of body weight to a patient in need thereof.

9. The pharmaceutical composition of claim 4, which is in a form selected from: tablets, pills, pellets, capsules, powders, lozenges, granules, solutions, suspensions, emulsions, syrups, elixirs, sustained-release formulations, aerosols, and sprays.

10. The pharmaceutical composition of claim 4, which is in the form of a tablet, a capsule, or an oral liquid preparation.

11. The pharmaceutical composition of claim 5, wherein the composition is formulated as an oral unit dosage form and further comprises one or more optional agents selected from the group consisting of sweetening agents, flavoring agents, coloring agents, preserving agents, time delay or delay disintegration materials, standard oral vehicles, suitable carriers, excipients, and diluents.

12. The pharmaceutical composition of claim 4, further comprising: at least one additional active agent selected from the group consisting of: an inhibitor of protein kinase A (PKA), an inhibitor of cAMP signaling, a nonsteroidal anti-inflammatory drug, a prostaglandin synthesis inhibitor, a local anesthetic, an anticonvulsant, an antidepressant, an opioid receptor agonist, a neuroleptic, an agonist of $GABA_A$ receptor, an analgesic or anti-cancer agent that acts by a mechanism different from a TrkA antagonist, a benzodiazepine, a barbiturate, a neurosteroid, an inhalation anesthetic, an anesthetic, an anticancer drug, a modulator of mGluR5 receptor, and a combination thereof.

13. The pharmaceutical composition of claim 4, wherein the compound is selected from the group consisting of:

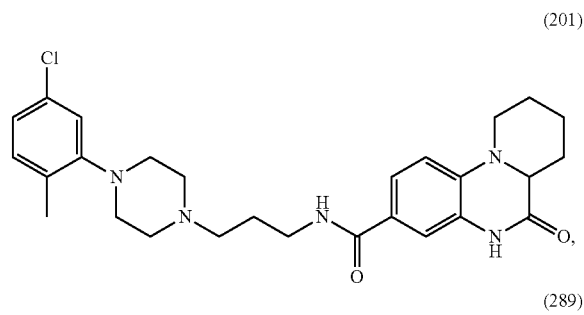
(201)

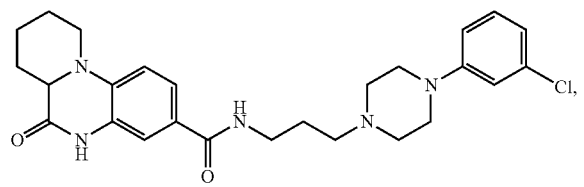
(289)

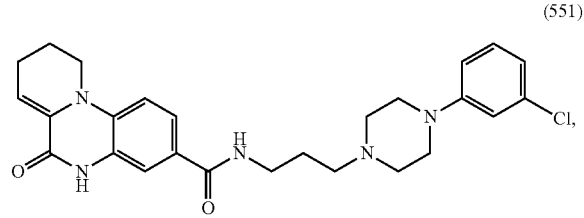
(551)

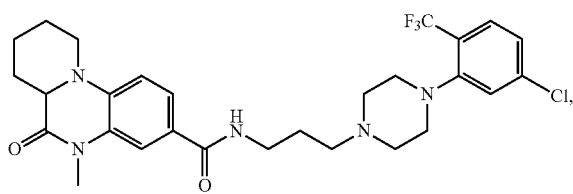
(553)

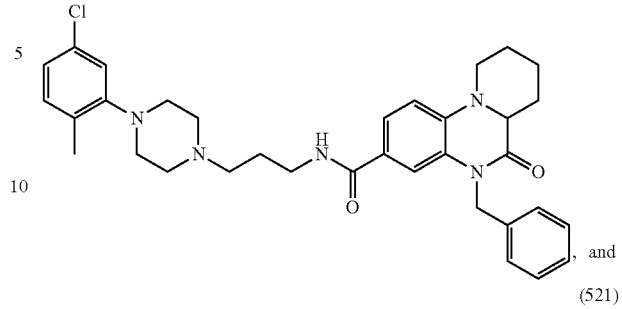
(517)

, and

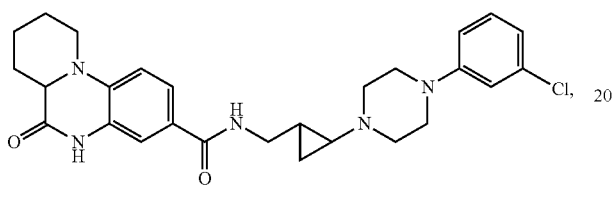
(555)

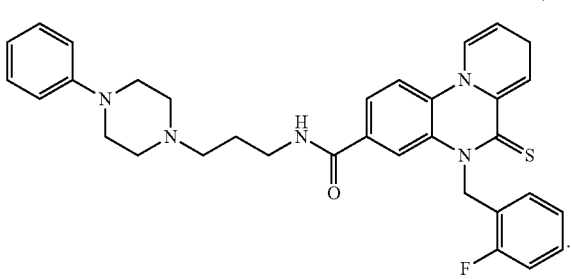
(521)

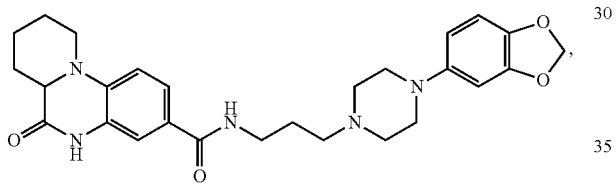
(557)

14. A method of treating pain in a patient suffering therefrom, comprising: administering to the patient a compound of claim 1, or a salt, ester, or prodrug thereof.

15. The method of claim 14, wherein said pain is selected from the group consisting of: acute pain, chronic pain, inflammatory pain, neuropathic pain, tonic pain, persistent pain, postoperative pain, chemical-induced pain, chemotherapy-induced pain, cancer-pain, drug-induced pain, bone pain, arthritis pain, osteoarthritis pain, fibromyalgia, diabetic neuropathic pain, a generalized pain disorder, pain associated with alcohol-induced hyperalgesia, and a combination thereof.

\* \* \* \* \*